Figure 1:
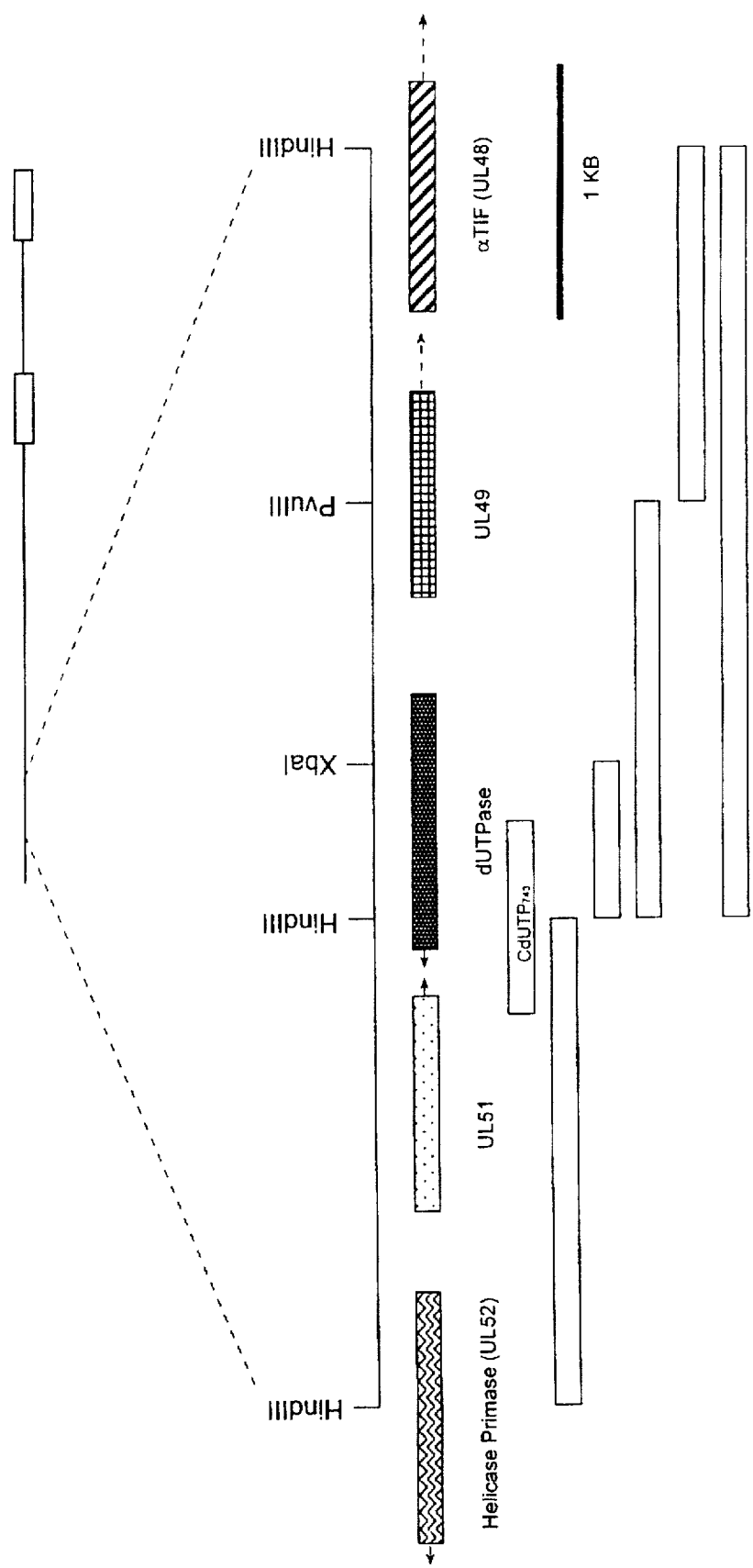

United States Patent [19]
Haanes et al.

[11] Patent Number: 5,753,235
[45] Date of Patent: May 19, 1998

[54] RECOMBINANT CANINE HERPESVIRUSES

[75] Inventors: Elizabeth J. Haanes, Boulder; Rexann S. Frank, Wellington, both of Colo.

[73] Assignee: Heska Corporation, Ft. Collins, Colo.

[21] Appl. No.: 602,010

[22] Filed: Feb. 15, 1996

[51] Int. Cl.$^6$ .......................... A61K 39/245; C12N 7/01; C07K 1/00; C12P 21/02
[52] U.S. Cl. ................................. 424/229.1; 424/147.1; 435/235.1; 530/388.3; 530/395
[58] Field of Search ............................ 424/229.1, 147.1; 435/235.1; 530/388.3, 395

[56] References Cited

U.S. PATENT DOCUMENTS

| | | | |
|---|---|---|---|
| 5,223,424 | 6/1993 | Cochran et al. | 435/236 |
| 5,266,489 | 11/1993 | Rey-Senelonge et al. | 435/320.1 |
| 5,310,668 | 5/1994 | Ellis et al. | 435/172.3 |
| 5,324,664 | 6/1994 | Nunberg et al. | 435/320.1 |

FOREIGN PATENT DOCUMENTS

WO 95/26751 10/1995 WIPO.

OTHER PUBLICATIONS

Binn, et al., "Virsuses Recovered from Laboratory Dogs with Respiratory Disease," pp. 140–145, P.S.E.B.M. (rec'd May 17, 1967) v. 126.

Breeden, et al., "Identification and Transcriptional Mapping of Genes Encoded at the IR/Us Junction of Equine Herpesvirus Type 1," pp. 649–660, Virology, 191 (1992).

Carmichael, "Herpesvirus canis: Aspects of Pathogenesis and Immune Response," pp. 1714–1721, J.A.V.M.A., vol. 156 (Jun. 15, 1970).

de Wind, et al., "Ribonucleotide reductase–deficient mutants of pseudorabies virus are avirulent for pigs and induce partial protective immunity," pp. 351–359, Journal of General Virology, 74 (1993).

Elton, et al., "Sequence analysis of the 4.7-kb BamHI-EcoRI fragment of the equine herpesvirus type–1 short unique region," pp. 203–208, Elsevier Science Publishers B.V. 0378–1119/91 (1991).

Graham, et al., "A New Technique for the Assay of Infectivity of Human Adenovirus 5 DNA," pp. 456–467, Virology, 52 (1973).

Holliday, et al., "Inhibition of herpes simplex virus types 1 and 2 replication in vitro by mercurithio analogs of deoxyuridine," pp. 197–203, Antiviral Research, 16 (1991).

Kit, et al., "Nucleotide Sequence Changes in Thymidine Kinase Gene of Herpes Simplex Virus Type 2 Clones from an Isolate of a Patient Treated with Acyclovir," pp. 1483–1490, Antimicrobial Agents and Chemotherapy, vol. 31, No. 10 (Oct. 1987).

Kit, et al., "Thymidine Kinase (TK) Induction after Infection of TK–Deficient Rabbit Cell Mutants with Bovine Herpesvirus Type 1 (BHV–1): Isolation of TK⁻BHV–1 Mutants," pp. 381–389, Virology, 130 (1983).

Lees et al., "The Epstein–Barr Virus Candidate Vaccine Antigen gp340/220 is Highly Conserved between Virus Types A and B," pp. 578–586, Virology, 195 (1993).

Liang, et al., "Identification and Deletion Mutagenesis of the Bovine Herpesvirus 1 dUTPase Gene and a Gene Homologous to Herpes Simplex Virus UL49.5," pp. 42–50, Virology, 195 (1993).

Limbach, et al., "Nucleotide sequence of the genes encoding the canine herpesvirus gB, gC and gC homologues," pp. 2029–2039, Journal of General Virology, 75 (1994).

McGeoch, et al., The Complete DNA Sequence of the Long Unique Region in the Genome of Herpes Simplex Virus Type 1, pp. 1531–1574, Journal of General Virology, 69 (1988).

McGeoch, et al., "Sequence Determination and Genetic Content of the Short Unique Region in the Genome of Herpes Simplex Virus Type 1," pp. 1–13, 1985 Academic Press Inc. (London) Ltd. (received 30 Jul. 1984).

Meignier, et al., "Virulence of and Establishment of Latency by Genetically Engineered Deletion Mutants of Herpes Simplex Virus 1," pp. 251–254, Virology, 162 (1988).

Meinkoth, et al., "Hybridization of Nucleic Acids Immobilized on Solid Supports," pp. 267–284, Analytical Biochemistry, 138 (1984).

Nunberg, et al., "Identification of the Thymidine Kinase Gene of Feline Herpesvirus: Use of Degenerate Oligonucleotides in the Polymerase Chain Reaction to Isolate Herpesvirus Gene Homologs," pp. 3240–3249, Journal of Virology, vol. 63, No. 8 (Aug. 1989).

Peterson, et al., "Propagation and Quantitation of Animal Herpesviruses in Eight Cell Culture Systems," pp. 93–98, Comp. Immun. Microbiol. Infect. Dis., vol. 11, No. 2 (1988).

Rémond, et al., "Gene organization in the $U_L$ region and inverted repeats of the canine herpesvirus genome," pp. 37–48, Journal of General Virology, 77 (1996).

Rémond, et al., "Sequence of the canine herpesvirus thymidine kinase gene: taxon–preferred amino acid residues in the alphaherpesviral thymidine kinases," pp. 341–354, Virus Research, 39 (1995).

(List continued on next page.)

Primary Examiner—Ponnathapura Achutamurthy
Assistant Examiner—Phuong T. Bui
Attorney, Agent, or Firm—Sheridan Ross P.C.

[57] ABSTRACT

The present invention includes novel recombinant canine herpes virus (CHV) and novel recombinant CHV genomes, and particularly to those CHV and CHV genomes that contain heterologous nucleic acid molecules. The present invention also relates to the use of such genomes and viruses in a variety of applications, including as therapeutic compositions to protect animals from disease. The present invention also relates to novel isolated CHV nucleic acid molecules, to CHV proteins encoded by such nucleic acid molecules, and to antibodies raised against such CHV proteins as well as to the use of such CHV nucleic acid molecules, proteins and antibodies as therapeutic compositions to protect an animal from CHV. The present invention also includes constructs comprising CHV nucleic acid molecules that include heterologous nucleic acid molecules, to recombinant vectors including such constructs, and to the use of such constructs and vectors in the production of recombinant CHV and recombinant CHV genomes.

57 Claims, 3 Drawing Sheets

OTHER PUBLICATIONS

Riggio, et al., "DNA sequence of a gene cluster in the equine herpesvirus-4 genome which contains a newly identified herpesvirus gene encoding a membrane protein," pp. 171–178, *Archives of Virology*, 133 (1993).

Robertson, et al., Evolution of the herpes thymidine kinase: identification and comparison of the equine herpesvirus 1 thymidine kinase gene reveals similarity to a cell-encoded thymidylate kinase, pp. 11303–11317, *Nucleic Acids Research*, vol. 16, No. 23 (1988).

Simard, et al., "Sequencing and 5'-and 3'-end Transcript Mapping of the Gene Encoding the Small Subunit of Ribonucleotide Reductase from Bovine Herpesvirus Type–1," pp. 689–701, *Virology*, 190 (1992).

Spatz, et al., "Identification of the feline herpesvirus type 1 (FHV–1) genes encoding glycoproteins G, D, I and E: expression of FHV-1 glycoprotein D in vaccinia and raccoon poxviruses," pp. 1235–1244, *Journal of General Virology*, 75 (1994).

Tack, et al., The Complete DNA Sequence and the Genetic Organization of the Short Unique Region ($U_s$) of the Bovine Herpesvirus Type 1 (ST Strain), pp. 409–421, *Virology*, 199–(1994).

Telford, et al., "The DNA Sequence of Equine Herpesvirus–1," pp. 304, 316, *Virology*, 189 (1992).

van Zijl, et al., "Regeneration of Herpesviruses for Molecularly Cloned Subgenomic Fragments," pp. 2191–2195, *Journal of Virology*, vol. 61, No. 6 (Jun. 1988).

Walboomers, et al., "A New Method for the Isolation of Herpes Simplex Virus Type 2 DNA," pp. 256–258, *Virology*, 74 (1976).

Wolff, et al., "Detect Gene Transfer into Mouse Muscle in Vivo," pp. 1465–1468, *Science*, vol. 247 (23 Mar. 1990).

Pyles et al. "Herpes Simplex Virus Type 1 dUTPase . . . " J Virol vol. 66, No. 11, Nov. 1992, pp. 6706–6713.

Riggio et al. "DNA Sequence of a Gene Cluster . . . " Arch Virol 1993, 133:171–178.

Liang et al. "Identification and Deletion Mutagenesis . . . " Virology 195, pp. 42–50, 1993.

Pyles et al. "Mutations in Accessory DNA Replicating . . . " J Virol vol. 68, No. 7. Jul. 1994, pp. 4514–4524.

Fields et al. Fields Virology, 1996, vol. 2, Chap 72 pp. 2231–2295 "Herpes Simplex Viruses and . . . ".

RECOMBINANT CANINE HERPESVIRUSES

FIELD OF THE INVENTION

The present invention relates to canine herpesvirus (CHV), and particularly to novel recombinant CHV and recombinant CHV genomes, including those that contain heterologous nucleic acid molecules. The present invention also relates to the use of such genomes and viruses in a variety of applications, including as therapeutic compositions to protect animals from disease. The present invention also relates to novel isolated CHV nucleic acid molecules, to proteins encoded by such nucleic acid molecules, and to use of such CHV nucleic acid molecules to insert heterologous nucleic acid molecules into CHV genomes.

BACKGROUND OF THE INVENTION

Dogs and other canids are affected by a number of diseases against which it would be desirable to develop protective vaccines. Live vaccines, and particularly live viral vector vaccines, are attractive vaccine vector candidates as they appear to be associated with longer-lasting immunity than inactivated virus vaccines or subunit vaccines. One disadvantage of live vaccines, however, has been that attenuated virus strains often revert to virulence. Another disadvantage has been the host range of a number of viral vaccines. In an attempt to deliver genes to an animal, several viral and bacterial systems, such as poxviruses, adenoviruses, Salmonella, and BCG (*Bacillus Calmette-Guerin*), have been genetically manipulated to generate vectors containing heterologous antigen genes in order to immunize a host with a vaccine in which the antigens are presented in a "live" configuration. See, for example, the following two review articles: Esposito et al., pp. 195–247, 1989, Advances in Veterinary Science and Comparative Medicine, Vol. 33; Dougan et al., pp. 271–300, 1989, Advances in Veterinary Science and Comparative Medicine, Vol. 33.

Several herpes virus vaccines, such as those based on bovine herpes virus (BHV), cytomegalovirus (CMV), Epstein Barr virus (EBV), equine herpes virus (EHV), feline herpes virus (FHV), herpes simplex virus (HSV), Marek's disease virus (MDV), pseudorabies virus (PRV), turkey herpes virus (HVT), and varicella zoster virus (VZV) have been developed and several have shown at least some efficacy as vaccines against the virus per se or as vectors carrying other genes in certain indications. The listed herpes viruses, however, also have the drawback that even if attenuated, they are subject to reversion.

Canine herpes virus (CHV) infection is a relatively benign infection except in newborn puppies. A few vaccines to protect against CHV infection have been reported including a small-plaque variant CHV vaccine disclosed in U.S. Pat. No. 4,213,965, by Carmichael, issued Jul. 22, 1980. The nucleotide sequences of CHV genes encoding gB, gC, gD and UL45 homologs have been reported by Limbach et al., 1994, J. Gen. Virol. 75, 2029–2039, but these proteins, while proposed as vaccine candidates against CHV, were not tested as such by Limbach et al., ibid.

The inventors are not aware of any reports which describe the use of CHV as a vaccine vector, either with respect to inactivating genes in the CHV genome using recombinant DNA techniques, and/or to delivering protective compounds to a canid, in spite of the need to develop safe and efficacious delivery systems to protect canids, and especially dogs, from disease. Two U.S. patents (i.e., U.S. Pat. No. 5,266,489, by Rey-Senelonge et al., issued Nov. 30, 1993; and U.S. Pat. No. 5,223,424, by Cochran et al., issued Jun. 29, 1993) at best speculate on the insertion of genes into certain CHV loci, but neither claims CHV vectors or vaccines, nor provides data supporting such speculations. U.S. Pat. No 5,266,489, ibid., claimed HVT having a foreign gene inserted into the ribonucleotide reductase (RR) small subunit gene of the HVT genome, but also disclosed without support the insertion of foreign genes into the RR small subunit genes of BHV, CHV, CMV, duck herpes virus, EBV, EHV, FHV, HSV, PRV and VZV. The inventors, however, have demonstrated the inaccuracy of this disclosure in that the inventors have found, and disclosed in the present application, that the CHV genome lacks the RR small subunit gene. That is, the CHV RR small subunit gene does not exist to provide a target for the insertion of foreign genes.

U.S. Pat. No. 5,223,424, ibid., claimed specific hybrid PRV constructs having deletions in the TK, repeat, or and/or gX regions and heterologous sequences inserted into the repeat and/or gX regions, but also proposed without data the ability to insert foreign genes into the repeat region of the CHV genome, even though that genome had not yet been mapped. Also disclosed were certain BHV and HVT constructs and proposals, without data, to delete and insert genes in other herpesviruses, such as EHV and FHV, HSV and MDV. It is also of note that a patent application (now U.S. Pat. No. 5,273,876, by Hock et al, issued Dec. 28, 1993) that was filed significantly later than U.S. Pat. No. 5,223,424, ibid., and shares two co-inventors with U.S. Pat. No. 5,223,424, ibid., states in column 2, lines 57–61, "Among the herpesviruses, only four herpesviruses (herpes simplex of humans, herpes saimiri of monkeys, pseudorabies virus and varicella-zoster virus) have been engineered to contain foreign DNA sequences previous to this disclosure," thereby indicating the lack of CHV, or a number of other, herpes virus vectors.

Thus, there remains a need for new and improved methods to vaccinate canids to protect them from diseases, such as those caused by genetic or metabolic disorders as well as those caused by infectious agents such as protozoan parasites, helminth parasites, ectoparasites, fungi, bacteria, and viruses.

SUMMARY OF THE INVENTION

The present invention relates to a new method to protect animals from disease using a recombinant virus or virus genome. When a recombinant CHV of the present invention is administered to an animal, the virus is able to infect cells within the animal. Infected cells are able to express nucleic acid sequences present on the recombinant CHV genome to produce protective compounds, such as proteins and RNAs, capable of protecting the animal from a variety of diseases. Using methods taught in the present invention, vaccines can be generated that are capable of protecting an animal from any disease for which a protective compound can be produced. As such, the present invention is of extremely broad scope and includes a wide variety of vaccines that have a variety of applications.

The present invention includes a recombinant CHV that comprises a recombinant CHV genome. The invention also includes recombinant CHV genomes. In one embodiment, a recombinant CHV has an inactive gene within its genome, with a preferred recombinant CHV in this embodiment being a CdUTPase negative CHV, a CgC negative CHV, a CgE negative CHV, a CgG negative CHV, a CgI negative CHV, a CPK negative CHV, a CTK negative CHV, a CIR6 negative CHV, a CUS2 negative CHV, a CUS9 negative CHV, a CUL49 negative CHV, a CUL51 negative CHV, a CUL45 negative CHV, a CgD negative CHV, a CgB negative CHV, a CUL48 negative CHV, and/or a CUL52 negative CHV.

The present invention also includes a recombinant CHV genome that comprises a heterologous nucleic acid molecule, which preferably encodes a protective compound that protects a canid from disease. Such a heterologous nucleic acid molecule can be located in an essential gene, a nonessential gene, and/or in an intergenic region. Insertion of a heterologous nucleic acid into a CHV genome can, but need not, inactivate a gene within that genome. Also included in the present invention are methods to produce a recombinant CHV and a recombinant CHV genome, as well as a canine cell line that complements a defect in a gene essential to CHV reproduction in vitro.

One embodiment of the present invention is a therapeutic composition that includes a recombinant CHV, a recombinant CHV genome, or a mixture thereof. The present invention also includes a method to protect an animal from disease by administering such a therapeutic composition to the animal.

The present invention also includes an isolated CHV nucleic acid molecule that hybridizes under stringent hybridization conditions with at least one of the following nucleic acid regions: a CdUTPase gene, a CgE gene, a CgG gene, a CgI gene, a CPK gene, a CTK gene, a CIR6 gene, a CUS2 gene, a CUS9 gene, a CUL49 gene, a CUL51 gene, a CUL48 gene, a CUL52 gene and/or a region of the CHV genome spanning from about the 3' end of the coding region of the CUL41 gene through about the 3' end of the coding region of the CUL38 gene. Also included are recombinant molecules, recombinant viruses, recombinant vectors, and recombinant cells that include such CHV nucleic acid molecules. The present invention also includes CHV proteins encoded by such CHV nucleic acid molecules and antibodies that selectively bind to such CHV proteins, as well as methods to produce such CHV nucleic acid molecules, recombinant molecules, recombinant viruses, recombinant vectors, recombinant cells, CHV proteins and antibodies. Also included in the present invention are therapeutic compositions including such CHV nucleic acid molecules, CHV proteins and antibodies, as well as methods to use such compositions to protect an animal from disease.

BRIEF DESCRIPTION OF THE FIGURES

FIG. 1 depicts a schematic map of two contiguous HindIII fragments that include at least portions of CHV UL48 UL49, dUTPase, UL51 and UL52 genes.

FIG. 2 depicts a schematic map of the AscI fragment that includes the unique short region of CHV.

FIG. 3 depicts a schematic map of the AscI/blunt fragment that includes the terminal inverted repeat region of CHV.

DETAILED DESCRIPTION OF THE INVENTION

The present invention relates to canine herpesviruses (CHV), and particularly to recombinant CHV and recombinant CHV genomes as well as to methods to produce and use such viruses and genomes. The present invention also includes identification of regions of the CHV genome that are preferred targets for deletion and/or for insertion of heterologous nucleic acid molecules. As used herein, the term "canine" refers to "of the family Canidae" and, as such, includes reference to dogs (including wild and domesticated dogs), foxes, wolves, jackals, coyotes, and other members of the family Canidae. Similarly, a "canid" is any member of the family Canidae. As used herein, the term CHV refers to any herpesvirus endogenous to the family Canidae. A particularly preferred CHV of the present invention is a recombinant CHV that infects dogs.

One embodiment of the present invention is the use of a recombinant CHV, and particularly of a CHV having a recombinant CHV genome that includes a (i.e., one or more than one) heterologous nucleic acid molecule, as a live CHV-based therapeutic composition, or vaccine, to protect an animal from a disease against which the heterologous nucleic acid molecule is targeted. Live vaccines are advantageous because they are believed to confer more vigorous and longer-lasting immunity than subunit or killed vaccines. While not being bound by theory, it is believed that such advantages are due to the ability of the genetic information carried by the virus to enter cells of the treated animal, replicate itself, and direct the expression of a protective compound, such as a protective protein or a protective RNA, for extended periods of time. Thus, the therapeutic composition need not be administered frequently and, at least in some embodiments, the virus vaccine can function as a self-booster.

CHV is particularly useful as a delivery vehicle for a heterologous nucleic acid molecule to protect canids from a disease for a variety of reasons, including, but not limited to, CHV's limited host range and pathogenicity. CHV, to the inventors' knowledge, has the most limited host range of any herpesvirus, including FHV, in that CHV's host range appears to be substantially limited to canine cells. As far as the inventors are aware, the only report of CHV infection of a cell type other than canine cells is limited infection of mink lung cells; see, for example, Peterson et al, 1988, *Comp. Immunol. Microbiol. Infect. Diseases* 11, 93–98. This limited host range illustrates the safety of CHV in that the virus apparently cannot be transmitted to a variety of species unrelated to canids.

Furthermore, CHV exhibits only limited pathogenicity. Although the virus has been shown to cause a fatal hemorrhagic disease in hypothermic neonatal pups (i.e., essentially all pups experimentally infected with CHV and maintained at room temperature (i.e., from about 25° C. to 27° C. ) within a week of birth die from the infection), CHV causes insignificant respiratory infection in adult dogs; see, for example, Carmichael, 1970, *J. Am. Vet. Med. Assn.* 156, 1714–1721. Moreover, prolonged survival or recovery of experimentally infected neonatal pups maintained at 38.4° C. to 39.5° C. was observed. Adult dogs exposed to CHV do, however, become infected since virus shedding has been shown to occur for at least two weeks post-inoculation; and latency is postulated to occur, since CHV has been isolated from primary cultured cells of normal healthy dogs; see, for example, Carmichael, ibid. Furthermore, maternal antibody, or passive transfer of antibody from seropositive dogs has been shown to protect puppies from an otherwise fatal CHV challenge; see, for example, Carmichael, ibid. Due to its limited pathogenicity, CHV apparently need not be attenuated to the extent required for other viruses used as live vaccine vectors. In addition, vaccination of a dam with CHV can lead to passive protection in her pups.

Another advantage of CHV is its limited temperature range. CHV grows well at temperatures ranging from about 34° C. to about 36° C., with optimal growth occurring at about 35° C. CHV, however, does not grow well at temperatures less than or equal to about 33° C. or at temperatures greater than or equal to about 37° C. As such CHV is significantly more temperature sensitive than any other known wild type herpes us, including FHV.

Yet another advantage of CHV is its potential for use as a single, multivalent therapeutic composition against a variety of canine pathogens. That is, the CHV genome can be manipulated to incorporate multiple heterologous nucleic acid molecules without disrupting the ability of the genome to be packaged (i.e., assembled) into a live virus. Examples of multivalent therapeutic compositions are described below.

As far as the inventors are aware, this application is the first report of the genetic engineering of a CHV genome, particularly for the development of efficacious canid vaccines, in spite of a long felt need for efficacious vaccines against canine pathogens. The inventors have developed methods to identify CHV genes and intergenic regions, particularly those having utility as targets for the insertion of heterologous nucleic acid molecules, despite the difficulty of using known herpesvirus sequences to identify such regions due to the AT-rich nature of the CHV genome. The CHV genome contains about 70% adenosine and thymidine residues, compared to other known herpesvirus genomes which, on the average, contain from about 30% to about 58% adenosine and thymidine residues (e.g., HSV, BHV, and PRV contain about 30%, EHV about 54%, and FHV about 58%, adenosine and thymidine residues). As such, it is very difficult to design primers or probes using known herpesvirus sequences to identify CHV analogs.

One embodiment of the present invention is a recombinant CHV. As used herein, a recombinant CHV is a CHV that comprises (i.e., has or includes) a genome that has been genetically engineered (i.e., subjected to recombinant nucleic acid (i.e., DNA or RNA) techniques, such as those disclosed in Sambrook et al., 1989, Molecular Cloning: A Laboratory Manual, Cold Spring Harbor Labs Press; Sambrook et al., ibid., is incorporated by reference herein in its entirety) to differ from the genome of a natural CHV isolate (i.e., a herpesvirus endogenous to the family Canidae). Such a genetically engineered genome is referred to herein as a recombinant CHV genome and is described in more detail below.

A recombinant CHV of the present invention includes not only a recombinant CHV genome but also an envelope and capsid in which the genome is packaged. The viral envelope and capsid are preferably a CHV envelope and a CHV capsid, encoded at least in part by CHV genes, thereby imparting to the recombinant CHV the host range of a natural CHV isolate. It is to be noted, however, that the present invention also includes recombinant CHV having envelopes and/or capsids that have been modified to, for example, alter (e.g., broaden, narrow, or completely change) the host range of the recombinant CHV genome. Such modifications can be accomplished by one skilled in the art by, for example, modifying CHV envelope and/or capsid genes and/or replacing such genes with those of another virus. Altered genes can be located on the CHV genome itself and/or in the genome of the cell in which the recombinant virus is produced.

A recombinant CHV genome of the present invention is a CHV genome in which nucleotides have been deleted, inserted, substituted or inverted using recombinant techniques known to those skilled in the art such that the recombinant CHV genome is no longer the same as a natural CHV genome. A recombinant CHV genome of the present invention is capable of effecting expression (e.g., transcription, translation) of coding regions that are operatively linked to regulatory sequences within the genome. As used herein, a coding region is a stretch of nucleotides that encodes an RNA molecule and/or a protein. Coding regions can be endogenous to CHV or can be heterologous nucleic acid molecules of the present invention, which are described in more detail below. The phrase operatively linked refers to the positioning of a coding region in the CHV genome such that the coding region is able to be expressed when the genome is inside a cell. Regulatory sequences include transcription control sequences, translation control sequences, and other regulatory sequences that control the expression of coding regions. Transcription control sequences are sequences which control the initiation, elongation, and termination of transcription. Particularly important transcription control sequences are those which control transcription initiation, such as promoter, enhancer, operator and repressor sequences. Suitable regulatory sequences include any regulatory sequence that can function in the present invention. Preferred regulatory sequences are disclosed herein.

A recombinant CHV genome of the present invention can include a gene that has been inactivated. As used herein, a gene includes a coding region as well as the regulatory sequences involved in expression of that coding region. An inactive gene refers to a gene that no longer exhibits the function of its natural counterpart. Methods to inactivate a gene include, but are not limited to, deletion of one or more nucleotides within the gene, insertion of one or more nucleotides into the gene, replacement of one or more nucleotides within the gene by other nucleotides (i.e., nucleotide substitution), and/or inversion of nucleotides within the gene such that the resulting gene no longer has the function of the corresponding natural gene. Such alterations can be effected anywhere within the gene, such as within the coding region, within the regulatory sequences and/or in regions surrounding the coding region or regulatory sequences such that the alteration(s) cause gene inactivation. In one embodiment, an entire gene or the coding region and/or regulatory sequences thereof can be deleted or replaced.

One embodiment of the present invention is an attenuated recombinant CHV. As used herein, an attenuated CHV is a CHV that does not cause 100% mortality if used to infect canid neonates less than 1 week old that are maintained in room temperature. A preferred attenuated CHV of the present invention causes less than about 90% and preferably less than about 70% mortality when used to infect canid neonates less than 1 week of age maintained at room temperature.

An attenuated recombinant CHV can be produced by inactivating a CHV gene that, due to that gene's inactivation, results in an attenuated virus. Methods to inactivate a gene are disclosed above. An attenuated CHV can be identified by exposing pups less than 1 week old to the recombinant virus to be tested and determining the percentage of exposed pups that die; such an exposure method is disclosed, for example, in Carmichael, ibid. If less than 100% percent of the pups die, the virus being tested is attenuated in accordance with the present invention. Suitable CHV genes to inactivate in order to produce an attenuated CHV include any gene that when inactivated leads to an attenuated virus, as determined using an assay as disclosed above. A preferred attenuated recombinant CHV of the present invention is a CHV having a recombinant genome in which a heterologous nucleic acid molecule is inserted into a gene, the insertion resulting in an attenuated virus.

An attenuated recombinant CHV has utility, for example, as a therapeutic composition to protect an animal from CHV infection and/or as a live CHV-based vaccine carrying a heterologous nucleic acid molecule. It is to be noted, however, that, as disclosed above, it is believed that CHV need not be attenuated for use as a live vaccine vector due to the low pathogenicity of natural CHV, particularly as compared to that of other herpesviruses.

One embodiment of the present invention is a recombinant CHV that can reproduce (i.e., grow) in tissue culture; that is, the virus is a reproduction competent CHV. A reproduction competent CHV is a CHV that upon in vitro infection of an appropriate host cell is able to use host cell machinery, as well as its own regulatory control regions and/or encoded enzymes, to effect self-reproduction, i.e., to form infectious virus.

Reproduction competent recombinant CHV genomes can have gene alterations in one or more genes non-essential for growth in vitro. Suitable gene targets (i.e., genes to alter) include any non-essential CHV gene. A non-essential CHV gene can be identified by altering a CHV gene within a CHV genome (e.g., by genetic engineering or classical mutagenesis) and demonstrating that the altered genome is capable of effecting self-reproduction in tissue culture. Preferred non-essential CHV genes to target include, but are not limited to, a CHV deoxyuridine triphosphate pyrophosphatase (CdUTPase) gene, a CHV glycoprotein C (CgC) gene, a CHV glycoprotein E (CgE) gene, a CHV glycoprotein G (CgG) gene, a CHV glycoprotein I (CgI) gene, a CHV serine-threonine protein kinase US3 (CPK) gene, a CHV thymidine kinase (CTK) gene, a CHV IR6 (CIR6) gene, a CHV US2 (CUS2) gene, a CHV tegument phosphoprotein US9 (CUS9) gene, a CHV membrane protein UL49 (CUL49) gene, a CHV membrane protein UL51 (CUL51) gene, and a CHV membrane protein UL45 (CUL45) gene. Particularly preferred non-essential genes to target include a CdUTPase gene, a CgC gene, a CgE gene, a CgG gene, a CgI gene, a CUS2 gene and a CUS9 gene. It is to be noted that CHV regions and genes disclosed herein are named in accordance with herpesvirus nomenclature in that the names include "C" for canine and the rest of the name indicating the corresponding herpes simplex virus (HSV) homolog (e.g., "dUTPase"). For example, the CHV unique short region (CUS) is the shorter region of the CHV genome that has unique sequences, analogous to the US region of HSV; the CHV unique long region (CUL) is the longer region of CHV that has unique sequences, analogous to the UL region of HSV; and the CHV inverted repeat regions (CIRs) are analogous to the HSV IR regions. CUS genes are CHV genes that are homologs of (i.e., genes that share some degree of similarity with) HSV genes located in the US region of the HSV genome. CUL genes are CHV genes that are homologs of HSV genes located in the UL region of the HSV genome. CIR genes are CHV genes that are homologs of HSV genes located in the IR regions of the HSV or EHV genome. It is also to be noted that although the UL, US, and IR designations refer to the respective genes' locations in the HSV genome, they do not necessarily refer to the respective genes' locations in the CHV genome. For example, while CUS2 is partially in the IR region of CHV, HSV US2 is entirely in the US region of HSV.

Another embodiment of the present invention is a recombinant CHV that is defective for reproduction in tissue culture. A reproduction defective CHV is a CHV that when inserted into an appropriate host cell is unable to form infectious virus. Such a defective CHV has at least one inactive gene that encodes a protein essential for reproduction, including, but not limited to proteins essential for viral entry, immediate early or early gene expression, DNA replication, capsid assembly, and viral egress. Suitable gene targets include any essential CHV gene, with preferred targets being genes encoding proteins involved in viral entry and/or egress. CHV defective in viral entry and/or egress are easy to complement and are advantageous over most other reproduction defective mutants in that such virus are able to undergo one round of viral replication. An essential CHV gene can be identified by altering a CHV gene within a CHV genome and demonstrating (a) that the altered genome is not capable of effecting self-reproduction in tissue culture under wild type conditions or, if a temperature sensitive mutant, at a nonpermissive temperature; and (b) that the altered genome can reproduce in a complementing cell line that expresses an active protein corresponding to the essential gene defect on the CHV genome (assuming the defect can be complemented in trans), or at a permissive temperature. Preferred essential CHV genes to target include, but are not limited to, a CHV glycoprotein D (CgD) gene, a CHV glycoprotein B (CgB) gene, a CHV alpha trans-inducing factor UL48 (CUL48) gene, and a CHV helicase/primase UL52 (CUL52) gene. Particularly preferred essential genes to target include a CgD gene and a CgB gene.

The present invention also includes cell lines that complement replication defective CHVs and use of such cell lines to produce replication defective viruses. As such, the present invention includes canine cell lines that complement, or supplement, a CHV defect in a gene encoding CgD, CgB, CUL48, and/or CUL52. Such cell lines can be produced by a variety of means known to those skilled in the art. For example, a cell capable of complementing a CgD negative, or CgD-, CHV (i.e., a virus with a CHV genome having an inactive CgD gene), can be produced by stable integration of an active CgD gene into the cellular genome or by co-transfection of the CgD- CHV with a nucleic acid molecule capable of complementing the defective CgD gene. Such a nucleic acid molecule can be a nucleic acid containing an active CgD gene operatively linked to regulatory sequences to enable expression of the CgD gene in the transfected cell. In another embodiment, such a nucleic acid molecule can be incorporated into a virus that is co-infected with the CgD- CHV. Such methods can also be used to produce cell lines complementing other replication defective CHVs of the present invention. Any canine cell line that CHV can infect and that expresses the complementary active protein can be used in the production of reproduction-defective CHV. Examples include, but are not limited to, the following cell lines available from American Type Culture Collection (ATCC), Rockville, Md.: ATCC CRL-1542 A-72 (Tumor, canine), ATCC CRL-1430 Cf2Th (Thymus, canine, Canis familiaris), ATCC CRL-10389 DH82 (Monocyte-macrophage, canine), ATCC CRL-8468 D17 (Osteogenic sarcoma, canine), ATCC CCL-183 D-17 (Primary osteogenic sarcoma, canine, Canis familiaris), ATCC CCL-34.1 DoCl1 (S+L-) (Kidney, canine, Canis familiaris), ATCC CCL-34 MDCK (NBL-2) (Kidney, canine, Canis familiaris), and ATCC CCL-34.2 MDCK/SF (Kidney, canine, Canis familiaris), such cell lines expressing, preferably in a stable manner, the desired essential gene(s) for complementation. Particularly preferred complementing cell lines include MDCK cells that stably express CgD, CgB, CUL48, and/or CUL52.

While not being bound by theory, it is believed that a a reproduction defective virus-based vaccine may be safer than a reproduction competent virus-based vaccine. On the other hand, a reproduction competent virus-based vaccine may be more efficacious than a reproduction defective virus-based vaccine. Since CHV, as disclosed above, exhibits low pathogenicity, a reproduction competent recombinant CHV is a preferred embodiment of the present invention.

As heretofore disclosed, one embodiment of the present invention is a recombinant CHV having one or more inactive genes. Preferred recombinant CHV of the present invention include genomes in which one or more of the following CHV genes have been inactivated, preferably using recombinant techniques: a CdUTPase gene, a CgC gene, a CgE gene, a CgG gene, a CgI gene, a CPK gene, a CTK gene, a CIR6 gene, a CUS2 gene, a CUS9 gene, a CUL49 gene, a CUL51 gene, a CUL45 gene, a CgD gene, a CgB gene, a CUL48 gene, and a CUL52 gene. Other than the genes encoding CgD, CgB, CUL48, and CUL52, the preferred genes to inactivate are nonessential genes. Each of the preferred genes to inactivate is a preferred target for the insertion of heterologous nucleic acid molecules; such insertion is a preferred method to inactivate these genes. More preferred recombinant CHV include genomes in which one or more of the following CHV genes have been inactivated, preferably using recombinant techniques: a CdUTPase gene, a CgC gene, a CgE gene, a CgG gene, a CgI gene, a CUS2 gene, a CUS9 gene, a CgD gene, and/or a CgB gene being more preferred. Also preferred are the corresponding recombinant CHV genomes.

Particularly preferred recombinant CHV of this embodiment include a CdUTPase negative CHV, a CgC negative CHV, a CgE negative CHV, a CgG negative CHV, a CgI negative CHV, a CPK negative CHV, a CTK negative CHV, a CIR6 negative CHV, a CUS2 negative CHV, a CUS9 negative CHV, a CUL49 negative CHV, a CUL51 negative CHV, a CUL45 negative CHV, a CgD negative CHV, a CgB negative CHV, a CUL48 negative CHV, and a CUL52 negative CHV. Particularly preferred recombinant CHV include a CdUTPase negative CHV, a CgC negative CHV, a CgE negative CHV, a CgG negative CHV, a CgI negative CHV, a CUS2 negative CHV, a CUS9 negative CHV, a CgD negative CHV, and a CgB negative CHV. Also preferred are the corresponding recombinant CHV genomes, as well as recombinant CHV and CHV genomes having more than one of these preferred genes inactivated. Examples of such CHV include, but are not limited to: a CUS2 negative, CdUTPase negative CHV; a CUS2 negative, CdUTPase negative, CgG negative CHV; and a CUS2 negative, CdUTPase negative, CgG negative, CgC negative CHV.

One embodiment of the present invention includes a recombinant CHV comprising a recombinant CHV genome comprising a heterologous nucleic acid molecule; i.e., the recombinant CHV genome includes one or more heterologous nucleic acid molecules located, or positioned , in the CHV genome. The present invention also includes a recombinant CHV genome having a heterologous nucleic acid molecule in the genome. Also included is the use of such a CHV and/or CHV genome as a therapeutic composition as well as in the production of a compound encoded by the heterologous nucleic acid molecule(s).

As used herein, a heterologous nucleic acid molecule is a nucleic acid molecule that is not derived from CHV; that is, a heterologous nucleic acid molecule is isolated from a source other than CHV. An isolated nucleic acid molecule of the present invention can be obtained from its natural source, can be produced using recombinant DNA technology (e.g., by amplification, such as by polymerase chain reaction (PCR) amplification and/or cloning) or can be produced by chemical synthesis.

In accordance with the present invention, a heterologous nucleic acid molecule can be inserted into a CHV genome simply to inactivate a CHV gene. A heterologous nucleic acid molecule can also be inserted into a CHV genome to serve as a target for the insertion of a second heterologous nucleic acid molecule, such as to introduce a restriction enzyme site or a recombination site otherwise not present in the CHV genome. For example, CHV strain D 004 (available from ATCC), which does not contain a Sse83871, I-Sce-I, or NotI restriction enzyme site, can be genetically engineered to include any or all of these sites by inserting into the genome a heterologous nucleic acid molecule containing a Sse83871, I-Sce-I, and/or NotI site(s). Such a heterologous nucleic acid molecule is a good target for the insertion of another heterologous nucleic acid molecule. Other restriction enzyme sites lacking in CHV can be identified using techniques known to those skilled in the art. Without being bound by theory, it is believed that CHV is more likely to lack GC-rich restriction enzyme sites than AT-rich sites, since the CHV genome is AT-rich, as disclosed above.

Another example of a heterologous nucleic acid molecule to insert into a CHV genome is a gene encoding a selectable marker, such as, but not limited to, an *E. coli* lacZ gene, a chloramphenicol transacetylase gene, a xanthine-guanine phosphoribosyl transferase gene, a β-glucuronidase gene, a neomycin resistance gene, an *E. coli* hygromycin resistance gene, and a heterologous thymidine kinase gene (e.g., HSV, FHV; assuming the CHV genome is a CTK negative genome). The presence of such a gene in a CHV genome allows for the selection of recombinant CHV having such a marker gene, and includes the ability to distinguish recombinant CHV from natural CHV isolates. In addition, a second heterologous nucleic acid molecule can be inserted into such a selectable marker gene, thereby inactivating the protein encoded by the marker gene, allowing for yet another method to select for CHV having a desirable heterologous nucleic acid molecule. Methods to select CHV having selectable marker genes, as well as for the inactivation of such markers, is known to those skilled in the art.

A preferred embodiment of the present invention is a recombinant CHV genome, and corresponding virus, in which the genome contains a heterologous nucleic acid molecule operatively linked to a transcription control sequence. As such, the heterologous nucleic acid molecule can be transcribed when transfected into a cell. A heterologous nucleic acid molecule can be joined to CHV transcription control sequences, can be joined to its own or other homologous transcription control sequences, and/or can be joined to transcription control sequences heterologous to both the heterologous nucleic acid molecule and CHV. The heterologous nucleic acid molecule can also be operatively linked to other regulatory sequences. Suitable regulatory sequences include any regulatory sequence that can function in the present invention. Preferred transcription control sequences include those sequences that can function in canine cells, including, but not limited to: mammalian, preferably canine; viral; or natural (i.e., endogenous to the heterologous nucleic acid molecule) transcription control sequences. Examples of transcription control sequences include antibiotic resistance gene, baculovirus, Heliothis zea insect virus, vaccinia virus, herpesvirus, poxvirus, adenovirus, simian virus 40, retrovirus, actin, Rous sarcoma virus, heat shock, and mammalian hormone transcription control sequences. Additional suitable transcription control sequences include tissue-specific promoters and enhancers as well as lymphokine-inducible promoters (e.g., promoters inducible by interferons or interleukins). In one embodiment, expression of a heterologous nucleic acid molecule inserted into a CHV genome is mediated, at least in part, by a human cytomegalovirus (CMV) immediate early promoter and a bovine growth hormone polyadenylation site.

A heterologous nucleic acid molecule of the present invention can be located in any region of the CHV genome (i.e., in the UL, US, and/or IR regions), including, but not limited to, in an essential gene, in a non-essential gene, or in an intergenic region. As such, a heterologous nucleic acid molecule can be located in a coding region, a regulatory region, an intron, an untranslated region, or a non-transcribed region of a gene. A heterologous nucleic acid molecule can also be located in a direct or inverted repeat, including direct and/or inverted repeats within the IR, US or UL regions of CHV. For example, a heterologous nucleic acid molecule can be located in one or more CHV origins of replication (Cori), such as in CoriS.

In one embodiment, a heterologous nucleic acid molecule is located in a CHV genome such that a gene is inactivated. Suitable and preferred gene targets are as disclosed above, with non-essential gene targets being preferred.

In another embodiment, a heterologous nucleic acid molecule is located in a region of the CHV genome spanning from about the 3' end of the coding region of the CUL41 gene through about the 3' end of the coding region of the CUL38 gene. CUL41 gene refers to the CHV homolog of the HSV virion host shutoff protein UL41 gene. CUL38 gene refers to the CHV homolog of the HSV capsid protein VP19C UL38 gene. In most herpesviruses analyzed by cloning and sequencing techniques to date, the region between UL41 and UL38 contains genes encoding the large and small subunits of ribonucleotide reductase. The inventors have found, however, that the ribonucleotide reductase genes appear to be at least partially deleted in CHV in such a manner that there is an intergenic target in that region for heterologous nucleic acid molecule insertion.

A preferred recombinant CHV genome of the present invention comprises a heterologous nucleic acid molecule located in a region of the genome such that the heterologous nucleic acid molecule-containing CHV genome can be easily distinguished from a CHV genome not containing the heterologous nucleic acid molecule; that is, the heterologous nucleic acid molecule is inserted into a selectable region of the genome. Suitable selectable regions include any region of the CHV genome that, upon introduction of a heterologous nucleic acid molecule, leads to a detectable (e.g., growth-related, biochemical, or molecular) change in the CHV genome or CHV containing the genome. Examples of such selectable regions include, but are not limited to, a CTK gene and a CdUTPase gene. CHV genomes in which a heterologous nucleic acid molecule is inserted into a CTK gene or a CdUTPase gene can be selected using methods known to those skilled in the art; see for example, Kit et al, 1983, Virology 130, 381–389; and Holliday et al, 1991, Antiviral Research 16, 197–203.

Additional examples of selectable regions include restriction endonuclease sites, such as the HindIII site or XbaI site in the CdUTPase gene and the AscI site in the CUS2 gene. The AscI site is particularly preferred as there are no other AscI sites in the CHV genome. As such, a particularly preferred CHV of the present invention is a recombinant CHV having a CHV genome including a heterologous nucleic acid molecule in an AscI site in the CHV genome. Even more preferred is recombinant CHV strain D 004 having a heterologous nucleic acid molecule in an AscI site in the CHV genome. Also preferred are the corresponding genomes. Examples of methods to insert a heterologous nucleic acid molecule into a genome, including into restriction endonuclease site(s) in the genome, are disclosed herein. Such methods are known to those skilled in the art.

One embodiment of the present invention is a recombinant CHV genome having a heterologous nucleic acid molecule in one of the following regions of the CHV genome: a region spanning the 9,300 nucleotide AscI restriction endonuclease fragment, denoted herein as $nCAsc_{9300}$, that apparently includes the entire US region; a region spanning the 10,000 nucleotide fragment from AscI to the end of the genome, denoted herein as $nCAsc_{10000}$, that apparently essentially comprises an IR region, including the CIR6 gene; a region spanning the 3,000 nucleotide HindIII fragment, denoted herein as $nCHin_{3000}$, that spans from a portion of CUL48 through a portion of the CdUTPase gene; and/or a region spanning the 1,900 nucleotide HindIII fragment, denoted herein as $nCHin_{1900}$, that includes the remainder of the CdUTPase gene through a portion of CUL52. Details regarding the production of these and certain other nucleic acid molecules of the present invention are provided in the Examples section.

Also included in the present invention is a recombinant CHV genome having a heterologous nucleic acid molecule in a region of the genome spanning at least one of the following: a CHV US region comprising $nCUS_{5495}$, a CHV UL region comprising $nCgC/CUL45_{2100}$, a CgE gene comprising $nCgE_{750}$, a CgI gene comprising $nCgI_{161}$, a CUS9 gene comprising $nCUS9_{579}$, a CHV UL region comprising $nCdUTP/CUL51_{743}$, a CTK gene comprising $nCTK_{280}$, a CUL48 gene comprising $nCUL48_{294}$, a CUL49 gene included in $nCHin_{3000}$, a CUL52 gene comprising $nCUL52_{1461}$ as well as allelic variants of such (i.e., said, any of these) regions. As such, the present invention also includes a recombinant CHV genome having a heterologous nucleic acid molecule in a region of the genome spanning at least one of the following: a CIR6 gene including $nCIR6_{552}$, a CUS2 gene including $nCUS2_{1176}$, a CPK gene including $nCPK_{1203}$, a CgG gene including $nCgG_{1248}$, a CgD gene including $nCgD_{357}$, a CdUTPase gene including $nCdUTP_{459}$, and a CUL51 gene including $nCUL51_{261}$, as well as allelic variants of such regions.

As used herein, an allelic variant of a nucleic acid molecule, or region, for which nucleic acid sequence is provided herein is a nucleic acid molecule, or region, that occurs at essentially the same locus in another CHV genome as the nucleic acid molecule in CHV strain D 004, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions. Allelic variants are well known to those skilled in the art and would be expected to be found among the family of canine herpesviruses.

The present invention also includes a recombinant CHV genome having a heterologous nucleic acid molecule in a region of the genome spanning at least one of the following nucleic acid molecules: $nCUS_{5495}$ (and, as such, $nCIR6_{552}$, $nCUS2_{1176}$, $nCPK_{1203}$, $nCgG_{1248}$, and/or $nCgD_{357}$), $nCgC/CUL45_{2100}$, $nCgE_{750}$, $nCgI_{161}$, $nCUS9_{579}$, $nCdUTP/CUL51_{743}$ (and, as such, $nCdUTP_{459}$ and $nCUL51_{261}$), $nCTK_{280}$, $nCUL48_{294}$, and/or $nCUL52_{146}$, as well as allelic variants of such regions.

A particularly preferred CHV genome of the present invention includes a heterologous nucleic acid molecule located in a region of the CHV genome comprising (e.g., including, represented by, or identified by) at least one of the following nucleic acid sequences: SEQ ID NO:1, SEQ ID NO:2, SEQ ID NO:3, SEQ ID NO:5, SEQ ID NO:7, SEQ ID NO:9, SEQ ID NO:11, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, and/or SEQ ID NO:38, as well as allelic variants of such regions. The relationships between certain nucleic acid molecules and nucleic acid sequences of the present invention are detailed below. It should be noted that since nucleic acid sequencing technology is not entirely error-free, the sequences represented by the SEQ ID NOs in the present invention at best represent apparent nucleic acid or amino acid sequences of CHV nucleic acid molecules or proteins of the present invention. It is also to be noted that a double-stranded nucleic acid molecule of the present invention for which a nucleic acid sequence has been determined for one strand that is represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

The present invention includes a recombinant CHV genome that includes a heterologous nucleic acid molecule that encodes a protective compound; the present invention also includes a recombinant CHV containing such a genome. As used herein, a protective compound is a compound that when administered to an animal protects that animal from a disease corresponding to that compound. For example, a compound derived from *Dirofilaria immitis* protects an animal from heartworm and other related infections, whereas a compound derived from a virus protects an animal from disease caused by that and related viruses. As used herein, the ability of a compound to protect an animal from a disease refers to the ability of that protective compound to treat, ameliorate and/or prevent the disease.

A protective compound of the present invention includes, but is not limited to, a protective protein and a protective RNA species. Essentially any heterologous nucleic acid molecule that encodes a protective protein or RNA can be used in the present invention. A protective protein of the present invention can be, for example, an immunogen that elicits an immune response which will protect an animal from the corresponding disease or some other compound (e.g., an immunomodulator, a toxin, an enzyme, an antibody, or other binding protein) that neutralizes and/or reduces the disease. A protective RNA of the present invention can be, for example, an RNA-based drug, a ribozyme, a molecule capable of triple helix formation, or an antisense RNA that effectively prevents the expression of a detrimental protein, thereby protecting an animal from disease.

It is within the scope of the present invention to produce therapeutic compositions against a variety of diseases, including infectious diseases, genetic diseases, and other metabolic diseases, including diseases that lead to abnormal cell growth, degenerative processes, and/or immunological defects. Therapeutic compositions of the present invention can protect animals from a variety of diseases including, but not limited to, allergies, autoimmune diseases, cancers, cardiovascular diseases, graft rejection, hematopoietic disorders, immunodeficiency diseases, immunoproliferative diseases, immunosuppressive disorders, infectious diseases, inflammatory diseases, jaundice, septic shock, other immunological defects, as well as other genetic or metabolic defects.

One preferred embodiment of the present invention is a recombinant CHV having a heterologous nucleic acid molecule within its genome that encodes a compound that protects a canid, or other animal susceptible to CHV infection, from infectious disease. Such disease can be caused by a variety of infectious agents, including, but not limited to, helminth parasites, protozoan parasites, ectoparasites, fungi (including yeast), bacteria and/or viruses. It should also be noted that although some infectious agents have not been definitively classified into one of these groups, such infectious agents are also included in the present invention. A preferred protective compound is derived from (e.g., obtained from natural source or produced using recombinant or synthetic chemistry techniques) an infectious agent.

Preferred helminth infectious agents to target include nematodes, cestodes and trematodes, with filariid, ascarid, capillarid, strongylid, strongyloides, trichostrongyle, and trichurid, parasitic helminths being more preferred, and filariid nematodes being even more preferred. More preferred parasitic helminths to target include the following: Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria (e.g., *D. immitis*), Dracunculus, Echinococcus, Enterobius, Filaroides, Haemonchus, Loa, Mansonella, Muellerius, Nanophyetus, Necator, Nematodirus, oesophagostomum, Onchocerca, Opisthorchis, Ostertagia, Parafilaria, Paragonimus, Parascaris, Physaloptera, Protostrongylus, Setaria, Spirometra, Spirocera, Stephanofilaria, Strongyloides, Strongylus, Taenia, Thelazia, Toxascaris, Toxocara, Trichinella, Trichostrongylus, Trichuris, Uncinaria, and Wuchereria. More preferred helminths to target, particularly with respect to being canine pathogens include Ancylostoma, Angiostrongylus, Brugia, Capillaria, Crenosoma, Dioctophyme, Dipetalonema, Diphyllobothrium, Diplydium, Dirofilaria, Echinococcus, Filaroides, Nanophyetus, Opisthorchis, Paragonimus, Physaloptera, Spirometra, Spirocera, Strongyloides, Taenia, Toxascaris, Toxocara, Trichinella, Trichuris, and Uncinaria.

Preferred protozoal infectious agents to target include Acetospora, Apicoplexa, Ciliophora, Labyrinthomorphorpha, Microspora, Myxozoa and Sarcomastigophora, with Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, being more preferred. More preferred protozoans to target, particularly with respect to being canine pathogens, include Babesia, Balantidium, Besnoitia, Cryptosporidium, Encephalitozoon, Entamoeba, Giardia, Hammondia, Hepatozoon, Isospora, Leishmania, Microsporidia, Neospora, Pentatrichomonas, Pneumocystis, Sarcocystis, Schistosoma, Toxoplasma, and Trypanosoma.

Preferred ectoparasite infectious agents to target include fleas, flies, mosquitoes, ticks, mites, lice, spiders, ants and true bugs, with fleas being more preferred. More preferred are fleas of the genera Ctenocephalides, Ctopsyllus, Diamanus, Echidnophaga Nosopsyllus, Pulex, Tunga, and Xenopsylla, with *Ctenocephalides canis* and *Ctenocephalides felis* fleas being particularly preferred.

Preferred fungal agents include Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha.

Preferred bacterial infectious agents to target include Actinomyces, Bacillus, Bacteroides, Bordetella, Bartonella (e.g., *B. henselae*), Borrelia (e.g., *B. burgdorferi*), Brucella, Campylobacter, Capnocytophaga, Clostridium, Corynebacterium, Coxiella, Dermatophilus, Enterococcus, Ehrlichia (e.g., *E. canis*), Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia (e.g., *Y. pestis*).

Preferred virus infectious agents to target include adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses.

A preferred recombinant CHV of the present invention includes a recombinant CHV genome having a heterologous nucleic acid molecule encoding a protective compound that elicits an immune response. As used herein, a protective compound that elicits an immune response refers to a compound that when administered to an animal in an appropriate manner, known to those skilled in the art, leads to the production of an immune response in that animal against the protective compound. The immune response, which can include humoral and/or cell-mediated components, preferably protects the immunized animal against the disease(s) targeted by the protective compound. As such, preferred protective compounds include, but are not limited to, antigens associated with diseases, as disclosed herein. Particularly preferred protective compounds of the present invention include *Dirofilaria immitis* antigens, *Toxoplasma gondii* antigens, Sarcocystis antigens, *Bartonella henselae* antigens, *Yersinia pestis* antigens, flea antigens, flea allergens, viral antigens, and cancer antigens. Even more preferred protective compounds are those disclosed in the following patent applications and patent publications, which are incorporated by reference herein in their entireties: U.S. Pat. No. 5,356,622, issued Oct. 18, 1994; U.S. Pat. No. 5,399,485, issued Mar. 21, 1995; U.S. Pat. No. 5,418,137, issued May 23, 1995; PCT Publication No. WO 92/13560, published Aug. 20, 1992; PCT Publication No. WO 93/10225, published May 27, 1993; PCT Publication No. WO 93/23077, published Nov. 25, 1993; PCT Publication No. WO 94/15593, published Jul. 21, 1994; PCT Publication No. WO 94/17813, published Aug. 18, 1994; PCT Publication No. WO 94/17824, published Aug. 18, 1994; PCT Publication No. WO 95/24198, published Sep. 14, 1995; PCT Publication No. WO 95/32988, published Dec. 7, 1995; U.S. Ser. No. 08/401,509, filed Mar. 9, 1995; U.S. Ser. No. 08/415,365, filed Mar. 30, 1995; U.S. Ser. No. 08/450,944, filed May 23, 1995; U.S. Ser. No. 08/473,034, filed Jun. 6, 1995; U.S. Ser. No. 08/482,304, filed Jun. 7, 1995; U.S. Ser. No. 08/485,434, filed Jun. 7, 1995; U.S. Ser. No. 08/486,036, filed Jun. 7, 1995; U.S. Ser. No. 08/558,735 filed Nov. 16, 1995; PCT Ser. No. PCT/US95/13200, filed Oct. 6, 1995; PCT Ser. No. PCT/US95/14442, filed Oct. 18, 1995; and related filings.

Another preferred protective compound of the present invention is an immunomodulator. Suitable immunomodulators include compounds that enhance the immune response as well as compounds that suppress the immune response. Compounds that enhance the immune response include compounds that preferentially enhance humoral immunity as well as compounds that preferentially enhance cell-mediated immunity. Suitable compounds can be selected depending on the disease being targeted. Suitable immunomodulators include, but are not limited to, cytokines, chemokines, superantigens, and other immunomodulators as well as compounds that induce the production of cytokines, chemokines and other immunomodulators. Examples of such protective compounds include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), and Leishmania elongation initiating factor (LEIF).

One preferred embodiment of the present invention is a recombinant CHV having more than one heterologous nucleic acid molecule included in the CHV genome. Such a CHV can include two or more heterologous nucleic acid molecules encoding two or more protective compounds to protect an animal from a given disease (e.g., two or more heartworm antigens), or can include two or more heterologous nucleic acid molecules encoding protective compounds each targeted against a different disease (e.g., a compound to protect an animal against heartworm and a compound to protect an animals against a viral infection). A preferred multivalent CHV can also include an heterologous nucleic acid molecule encoding a protective compound that elicits an immune response as well as an heterologous nucleic acid molecule encoding an immunomodulator to enhance the desired immune response. Also included in the present invention are protective compounds that are fusion, or multivalent, proteins comprising more than one functional domain.

The present invention also includes recombinant CHV genomes. As such, the invention includes any CHV genome disclosed herein, including those included in recombinant CHV of the present invention. Also included in the present invention are cells comprising recombinant CHV genomes of the present invention. As used herein, a cell comprising a recombinant CHV genome is a cell into which a recombinant CHV genome has been introduced. Such introduction can be accomplished by any method by which a nucleic acid molecule can be inserted into a cell. Such methods, known to those skilled in the art, include, but are not limited to, infection (i.e., with a virus comprising the genome), transfection, transformation, electroporation, microinjection, lipofection, adsorption, and protoplast fusion. A preferred cell comprises a recombinant CHV having a heterologous nucleic acid molecule, which preferably is operatively linked to a transcription control sequence. Cells containing CHV genomes are useful in the production of recombinant CHV. Methods to produce recombinant CHV are disclosed herein.

The present invention also includes isolated CHV nucleic acid molecules. As used herein, a CHV nucleic acid molecule is a nucleic acid molecule that is derived from CHV. As such, the nucleic acid molecule can be produced, for example, by recovery of such a nucleic acid molecule directly from a CHV genome, by recombinant DNA techniques, or by chemical synthesis. That the CHV nucleic acid molecule is isolated indicates that the molecule is removed from its natural milieu. An isolated CHV nucleic acid molecule can include DNA, RNA, or derivatives of either DNA or RNA.

A preferred CHV nucleic acid molecule of the present invention is a CHV nucleic acid molecule that hybridizes under stringent hybridization conditions with at least one of the following: with a CdUTPase gene, a CgC gene, a CgE gene, a CgG gene, a CgI gene, a CPK gene, a CTK gene, a CIR6 gene, a CUS2 gene, a CUS9 gene, a CUL49 gene, a CUL51 gene, a CUL45 gene, a CgD gene, a CUL48 gene, and/or a CUL52 gene; with other regions of a CUS; and/or with a region of the CHV genome spanning from about the 3' end of the coding region of the CUL41 gene through about the 3' end of the coding region of the CUL38 gene. The identifying characteristics of such regions, including the CHV genes listed, are heretofore described.

As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Formulae to calculate the appropriate hybridization and wash conditions to achieve hybridization permitting 30% or less mis-match between two nucleic acid molecules are disclosed, for example, in Meinkoth et al, 1984, *Anal. Biochem* 138, 267–284; Meinkoth et al, ibid, is incorporated by reference herein in its entirety. An example of such conditions includes, but is not limited to, the following: Oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 2X SSPE, 1% Sarkosyl, 5X Denhardts and 0.1 mg/ml denatured salmon sperm DNA at a temperature as calculated using the formulae of Meinkoth et al., ibid. for about 2 to about 12 hours. The filters are then washed 3 times in a wash solution containing 2X SSPE, 1% Sarkosyl at about 55° C. for about 15 minutes each. The filters can be further washed in a wash solution containing 2X SSPE, 1% Sarkosyl at about 55° C. for about 15 minutes per wash.

A CHV nucleic acid molecule of the present invention can include an isolated natural CHV gene or a homolog thereof, the latter of which is described in more detail below. A CHV nucleic acid molecule of the present invention can include one or more regulatory regions, full-length or partial coding regions, or combinations thereof. The minimal size of a CHV nucleic acid molecule of the present invention is the minimal size that can form a stable hybrid with one of the aforementioned CHV genes and other regions under stringent hybridization conditions.

Isolated CHV nucleic acid molecules include natural nucleic acid molecules and homologs thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a CHV protein of the present invention or to form stable hybrids under stringent conditions with natural gene isolates.

A CHV nucleic acid molecule homolog can be produced using a number of methods known to those skilled in the art (see, for example, Sambrook et al., ibid.). CHV nucleic acid molecule homologs can be selected from a mixture of modified nucleic acids by screening for the function of the protein encoded by the nucleic acid molecule and/or by hybridization with a CHV region as defined above.

An isolated CHV nucleic acid molecule of the present invention can include a nucleic acid sequence that encodes at least one CHV protein of the present invention; such proteins are discussed in further detail below. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a CHV protein.

One embodiment of the present invention is a CHV nucleic acid molecule that, when administered to an animal, is capable of protecting that animal from CHV infection. Such a CHV nucleic acid molecule can be, or encode, an antisense RNA, a molecule capable of triple helix formation, a ribozyme, or other nucleic acid-based drug compound. In an additional embodiment, a CHV nucleic acid molecule of the present invention can encode a protective protein, the nucleic acid molecule being delivered to the animal by direct injection (i.e. as a naked nucleic acid) or in a vehicle such as a recombinant virus vaccine or a recombinant cell vaccine.

One embodiment of the present invention is a CHV nucleic acid molecule that hybridizes under stringent hybridization conditions with $nCUS_{5495}$, $CgC/CUL45_{2100}$, $nCgE_{750}$, $nCgI_{161}$, $nCUS9_{579}$, $nCdUTP/CUL51_{1743}$, $nCTK_{280}$, $nCUL48_{294}$, a $nCUL49$ included in $nCHin_{3000}$, and/or $nCUL52_{146}$. Such a CHV nucleic acid molecule can also hybridize under stringent hybridization conditions with $nCAsc_{9300}$, $nCAsc_{10000}$, $nCHin_{3000}$, $nCHin_{1900}$, $nCIR6_{552}$, $nCUS2_{1176}$, $nCPK_{1203}$, $nCgG_{1248}$, $nCgD_{357}$, $nCdUTP_{459}$, $nCTK_{279}$, $nCUS9_{450}$, $nCUL48_{291}$, $nCUL51_{261}$, $nCUL52_{144}$, and/or $nCgI_{159}$. At least some of such CHV nucleic acid molecules can hybridize under stringent hybridization conditions with a nucleic acid molecule having nucleic acid sequence SEQ ID NO:1, SEQ ID NO:2, SEQ ID NO:13, SEQ ID NO:14, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:35, and/or SEQ ID NO:37.

SEQ ID NO:1 and SEQ ID NO:2 represent the deduced nucleic acid sequences of the two complementary strands of $nCUS_{5495}$. Translation of SEQ ID NO:1 and SEQ ID NO:2 indicates that nucleic acid molecule $nCUS_{5495}$ encodes CIR6, CUS2, CPK and CgG proteins as well as a portion of a CgD protein. Specifically, SEQ ID NO:2 includes: a coding region for a CIR6 protein of about 183 amino acids, denoted herein as $nCIR6_{552}$ and represented by SEQ ID NO:3, assuming a start codon spanning about nucleotides 4566–4568 and a stop codon spanning about nucleotides 5115–5117 of SEQ ID NO:2; and a coding region for a CUS2 protein of about 391 amino acids, denoted herein as $nCUS2_{1176}$ and represented by SEQ ID NO:5, assuming a start codon spanning about nucleotides 3232–3234 and a stop codon spanning about nucleotides 4405–4407 of SEQ ID NO:2. The amino acid sequences of the respective encoded proteins $PCIR6_{183}$ and $PCUS2_{391}$ are represented by SEQ ID NO:4 and SEQ ID NO:6. SEQ ID NO:1 includes: a coding region for a CPK protein of about 400 amino acids, denoted herein as $nCPK_{1203}$ and represented by SEQ ID NO:7, assuming a start codon spanning about nucleotides 2384–2386 and a stop codon spanning about nucleotides 3584–3586 of SEQ ID NO:1; a coding region for a CgG protein of about 415 amino acids, denoted herein as $nCgG_{1248}$ and represented by SEQ ID NO:9, assuming a start codon spanning about nucleotides 3698–3700 and a stop codon spanning about nucleotides 4943–4945 of SEQ ID NO:1; and a partial coding region for a CgD protein of about 119 amino acids, denoted herein as $nCgD_{357}$ and represented by SEQ ID NO:11, assuming a start codon spanning about nucleotides 5137–5139. The amino acid sequences of the respective encoded proteins $PCPK_{400}$, $PCgG_{415}$, and $PCgD_{119}$ are represented by SEQ ID NO:8, SEQ ID NO:10 and SEQ ID NO:12.

SEQ ID NO:13 and SEQ ID NO:14 represent the deduced nucleic acid sequences of the two complementary strands of $nCdUTP/CUL51_{743}$. SEQ ID NO:13 includes a partial coding region for a CdUTPase protein of about 152 amino acids, denoted herein as $nCdUTP_{459}$ and represented by SEQ ID NO:15, assuming a first in-frame codon spanning about nucleotides 3–5, and a stop codon spanning about nucleotides 459–461 of SEQ ID NO:13. The amino acid sequence of the encoded protein $PCdUTP_{152}$ is represented by SEQ ID NO:16. SEQ ID NO:14 includes a partial coding region for a CUL51 protein of about 86 amino acids, denoted herein as $nCUL51_{261}$ and represented by SEQ ID NO:33, assuming a first in-frame codon spanning about nucleotides 1–3, and a stop codon spanning about nucleotides 259–261 of SEQ ID NO:14. The amino acid sequence of the encoded protein PCUL5186 is represented by SEQ ID NO:34.

SEQ ID NO:17 and SEQ ID NO:19 represent the deduced nucleic acid sequences of the two complementary strands of $nCUS9_{579}$. SEQ ID NO:17 includes a coding region for a CUS9 protein of about 149 amino acids, denoted herein as $nCUS9_{450}$ and represented by SEQ ID NO:20, assuming a start codon spanning about nucleotides 54–56 and a stop codon spanning about nucleotides 501–503 of SEQ ID NO:17. The amino acid sequence of the encoded protein $PCUS9_{149}$ is represented by SEQ ID NO:18.

SEQ ID NO:21 and SEQ ID NO:23 represent the deduced nucleic acid sequences of the two complementary strands of $nCUL48_{294}$. SEQ ID NO:21 includes a partial coding region for a CUL48 protein of about 97 amino acids, denoted herein as $nCUL48_{291}$ and represented by SEQ ID NO:24, assuming a first in-frame codon spanning about nucleotides 3–5 of SEQ ID NO:21. The amino acid sequence of the encoded protein $PCUL48_{97}$ is represented by SEQ ID NO:22.

SEQ ID NO:25 and SEQ ID NO:27 represent the deduced nucleic acid sequences of the two complementary strands of $nCUL52_{146}$. SEQ ID NO:25 includes a partial coding region for a CUL52 protein of about 48 amino acids, denoted herein as $nCUL52_{144}$ and represented by SEQ ID NO:28, assuming a first in-frame codon spanning about nucleotides 1–3 of SEQ ID NO:25. The amino acid sequence of the encoded protein $PCUL52_{48}$ is represented by SEQ ID NO:26.

SEQ ID NO:29 and SEQ ID NO:31 represent the deduced nucleic acid sequences of the two complementary strands of $nCgI_{161}$. SEQ ID NO:29 includes a partial coding region for a CgI protein of about 53 amino acids, denoted herein as $nCgI_{159}$ and represented by SEQ ID NO:32, assuming a first in-frame codon spanning about nucleotides 3–5 of SEQ ID NO:29. The amino acid sequence of the encoded protein $PCgI_{53}$ is represented by SEQ ID NO:30.

SEQ ID NO:35 and SEQ ID NO:37 represent the deduced nucleic acid sequences of the two complementary strands of $nCTK_{280}$. SEQ ID NO:35 includes a partial coding region for a CTK protein of about 93 amino acids, denoted herein as $nCTK_{279}$ and represented by SEQ ID NO:38, assuming a first in-frame codon spanning about nucleotides 2–4 of SEQ ID NO:35. The amino acid sequence of the encoded protein $PCTK_{93}$ is represented by SEQ ID NO:36.

Comparison of the CHV nucleic acid sequences SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, and SEQ ID NO:38 with known sequences indicates that none of these CHV nucleic acid sequences share more than about 70% identity (many, if not all, sharing significantly less identity) with a known nucleic acid sequence. As such, a preferred CHV nucleic acid molecule has a nucleic acid sequence that is at least about 80%, preferably at least about 85%, more preferably at least about 90%, even more preferably at least about 95%, and even more preferably at least about 99% identical to nucleic acid sequence SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, and/or SEQ ID NO:38.

A more preferred CHV nucleic acid molecule of the present invention includes at least a portion of CHV nucleic acid molecule $nCAsc_{9300}$, $nCAsc_{10000}$ io $nCHin_{3000}$, $nCHin_{1900}$, $nCUS_{5495}$, $nCIR6_{552}$, $nCUS2_{1176}$, $nCPK_{1203}$, $nCgG_{1248}$, $nCdUTP/CUL51_{743}$, $nCdUTP_{459}$, $nCUS9_{579}$, $nCUS9_{450}$, $nCUL48_{294}$, $nCUL48_{291}$, $nCUL52_{146}$, $nCUL52_{144}$, $nCgI_{161}$, $nCgI_{159}$, $nCgE_{750}$, $nCTK_{280}$, $nCTK_{279}$, and/or $nCUL51_{261}$, as well as allelic variants of those CHV nucleic acid molecules. Such CHV nucleic acid molecules can include nucleotides in addition to those included in the defined fragments; examples of such CHV nucleic acid molecules include full-length genes, full-length coding regions, or nucleic acid molecules encoding multivalent proteins. Particularly preferred CHV nucleic acid molecules are $nCAsc_{9300}$ $nCAsc_{10000}$, $nCHin_{3000}$ $nCHin_{1900}$, $nCUS_{5495}$, $nCIR6_{552}$, $nCUS2_{1176}$, $nCPK_{1203}$, $nCgG_{1248}$, $nCdUTP/CUL51_{743}$, $nCdUTP_{459}$, $nCUS9_{579}$, $CUS9_{450}$, $nCUL48_{294}$, $nCUL48_{291}$, $nCUL52_{146}$, $nCUL52_{144}$, $nCgI_{161}$, $nCgI_{159}$, $nCgE_{750}$, $nCTK_{280}$, $nCTK_{279}$, and/or $nCUL51_{261}$.

Similarly, a preferred CHV nucleic acid molecule of the present invention includes at least a portion of nucleic acid sequence SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, and/or SEQ ID NO:38; or a complement of SEQ ID NO:3, SEQ ID NO:5, SEQ ID NO:7, SEQ ID NO:9, SEQ ID NO:15, SEQ ID NO:20,NSEQ ID NO:24, SEQ ID NO:28, SEQ ID NO:32, SEQ ID NO:33, and/or SEQ ID NO:38; as well as allelic variants of such nucleic acid molecules. More preferred is a nucleic acid molecule that includes at least one of the following nucleic acid sequences: SEQ ID NO:1, SEQ ID NO:2, SEQ ID NO:3, SEQ ID NO:5, SEQ ID NO:7, SEQ ID NO:9, SEQ ID NO;13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, and/or SEQ ID NO:38; or a complement of SEQ ID NO:3, SEQ ID NO:5, SEQ ID NO:7, SEQ ID NO:9, SEQ ID NO:15, SEQ ID NO:20, SEQ ID NO:24, SEQ ID NO:28, SEQ ID NO:32, SEQ ID NO:33, and/or SEQ ID NO:38; also included are nucleic acid molecules that are allelic variants of nucleic acid molecules having those nucleic acid sequences. Such nucleic acid molecules can include nucleotides in addition to those included in the SEQ ID NOs.

The present invention also includes CHV nucleic acid molecules encoding a protein, including nucleic acid molecules that have been modified to accommodate codon usage properties of the cells in which such nucleic acid molecules are to be expressed. CHV proteins of the present invention are described in more detail below.

The present invention also includes CHV nucleic acid molecules that are oligonucleotides capable of hybridizing, under stringent hybridization conditions, with complementary regions of other, preferably longer, CHV nucleic acid molecules of the present invention. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit CHV infection as disclosed herein.

The present invention also includes an isolated CHV protein encoded by a CHV nucleic acid molecule of the present invention. As such, the present invention includes a CHV protein encoded by a CHV nucleic acid molecule that hybridizes under stringent hybridization conditions with at least one of the following: a CdUTPase gene, a cgc gene, a CgE gene, a CgG gene, a CgI gene, a CPK gene, a CTK gene, a CIR6 gene, a CUS2 gene, a CUS9 gene, a CUL49 gene, a CUL51 gene, a CUL45 gene, a CgD gene, a CUL48 gene, and/or a CUL52 gene; and/or with other portions of a CUS region.

According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis. As used herein, a CHV protein can be a full-length protein or any homolog of such a protein. Examples of CHV homologs include CHV proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog retains a desired activity of the natural protein, such as, but not limited to, enzymatic activity, activity important for viral growth, and/or ability to elicit an immune response. These activities can be measured using techniques known to those skilled in the art.

CHV protein homologs can be the result of natural allelic variation or natural mutation. CHV protein homologs of the present invention can also be produced using techniques known in the art including, but not limited to, direct modifications to the protein or modifications to the gene encoding the protein using, for example, classic or recombinant DNA techniques to effect random or targeted mutagenesis.

The minimal size of a CHV protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a CHV protein homolog of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a CHV protein homolog of the present invention is from about 4 to about 6 amino acids in length, with preferred sizes depending on whether full-length, fusion, or other functional portions of such proteins are desired.

One embodiment of the present invention is a CHV protein that can protect an animal from disease, preferably by eliciting an immune response against CHV, and/or can detect CHV infection in an animal. The minimum size of such a protein is a minimum size sufficient to form an epitope, a size that typically is at least from about 5 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

The present invention also includes mimetopes of CHV proteins that can be used in accordance with methods as disclosed for CHV proteins of the present invention. As used herein, a mimetope of a CHV protein of the present invention refers to any compound that is able to mimic the activity of such a CHV protein, often because the mimetope has a structure that mimics the CHV protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of the present invention is a fusion, or multivalent, protein that includes a CHV protein-containing domain attached to another functional domain. Such a domain can be an entire protein, or function portion thereof. Examples of such domains include not only protective compounds as disclosed above, but also domains that enhance a protein's stability (e.g., during production, storage and/or use) or that aid in protein purification.

A preferred isolated protein of the present invention is a protein encoded by a nucleic acid molecule that hybridizes under stringent hybridization conditions with $nCIR6_{552}$, $nCUS2_{1176}$, $nCPK_{1203}$, $nCgG_{1248}$, $nCgD_{357}$, $nCgC/CUL45_{2100}$, $nCdUTP_{459}$, $nCUS9_{450}$, $nCUL48_{291}$, $nCUL52_{144}$, $nCgI_{159}$, $nCgE_{750}$, $nCTK_{279}$, and/or $nCUL51_{261}$. Also included is a protein that hybridizes under stringent hybridization conditions with $nCAsc_{9300}$, $nCAsc_{10000}$, $nCHin_{3000}$, and/or $nCHin_{1900}$. A further preferred isolated protein is encoded by a nucleic acid molecule that hybridizes under stringent hybridization conditions with a nucleic acid molecule having the complement of nucleic acid sequence SEQ ID NO:3, SEQ ID NO:5, SEQ ID NO:7, SEQ ID NO:9, SEQ ID NO:11, SEQ ID NO:15, SEQ ID NO:20, SEQ ID NO:24, SEQ ID NO:28, SEQ ID NO:32, SEQ ID NO:33, and/or SEQ ID NO:38, or by an allelic variant of any of such nucleic acid molecules. Proteins encoded by nucleic acid sequences SEQ ID NO:3, SEQ ID NO:5, SEQ ID NO:7, SEQ ID NO:9, SEQ ID NO:11, SEQ ID NO:15, SEQ ID NO:20, SEQ ID NO:24, SEQ ID NO:28, SEQ ID NO:32, SEQ ID NO:33, and SEQ ID NO:38 have amino acid sequences SEQ ID NO:4, SEQ ID NO:6, SEQ ID NO:8, SEQ ID NO:10, SEQ ID NO:12, SEQ ID NO:16, SEQ ID NO:18, SEQ ID NO:22, SEQ ID NO:26, SEQ ID NO:30, SEQ ID NO:34, and SEQ ID NO:36, respectively.

Comparison of the CHV amino acid sequences SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, and SEQ ID NO:36 with known sequences indicates that none of these CHV amino acid sequences share more than about 75% identity (many, if not all, sharing significantly less identity) with a known amino acid sequence.

A preferred CHV protein has an amino acid sequence that is at least about 80%, preferably at least about 85%, more preferably at least about 90%, even more preferably at least about 95%, and even more preferably at least about 99% identical to amino acid sequence SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, and/or SEQ ID NO:36.

A more preferred CHV protein includes at least a portion of $PCIR6_{183}$, $PCUS2_{391}$, $PCPK_{400}$, $PCgG_{415}$, $PCdUTP_{152}$, $PCUS9_{149}$, $PCUL48_{97}$, $PCUL52_{48}$, $PCUL51_{86}$, $PCgI_{53}$, and/or $PCT_{93}$, as well as proteins encoded by allelic variants of the nucleic acid molecules encoding such proteins. Also preferred are proteins including at least a portion of CgE and/or CUL49 proteins. A particularly preferred CHV protein includes $PCIR6_{183}$, $PCUS2_{391}$, $PCPK_{400}$, $PCgG_{415}$, $PCdUTP_{152}$, $PCUS9_{391}$, $PCUL48_{97}$, $PCUL52_{48}$, $PCUL51_{86}$, $PCgI_{53}$, and/or $PCT_{93}$, (including, but not limited to the encoded proteins, full-length proteins, processed proteins, multivalent proteins).

Similarly, a preferred CHV protein of the present invention includes at least a portion of SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, and/or SEQ ID NO:36. A particularly preferred CHV protein includes SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, and/or SEQ ID NO:36. Also included are proteins encoded by allelic variants of the nucleic acid molecules encoding such proteins.

The present invention also includes a recombinant vector, which includes at least one isolated CHV nucleic acid molecule inserted into any vector capable of delivering the CHV nucleic acid molecule into a host cell. The vector can be either RNA or DNA, either prokaryotic or eukaryotic, and typically is a virus or a plasmid. Recombinant vectors can be used in the cloning, sequencing, and/or otherwise manipulating of CHV nucleic acid molecules of the present invention. Suitable and preferred CHV nucleic acid molecules to include in a recombinant vector are disclosed herein.

One embodiment of the present invention is a recombinant vector comprising an inactive CHV gene. Such a recombinant vector, also referred to as a transfer vector, can be used to produce a CHV comprising a CHV genome having an inactive gene by, for example, co-transfecting such a transfer vector with a CHV genome into a host cell and selecting for a CHV comprising a recombinant CHV genome having an inactive gene. Such a recombinant CHV genome is produced in the host cell by homologous recombination between the inactive gene on the transfer vector and the corresponding active gene on the transfected CHV genome. Transfection, culturing and purification methods to obtain recombinant CHV and CHV genomes are known to the art; see, for example, Graham et al., 1973, *Virology* 52, 456–467; Graham et al. ibid. is incorporated by reference herein in its entirety.

Another embodiment of the present invention is a recombinant vector comprising a CHV nucleic acid molecule that includes a heterologous nucleic acid molecule (i.e., a heterologous nucleic acid molecule is located within a CHV nucleic acid molecule). Suitable and preferred heterologous nucleic acid molecules are disclosed herein. Such a heterologous nucleic acid molecule can be operatively linked to a transcription control sequence, as disclosed above. A recombinant vector comprising a CHV nucleic acid molecule into which a heterologous nucleic acid molecule is inserted is also a transfer vector. Such a transfer vector can be co-transfected with a CHV genome into a host cell to produce a recombinant CHV having a CHV genome including a heterologous nucleic acid molecule, using methods as described above. Recombinant CHV can be selected by identifying those CHV that have the heterologous nucleic acid molecule. If the recombinant vector comprises a selectable marker into which the heterologous nucleic acid molecule is inserted, selection methods as disclosed herein can also be used to identify recombinant CHV. A preferred embodiment is a recombinant vector comprising a CHV nucleic acid molecule having a heterologous nucleic acid molecule in which a majority of the CHV nucleic acid molecule is deleted; a sufficient size of the CHV nucleic acid molecule is retained to allow homologous recombination to occur with the corresponding target gene on the CHV genome. Examples of insertion of a heterologous nucleic acid molecule into a CHV genomic restriction site and into a CHV gene, as well as use of a selectable marker are provided in the Examples section.

Transfer vectors of the present invention are preferably able to replicate in bacterial, and particularly E. coli, hosts, thereby enabling easy manipulation of the CHV nucleic acid molecules, and, if included, heterologous nucleic acid molecules, prior to insertion of such CHV nucleic acid molecules into a CHV genome. Such manipulations, including culturing of E. coli comprising such vectors, is described, for example, in Sambrook et al. ibid.

In one embodiment, recombinant CHV are produced by co-transfection of a set of overlapping cosmid clones comprising the entire viral CHV genome, at least one of the cosmid clones having been genetically engineered to, for example, contain an inactive CHV gene and/or a heterologous nucleic acid molecule. Details of such a method are presented in the Examples.

Any canid host cell is suitable for recombinant CHV production. Examples of suitable and preferred host cells are provided herein. After transfection, transfected cells are cultured in an effective medium, using techniques such as those described in Graham et al. ibid. As used herein, an effective medium refers to any medium in which the transfected cells can produce recombinant CHV. An effective medium is typically an aqueous medium comprising assimilable carbohydrate, nitrogen and phosphate sources, as well as appropriate salts, minerals, metals and other nutrients, such as vitamins, growth factors and hormones. Culturing is carried out at a temperature, pH and oxygen content appropriate for the transfected cell. Such culturing conditions are well within the expertise of one of ordinary skill in the art.

Recombinant CHV can be recovered from the cultured transfected cells using a combination of standard techniques such as, but not limited to, freeze/thaw cycles, sonication, sucrose gradient centrifugation, and/or high speed centrifugation. Recombinant CHV genomes can be recovered from the cultured transfected cells using a combination of standard techniques such as, but not limited to, those described by Walboomers et al, 1976, Virology 74, 256–258.

Preferably, a recombinant CHV or recombinant CHV genome of the present invention is recovered in "substantially pure" form. As used herein, "substantially pure" refers to a purity that allows for the effective use of the recombinant CHV or CHV genome as a vaccine without substantial negative side effects.

One embodiment of the present invention is a recombinant molecule that includes a CHV nucleic acid molecule operatively linked to a transcription control sequence. Such a recombinant molecule, when introduced into a host cell, can direct the expression of the CHV nucleic acid molecule (s), thereby leading to the production of one or more CHV protein of the present invention. Such a recombinant molecule preferably is replication competent. Suitable and preferred CHV nucleic acid molecules to include in such a recombinant molecule are as disclosed herein for suitable and preferred CHV nucleic acid molecules per se.

Isolated CHV proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing one or more CHV proteins, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred CHV nucleic acid molecules with which to transform a cell are as disclosed herein for suitable and preferred CHV nucleic acid molecules per se.

Suitable host cells to transform include any cell that can be transformed with a CHV nucleic acid molecule of the present invention. Host cells can be either untransformed cells or cells that are already transformed with at least one nucleic acid molecule. Host cells of the present invention either can be endogenously (i.e., naturally) capable of producing CHV proteins of the present invention or can be capable of producing such proteins after being transformed with at least one CHV nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, yeast, insect and mammalian cells. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $P_L$ and lambda $P_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus, phosphate-regulated and nitrate-regulated transcription control sequences as well as other sequences capable of controlling gene expression in prokaryotic or eukaryotic cells, including those disclosed herein for expression of heterologous nucleic acid molecules, including endogenous CHV transcription control regions.

Recombinant cells of the present invention can be used to produce one or more proteins by culturing such cells under conditions effective to produce such a protein, and recovering the protein. Effective conditions to produce a protein include, but are not limited to, appropriate media, bioreactor, temperature, pH and oxygen conditions that permit protein production. Such culturing conditions are well within the expertise of one of ordinary skill in the art.

Depending on the vector and host system used for production, resultant CHV proteins may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

The present invention also includes isolated antibodies capable of selectively binding to a CHV protein of the present invention or to a mimetope thereof. Such antibodies are also referred to herein as anti-CHV antibodies. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce CHV proteins of the present invention. Antibodies raised against defined proteins or mimetopes can be advantageous because such antibodies are not substantially contaminated with antibodies against other substances that might otherwise cause interference in a diagnostic assay or an assay to monitor recombinant CHV administration, or side effects if used in a therapeutic composition.

Antibodies of the present invention have a variety of potential uses that are within the scope of the present invention. For example, such antibodies can be used (a) as compounds to monitor recombinant CHV or recombinant CHV genome administration, (b) as therapeutic compounds to passively immunize an animal in order to protect the animal from CHV infection, and/or (c) as reagents in assays to detect CHV infection.

One embodiment of the present invention is a therapeutic composition that includes a recombinant CHV, a recombinant CHV genome, or a mixture (i.e., combination) of one or more recombinant CHVs and/or recombinant CHV genomes. As used herein, a therapeutic composition, or vaccine, is a formulation that, when administered to an animal in an effective manner, is capable of protecting that animal from a disease against which the therapeutic composition is targeted. Some therapeutic compositions of the present invention can modulate (i.e., either elicit or suppress) an immune response to protect an animal from disease, whereas other therapeutic compositions can protect an animal in other ways, as disclosed herein. A therapeutic composition of the present invention can be used to prevent and/or treat a disease depending on whether the composition is administered as a prophylactic or after the animal has the disease.

A therapeutic composition of the present invention, when administered to an animal in an effective manner, can infect the cells of the animal (in a manner essentially harmless to the animal) and direct the production of a protective compound able to protect the animal from a disease targeted by the therapeutic composition. If a recombinant CHV includes a protective compound in its envelope and/or capsid, the CHV can function as an immunogen per se.

As disclosed herein, therapeutic compositions can be designed to target a variety of diseases, depending on the nature of the heterologous nucleic acid molecule(s) included in such recombinant CHV and recombinant CHV genomes. Examples of such diseases, and the nature of the corresponding heterologous nucleic acid molecules, are disclosed herein. Furthermore, therapeutic compositions of the present invention can comprise multivalent vaccines. For example, a CHV genome can encode a variety of protective compounds, and/or more than one recombinant CHV genome and/or recombinant CHV can be administered. The present invention also includes the use of a recombinant CHV or recombinant CHV genome to protect an animal against CHV infection. Such a therapeutic composition can, but need not, include a heterologous nucleic acid molecule.

A therapeutic composition of the present invention is preferably administered to a canid, due to the host range specificity of CHV. Suitable canids include dogs (including domesticated and wild dogs), foxes, wolves, jackals, coyotes, and other members of the family Canidae. Particularly preferred canids to treat include domesticated dogs.

It is, however, also within the scope of the present invention to administer therapeutic compositions to other animals. Recombinant CHV can be administered to any animal susceptible to such therapy. Without being bound by theory, it is believed that sufficiently high doses of a recombinant CHV composition of the present invention may be infectious in other animals, particularly other mammals. Mink and other mink-like mammals (e.g., those of the family Mustelidae, such as ermines, ferrets, fishers, martens, otters, and weasels), in particular, may be susceptible to CHV infection, as suggested by the ability of CHV to infect mink lung cells. The host range of recombinant CHV of the present invention can also be altered, as disclosed herein, to infect other animal cells. It is also to be noted that CHV genomes of the present invention can be administered as naked DNA vaccines or in association with other carriers (e.g., liposomes). In accordance with these embodiments, any animal, including, but not limited to, mammals, birds, amphibians, and arthropods (including arachnids and insects) can be administered a therapeutic composition of the present invention. Preferred animals to treat include dogs, cats, humans, ferrets, prairie dogs, other rodents, horses, cattle, sheep, pigs, and poultry, as well as other pets, work animals, economic food animals and zoo animals.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the vaccine can also include an adjuvant and/or a carrier. One advantage of live virus-based vaccines, such as the recombinant CHVs of the present invention, is that adjuvants and carriers are not required to produce an efficacious vaccine, and in some cases, the advantages of recombinant CHV vaccines of the present invention would be precluded by the use of some adjuvants. However, it should be noted that use of adjuvants or carriers is not precluded by the present invention. Adjuvants are typically substances that generally enhance the immune response of an animal to a specific antigen. Suitable adjuvants include, but are not limited to, other bacterial cell wall components; aluminum-based salts; calcium-based salts; silica; polynucleotides; toxoids; serum proteins; other viral coat proteins; other bacterial-derived preparations; block copolymer adjuvants, such as Hunter's Titermax™ adjuvant (Vaxcel™, Inc. Norcross, GA); Ribi adjuvants (available from Ribi ImmunoChem Research, Inc., Hamilton, MT); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

In one embodiment, a therapeutic composition of the present invention is administered to an animal in an effective manner to enable the animal to produce sufficient protective compound(s) and/or to directly mount a sufficient immune response to protect the animal from disease. Acceptable protocols to administer therapeutic compositions in an effective manner include enumeration of individual dose size, number of doses, frequency of dose administration, and mode of administration. Determination of such protocols can be accomplished by those skilled in the art. A suitable single dose is a dose that is capable of protecting an animal from disease when administered one or more times over a suitable time period.

A preferred single dose of a recombinant CHV of the present invention is from about $1 \times 10^4$ to about $1 \times 10^7$ virus plaque forming units (pfu) per kilogram body weight of the animal. Booster vaccinations can be administered from about 2 weeks to several years after the original vaccination. Booster vaccinations preferably are administered when the immune response of the animal becomes insufficient to protect the animal from disease. A preferred administration schedule is one in which from about $1 \times 10^4$ to about $1 \times 10^7$ virus plaque forming units per kilogram (kg) body weight of the animal are administered from about 1 to about 2 times over a time period of from about 12 to about 18 months. Modes of administration can include, but are not limited to, subcutaneous, intradermal, intravenous, intranasal, oral, transdermal and intramuscular routes.

A recombinant CHV genome can be administered in a variety of ways, with intramuscular, subcutaneous, intradermal, transdermal, intranasal and oral routes of administration being preferred. A preferred single dose of a recombinant CHV genome ranges from about 1 nanogram (ng) to about 100 micrograms (µg), depending on the route of administration and/or method of delivery, as can be determined by those skilled in the art; see, for example, Wolff et al., 1990, *Science* 247, 1465–1468. Suitable delivery methods include, for example, injection, as drops, aerosolized and/or topical administration. Suitable excipients include, for example, physiologically acceptable aqueous solutions (e.g., phosphate buffered saline as well as others disclosed above), liposomes (including neutral or cationic liposomes), and other lipid membrane-based vehicles (e.g., micelles or cellular membranes).

In one embodiment, a therapeutic composition of the present invention is administered to a dam to protect her offspring from disease. In this method, the dam is administered the therapeutic composition at such a time as to be able to develop an immune response such that she can passively transfer antibodies produced against a protective compound of the present invention to her offspring. Such a method can also be used to protect offspring from CHV infection and is particularly useful since neonates are most affected by CHV infection.

The efficacy of a therapeutic composition of the present invention to protect an animal from disease can be tested in a variety of ways including, but not limited to, detection of protective protein or RNA within the treated animal, detection of protective antibodies within the treated animal, detection of cellular immunity within the treated animal, or challenge of the treated animal with an appropriate infectious agent, or other disease component, to determine whether the animal is now protected from the disease caused by such an agent or other component. Such techniques are known to those skilled in the art. In one embodiment, anti-CHV antibodies of the present invention are used to monitor recombinant CHV infection and can be used to distinguish wild type infections from infections using recombinant CHV of the present invention (i.e., by using antibodies that specifically recognize either recombinant CHV of the present invention or wild type virus).

In one embodiment, the efficacy of a therapeutic composition of the present invention may be improved by co-administering (a) a recombinant CHV or recombinant CHV genome and (b) a protective compound (e.g., subunit vaccine) encoded by a CHV nucleic acid molecule or heterologous nucleic acid molecule present in the CHV genome. While not being bound by theory, it is believed that administration of a protective compound in conjunction with the recombinant CHV or CHV genome can boost the immune response, particularly the antibody titer. The protective compound can be administered prior to, concomitant with, and/or following administration of the recombinant CHV or CHV genome. The protective compound can be either produced naturally, recombinantly, or synthetically. The protective compound should be sufficiently pure to allow for effective use of the compound as a vaccine; i.e., it should not cause substantial side effects. The protective compound can be joined (i.e., conjugated) to a carrier or other material that enhances the immunogenicity of the compound.

The present invention also includes the use of CHV nucleic acid molecules, CHV proteins, and anti-CHV antibodies as therapeutic compositions to protect animals from CHV infection. Methods to administer such compositions to canids are known to those skilled in the art. For example, a preferred single dose of a protein, mimetope or antibody therapeutic composition is from about 1 microgram (μg) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 μg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes. A CHV nucleic acid molecule, including recombinant molecules, can be administered as described herein for administration of CHV genomes or CHV of the present invention. Recombinant molecules including heterologous nucleic acid molecules can also be used as therapeutic compositions to protect an animal from disease, using methods as disclosed herein.

It is also within the scope of the present invention to use isolated CHV proteins, mimetopes, CHV nucleic acid molecules and anti-CHV antibodies of the present invention as diagnostic reagents to detect CHV infection. Methods to use such diagnostic reagents to diagnose infection are well known to those skilled in the art.

The following examples are provided for the purposes of illustration and are not intended to limit the scope of the present invention.

EXAMPLES

It is to be noted that the Examples include a number of molecular biology, virology, microbiology, immunology and biochemistry techniques considered to be known to those skilled in the art. Disclosure of such techniques can be found, for example, in Sambrook et al., ibid.; Ausubel et al, 1993, *Current Protocols in Molecular Biology*, Greene/Wiley Interscience, New York, N.Y.; Graham et al, ibid; and related references. Ausubel et al, ibid. is incorporated by reference herein in its entirety. Nucleic acid and amino acid sequences of the present invention were compared to known sequences using BLAST (NCBI) and DNAsis (Hitachi Software, San Bruno, Calif.

Example 1

This Example demonstrates the isolation of certain CHV nucleic acid molecules of the present invention.

The disclosed CHV nucleic acid molecules were amplified from a CHV genome by PCR amplification using a variety of primers designed in view of published herpesvirus sequences. The following PCR conditions were used: 0.2 millimolar (mM) dNTPs, 1 μM of each primer, 1X PCR buffer (available from Perkin Elmer Cetus, Emeryville, Calif., 50 ng of CHV DNA (isolated from CHV strain D 004 as described in Example 2) and 0.5 μl of a thermostable DNA polymerase, all in an about 100 μl total volume. The PCR reactions included an initial denaturation for 3 minutes at 95° C., five cycles of 1 minute each at 95° C., 35° C. for 1 minute, 72° C. for 1 minute, 35 cycles of 1 minute each at 95° C., 37° C. for 1 minute, 72° C. for 1 minute, and finally 10 minutes at 72° C. The resultant PCR products were directly cloned into the PCRII TA cloning vector (available from Invitrogen Corp., San Diego, Calif. according to the manufacturer's specifications. Primers which were successful in amplifying fragments from a CHV genome, which was determined to be very AT-rich compared to other herpesvirus genomes, are described below.

A. Isolation of a nucleic acid molecule including a partial CHV dUTPase gene and a partial CHV UL51 gene The following primers were designed using dUTPase protein sequence derived from HSV-1 (McGeoch et al, 1988, *J. Gen. Virol.* 69, 1531–1574), EHV-4 (Riggio et al, 1993, *Arch. Virol.* 133, 171–178), BHV-1 (Liang et al, 1993, *Virology* 195, 42–50), and EBV (Lees et al, 1993, *Virology* 195, 578–586: Primer 212S (dUTPase forward) having nucleic acid sequence 5' GG CGA ATT CCI AAR MGI GAI GAR GAY G 3', denoted herein as SEQ ID NO:39; and Primer 365A (dUTPase reverse) having nucleic acid sequence 5' CGCG GAT CCI GTI SWI CCY AAI CC 3', denoted herein as SEQ ID NO:40. These primers led to the amplification of an about 743 nucleotide fragment, which was significantly larger than expected. Nucleic acid sequence analysis, described in Example 3, indicated that the 743 nucleotide fragment contained part of the CUL51 gene as well as part of the CdUTPase gene; as such, the fragment was denoted nCdUTP/CUL51$_{743}$. Nucleic acid sequence analysis also indicated that the dUTPase reverse primer actually hybridized to a region of the CHV DNA genome within the CUL51 gene rather than within the CdUTPase gene. It is believed that the mispriming was due to nucleotide position 19 of SEQ ID NO:40 being a Y instead of an R; the latter sequence would have matched more closely to the targeted priming region, about 290 nucleotides upstream from the 3' end of nucleic acid molecule nCdUTP/CUL51$_{743}$. This result demonstrates the sensitivity of PCR amplification to primer design.

B. Isolation of a CHV gE nucleic acid molecule

The following primers were designed using gE protein sequence derived from FHV-1 (Spatz et al, 1994, *J Gen. Virol.* 75, 1235–1244), EHV-1 (Elton et al, 1991, *Gene* 101, 203–208), and BHV-1 (Leung-Tack et al, 1994, *Virology* 199, 409–421): Primer 197S (gE forward) having nucleic acid sequence 5' GGC GAA TTC TAY CAY WSI CAY GTI TA 3', denoted herein as SEQ ID NO:41; and Primer 441A (gE reverse) having nucleic acid sequence 5' CGC GGA TCC RTC RTT ISW IGG DAI ISW IGT 3', denoted herein as SEQ ID NO:42. These primers led to the amplification of an about 750 nucleotide fragment, referred to herein as nCgE$_{750}$.

C. Isolation of a CHV TK nucleic acid molecule

The following primers were designed using TK protein sequence derived from HSV-1 (McGeoch et al., 1988, ibid.), HSV-2 (Kit et al, 1987, *Antimicrob. Agents Chemother.* 31, 1483–1490, BHV-1 (Kit et al, U.S. Pat. No. 4703011, issued Oct. 27, 1987), FHV-1 (Nunberg et al, 1989, *J. Virol.* 63, 3240–3249), EHV-1 (Robertson et al, 1988, *Nuc. Acids Res.* 16, 11303–11317), and PRV (Prieto et al, 1991, *J. Gen. Virol.* 72, 1435–1439): Primer EJH 002 (TK forward) having nucleic acid sequence 5' GGC GAA TTC GGI AAR WSI ACI RC 3', denoted herein as SEQ ID NO:43; and Primer EJH004 (TK reverse) having nucleic acid sequence 5' GGC GGA TCC GGT TGI CKR TC 3', denoted herein as SEQ ID NO:44. These primers led to the amplification of an about 280 nucleotide fragment, referred to herein as $nCTK_{280}$.

D. Isolation of a nucleic acid molecule including CHV gC and CHV UL45 genes

The following primers were designed using gC and UL45 sequences derived from Limbach et al., ibid.: Primer gC sense, having nucleic acid sequence 5' CGCGGATCCAAG-GTAATAAGTCAAAATGAG 3', denoted herein as SEQ ID NO:45; and Primer gC ant, having nucleic acid sequence 5' CGCGGATCCGACAAAAACAAAAAGTAATG 3', denoted herein as SEQ ID NO:46. These primers led to the amplification of an about 2100 nucleotide fragment, referred to herein as $nCgC/CUL45_{2100}$.

E. Attempt to isolate a CHV ribonucleotide reductase gene

The following primers were designed using ribonucleotide subunit small subunit protein sequence derived from HSV-1 (McGeoch et al. 1988, ibid.), PRV (Dewind et al. 1993, *J. Gen. Virol.* 74, 351–359), EHV-1 (Telford et al. 1992, *Virology* 189, 04–316) and BHV-1 (Simard et al. 1992, *Virology* 190, 689–701): Primer EJH 021 (RR forward) having nucleic acid sequence 5' CCG AAT TCY TIA TGA THY TIA THG ARG G 3', denoted herein as SEQ ID NO:47; and Primer EJH022 (RR reverse) having nucleic acid sequence 5' CCG GAT CCY TCR AAR AAR TTI GTR TGY TT 3', denoted herein as SEQ ID NO:48. These primers did not lead to the amplification of a fragment under a variety of magnesium and amplification conditions, suggesting the lack of a coding region for a ribonucleotide reductase small subunit in CHV. As a control, these primers were shown to be able to easily amplify a ribonucleotide reductase small subunit fragment from an FHV genome.

Example 2

This Example describes the production of CHV genomic libraries.

Canine herpesvirus strain D 004 (Binn, et al., 1967, *Proc. Soc. Exp. Biol. Med.* 126, 140) was obtained from ATCC. Virus were propagated on Madin-Darby Canine Kidney (MDCK) cells according to standard virological procedures. Viral DNA was prepare from CHV-infected MDCK cells by previously described methods; see, for example, Walboomers et al, ibid. The viral DNA was digested with restriction endonucleases HindIII, PstI, EcoRI or XbaI, and the resultant digests were cloned into either vector pSP72 (available from Promega Corp., Madison, Wis.), or pLitmus 28 or 38 (available from New England Biolabs, Beverly, Mass.). DNA was prepared from the resultant recombinant plasmids and the inserts were sorted according to size.

Example 3

This Example describes the isolation of genomic HindIII restriction fragment nucleic acid molecules containing CdUTPase nucleic acid sequences and the nucleic acid sequencing of at least regions of these nucleic acid molecules.

Figure 3:
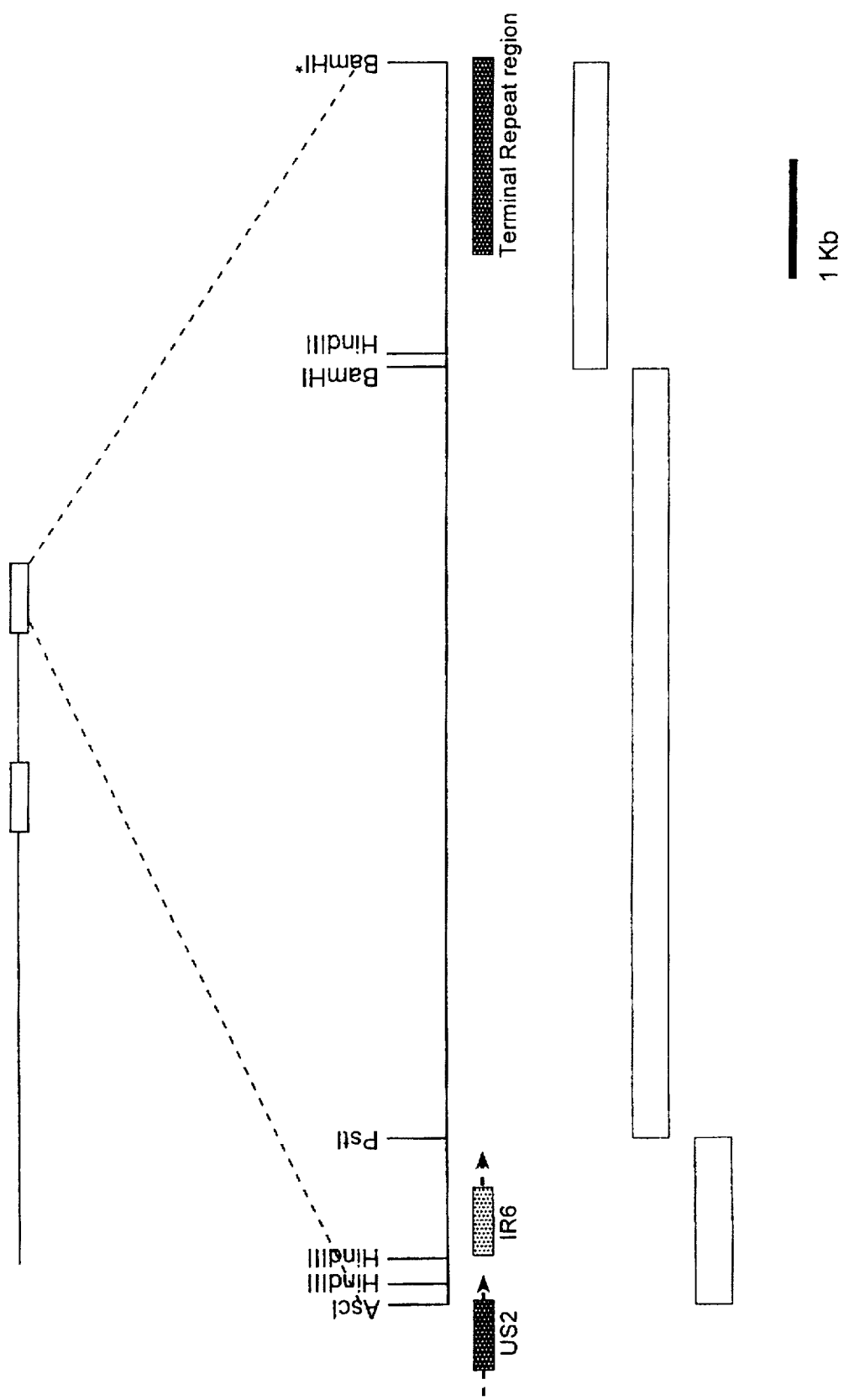

Nucleic acid molecule $nCdUTP/CUL51_{743}$, produced as described in Example 1, was labelled with either $^{32}p$ or digoxigenin (available from Boehringer Mannheim Biochemicals (BMB), Indianapolis, Ind.) and used to screen the CHV HindIII fragment-containing library, either by colony hybridization or Southern blotting. Two clones hybridized with $nCdUTP/CUL51_{743}$, one containing a HindIII fragment of about 3000 nucleotides, referred to herein as $nCHin_{3000}$, and another containing a HindIII fragment of about 1,900 nucleotides, referred to herein as $nCHin_{1900}$. The HindIII fragments were further characterized by restriction mapping, as shown in FIG. 1. Also shown is the relative location of $nCdUTP/CUL51_{743}$ (referred to therein as $nCdUTP_{743}$) with respect to the HindIII fragments.

Nucleic acid molecules $nCdUTP/CUL51_{743}$, $nCHin_{3000}$, and $nCHin_{1900}$ were submitted to DNA sequence analysis, using a sequencing strategy as depicted in FIG. 1. Among sequences obtained were SEQ ID NO:13 and SEQ ID NO:14, which include SEQ ID NO:15 and SEQ ID NO:33, as well as SEQ ID NO:21, SEQ ID NO:23, SEQ ID NO:25 and SEQ ID NO:27. The relative locations of genes included in these sequences (i.e., the CUL52, CUL51, CdUTPase and CUL48 genes) are shown in FIG. 1. Also shown is the apparent location of the CUL49 gene.

SEQ ID NO:13 and SEQ ID NO:14 represent the deduced nucleic acid sequences of the two complementary strands of $nCdUTP/CUL51_{743}$. SEQ ID NO:13 includes a partial coding region for a CdUTPase protein of about 152 amino acids, denoted herein as $nCdUTP_{459}$ and represented by SEQ ID NO:15, assuming a first in-frame codon spanning about nucleotides 3–5, and a stop codon spanning about nucleotides 459–461 of SEQ ID NO:13. The amino acid sequence of the encoded protein $PCdUTP_{1522}$ is represented by SEQ ID NO:16. SEQ ID NO:14 includes a partial coding region for a CUL51 protein of about 86 amino acids, denoted herein as $nCUL51_{261}$ and represented by SEQ ID NO:33, assuming a first in-frame codon spanning about nucleotides 1–3, and a stop codon spanning about nucleotides 259–261 of SEQ ID NO:14. The amino acid sequence of the encoded protein $PCUL51_{86}$ is represented by SEQ ID NO:34.

SEQ ID NO:21 and SEQ ID NO:23 represent the deduced nucleic acid sequences of the two complementary strands of $nCUL48_{294}$. SEQ ID NO:21 includes a partial coding region for a CUL48 protein of about 97 amino acids, denoted herein as $nCUL48_{291}$ and represented by SEQ ID NO:24, assuming a first in-frame codon spanning about nucleotides 3–5 of SEQ ID NO:21. The amino acid sequence of the encoded protein $PCUL48_{97}$ is represented by SEQ ID NO:22.

SEQ ID NO:25 and SEQ ID NO:27 represent the deduced nucleic acid sequences of the two complementary strands of $nCUL52_{146}$. SEQ ID NO:25 includes a partial coding region for a CUL52 protein of about 48 amino acids, denoted herein as $nCUL52_{144}$ and represented by SEQ ID NO:28, assuming a first in-frame codon spanning about nucleotides 1–3 of SEQ ID NO:25. The amino acid sequence of the encoded protein $PCUL52_{48}$ is represented by SEQ ID NO:26.

Example 4

This Example describes a method to identify restriction enzymes that effect limited cleavage of the CHV genome. Also described is the isolation and sequencing of an AscI fragment containing the entire US region of CHV.

CHV DNA was evaluated for recognition sites for several restriction enzymes with 8-base, or larger, recognition sites. No sites were found for enzymes Sse8387I, I-Sce-I, or NotI. Two AscI sites were found, which were mapped to sites within the inverted repeats surrounding the US region, specifically within CHV gene US2 (see FIG. 2). The AscI fragments, of 9.3, 10.0 and approximately 100–120 kilobases (kb), were cloned into pLitmus 38 and submitted to restriction enzyme mapping analysis. The restriction map of the 9.3-kb AscI fragment, denoted herein as $nCAsc_{9300}$ is shown in FIG. 2; this fragment apparently contains the entire CUS region, as well as small portions of the internal and terminal IR regions. The 10.0-kb AscI-blunt fragment, denoted herein as nCAsc1000, contains most of the terminal IR region and is shown in FIG. 3. The about 100–120-kb AscI-blunt fragment contains the remainder of the CHV genome. Both AscI sites are located just 5' of the diploid copies of the CHV homolog of the EHV-1 IR6 gene (Breeden et al, 1992, *Virology* 191, 649–660), and the orfI of BHV-1 (Leung-Tack et al. ibid.). The AscI sites appear to be located within an open reading frame that is the homolog of the EHV US1 gene (Breeden et al ibid.) and the HSV-1 US2 gene (McGeoch et al. 1985, *J. Mol. Biol.* 181, 1–13), although the size is somewhat different from these other genes. No function has been ascribed to the HSV-1 US2 gene product, but it has been shown to be dispensable for growth in tissue culture and to attenuate the virus (Meignier et al. 1988, *Virology* 162, 251–254).

Figure 2:
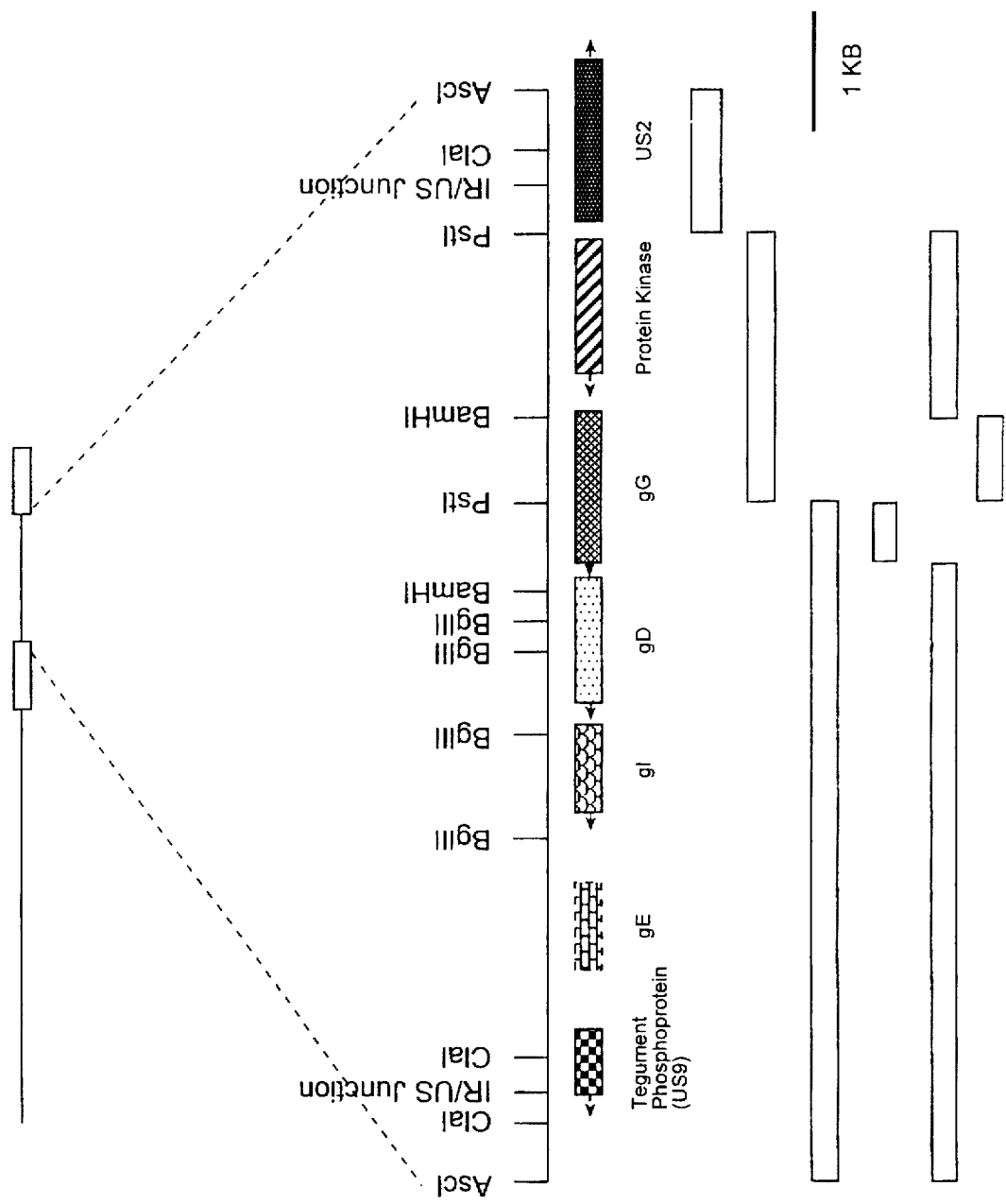

Nucleic acid molecules $nCAsc_{9300}$ and $nCAsc_{10000}$ were submitted to DNA sequence analysis using a strategy as depicted in FIG. 2 and FIG. 3. Among sequences obtained were SEQ ID NO:1, SEQ ID NO:2, SEQ ID NO:17, SEQ ID NO:19, SEQ ID NO:29, and SEQ ID NO:31 The relative locations of genes included in these sequences (i.e., the CUS9, CgI, CgD, CgG, CPK, CUS2, and CIR6 genes) are shown in FIG. 2 and FIG. 3. Also shown is the putative location of the CgE gene.

SEQ ID NO:1 and SEQ ID NO:2 represent the deduced nucleic acid sequences of the two complementary strands of $nCUS_{5495}$. Translation of SEQ ID NO:1 and SEQ ID NO:2 indicates that nucleic acid molecule $nCUS_{5495}$ encodes CIR6, CUS2, CPK and CgG proteins as well as a portion of a CgD protein. Specifically, SEQ ID NO:2 includes: a coding region for a CIR6 protein of about 183 amino acids, denoted herein as $nCIR6_{552}$ and represented by SEQ ID NO:3, assuming a start codon spanning about nucleotides 4566–4568 and a stop codon spanning about nucleotides 5115–5117 of SEQ ID NO:2; and a coding region for a CUS2 protein of about 391 amino acids, denoted herein as $nCUS2_{1176}$ and represented by SEQ ID NO:5, assuming a start codon spanning about nucleotides 3232–3234 and a stop codon spanning about nucleotides 4405–4407 of SEQ ID NO:2. The amino acid sequences of the respective encoded proteins $PCIR6_{183}$ and $PCUS2_{391}$ are represented by SEQ ID NO:4 and SEQ ID NO:6. SEQ ID NO:1 includes: a coding region for a CPK protein of about 400 amino acids, denoted herein as $nCPK_{1203}$ and represented by SEQ ID NO:7, assuming a start codon spanning about nucleotides 2384–2386 and a stop codon spanning about nucleotides 3584–3586 of SEQ ID NO:1; a coding region for a CgG protein of about 415 amino acids, denoted herein as $nCgG_{1248}$ and represented by SEQ ID NO:9, assuming a start codon spanning about nucleotides 3698–3700 and a stop codon spanning about nucleotides 4943–4945 of SEQ ID NO:1; and a partial coding region for a CgD protein of about 119 amino acids, denoted herein as $nCgD_{357}$ and represented by SEQ ID NO:11, assuming a start codon spanning about nucleotides 5137–5139. The amino acid sequences of the respective encoded proteins $PCPK_{400}$, $PCgG_{415}$, and $PCgD_{119}$ are represented by SEQ ID NO:8, SEQ ID NO:10 and SEQ ID NO:12.

SEQ ID NO:17 and SEQ ID NO:19 represent the deduced nucleic acid sequences of the two complementary strands of $nCUS9_{579}$. SEQ ID NO:17 includes a coding region for a CUS9 protein of about 149 amino acids, denoted herein as $nCUS9_{450}$ and represented by SEQ ID NO:20, assuming a start codon spanning about nucleotides 54–56 and a stop codon spanning about nucleotides 501–503 of SEQ ID NO:17. The amino acid sequence of the encoded protein $PCUS9_{149}$ is represented by SEQ ID NO:18.

SEQ ID NO:29 and SEQ ID NO:31 represent the deduced nucleic acid sequences of the two complementary strands of $nCgI_{161}$. SEQ ID NO:29 includes a partial coding region for a CgI protein of about 53 amino acids, denoted herein as $nCgI_{159}$ and represented by SEQ ID NO:32, assuming a first in-frame codon spanning about nucleotides 3–5 of SEQ ID NO:29. The amino acid sequence of the encoded protein $PCgI_{53}$ is represented by SEQ ID NO:30.

Example 5

This Example describes the nucleic acid sequencing of additional nucleic acid molecules of the present invention.

Nucleic acid molecule $nCTK_{280}$, produced as described in Example 1, was submitted to DNA sequence analysis to obtain the following sequences. SEQ ID NO:35 and SEQ ID NO:37 represent the deduced nucleic acid sequences of the two complementary strands of $nCTK_{280}$. SEQ ID NO:35 includes a partial coding region for a CTK protein of about 93 amino acids, denoted herein as $nCTK_{279}$ and represented by SEQ ID NO:38, assuming a first in-frame codon spanning about nucleotides 2–4 of SEQ ID NO:35. The amino acid sequence of the encoded protein $PCTK_{93}$ is represented by SEQ ID NO:36.

Example 6

This Example discloses the production of a recombinant CHV genome and recombinant CHV of the present invention.

A cassette including the human CMV immediate early promoter and the poly-adenylation signal from bovine growth hormone separated by a polylinker was PCR amplified from plasmid pcDNA3 (available from Invitrogen) using forward primer EJHO58 having nucleic acid sequence 5' TCCCCCGGGGGCGCGCCTTGACATTGATTATTGAC 3', denoted SEQ ID NO:49, and reverse primer EJH059 having nucleic acid sequence 5' GCCCTTAAGGGGCGCGCCAATGCGATGCAATTTCC 3', denoted SEQ ID NO:50. EJHO58 has SmaI and AscI sites attached to the 5' end of pcDNA3 homologous sequences, and EJH059 has Af1II and AscI sites attached to the 5' end of pcDNA3 homologous sequences. The resultant PCR amplified fragment of about 930 nucleotides was digested with SmaI and Af1II and ligated into the SnaBI and AflII sites of plasmid pLitmus 38. This cloning procedure eliminated the entire polylinker region of pLitmus38. The resulting recombinant plasmid, denoted herein as pAscCMV/BGH, contains the CMV promoter—BGH polyadenylation signal cassette, with its original polylinker, in a plasmid such that the entire cassette can be excised with enzyme AscI. This cassette plasmid can also be prepared with other rare-cutting enzyme sites flanking the cassette.

Plasmid pAscCMV/BGH allows for the insertion of heterologous nucleic acid molecules between the CMV promoter and the BGH polyadenylation signal. The resulting heterologous nucleic acid molecule-containing cassette was excised from the plasmid for insertion into a CHV genome. For example, a heterologous nucleic acid molecule containing a lacZ gene was inserted into the polylinker region of pAscCMV/BGH such that the lacZ gene is expressed by the CMV promoter in a eukaryotic system. The cassette containing the lacZ gene, referred to herein as AscCMV/lacZ/BGH is then excised from the plasmid by AscI digestion and gel purified by standard methods.

About 5–10 μg of CHV DNA is digested with AscI, resulting in three fragments as disclosed herein. The DNA fragments are dephosphorylated with calf intestine alkaline phosphatase (available from BMB) for 10 minutes at 37° C.; the enzyme is then inactivated for by incubation for 10 minutes at 65° C. The phosphatase-treated digested CHV DNA is then subjected to extraction with phenol and phenol/chloroform and precipitated with ethanol.

The phosphatase-treated digested CHV genomic DNA is mixed with the gel-purified AscCMV/lacZ/BGH cassette at a molar ratio of approximately 1:2 under standard ligation conditions. Since the viral DNA is dephosphorylated, it should not be able to self ligate; thus all resultant ligated viral molecules should contain two copies of the inserted cassette. The ligated DNA is then subjected to phenol extraction and ethanol precipitated.

The precipitated ligated DNA is resuspended in hepes-buffered saline and submitted to standard viral transfection conditions, such as that described by Graham, et al. ibid, along with appropriate controls (e.g., undigested viral DNA, digested and dephosphorylated viral DNA that was self-ligated, and no DNA). Resultant viral plaques are screened under an X-gal overlay for expression of β-galactosidase.

Example 7

This Example discloses the production of another recombinant CHV genome and recombinant CHV of the present invention.

A recombinant, or transfer, vector to be used in the production of a recombinant CHV having a heterologous nucleic acid molecule in a TK gene of the CHV genome is constructed as follows. A CHV TK nucleic acid molecule of the present invention (e.g., $nCTK_{280}$) is ligated into a pLitmus plasmid to produce a pCTK-Litmus plasmid. An expression cassette including a heterologous nucleic acid molecule (e.g., a lacZ gene or a nucleic acid molecule encoding an antigen isolated from a pathogenic organism) ligated to a CMV immediate early promoter and a BHV polyadenylation site in such a manner that the heterologous nucleic acid molecule is expressed in a eukaryotic cell is inserted into the CTK nucleic acid molecule within pCTK-Litmus such that there are CTK flanking sequences on either side of the expression cassette (e.g., into a restriction site internal to $nCTK_{280}$).

A recombinant CHV is produced by co-transfecting the recombinant vector and CHV DNA into canine MDCK cells using previously described methods; see, for example, Graham et al. ibid. Recombinant TK negative CHV are selected for by passage in bromodeoxyuridine; see, for example, Kit et al., 1983, Virology 130, 381–389. If the heterologous nucleic acid molecule is the lacZ gene, such recombinant CHV can also be selected as described in Example 6.

Example 8

This Example discloses the production of another recombinant CHV genome and recombinant CHV of the present invention.

A recombinant, or transfer, vector to be used in the production of a recombinant CHV having a heterologous nucleic acid molecule in a dUTPase gene of the CHV genome is constructed as follows. A CHV dUTPase nucleic acid molecule of the present invention (e.g., $nCdUTP_{459}$) is ligated into a pLitmus plasmid to produce a pCdUTP-Litmus plasmid. An expression cassette including a heterologous nucleic acid molecule (e.g., a lacZ gene or a nucleic acid molecule encoding an antigen isolated from a pathogenic organism) ligated to a CMV immediate early promoter and a BHV polyadenylation site in such a manner that the heterologous nucleic acid molecule is expressed in a eukaryotic cell is inserted into the CdUTP nucleic acid molecule within pCdUTP-Litmus such that there are CdUTPase flanking sequences on either side of the expression cassette (e.g., into a restriction site internal to $nCdUTP_{459}$).

A recombinant CHV is produced by co-transfecting the recombinant vector and CHV DNA into canine MDCK cells as described in Example 7. Recombinant dUTPase negative CHV are selected for by passage in mercurithio analogs of deoxyuridine; see, for example, Holliday et al, 1991, Antiviral Research 16, 197–203. If the heterologous nucleic acid molecule is the lacZ gene, such recombinant CHV can also be selected as described in Example 6. Recombinant virus carrying the foreign DNA of interest can also be selected by either by plaque hybridizations, or by dot-blot hybridizations of infected cell cultures. Verification of the proper insert within the CHV genome is conducted by Southern hybridization analysis.

Example 9

This Example discloses the production of a recombinant CHV by co-transfection of a set of overlapping cosmid clones comprising the entire viral CHV genome.

A library of CHV cosmid clones is created in the cosmid vector SuperCos (available from Stratagene Cloning Systems, La Jolla, Calif.) according to manufacturer's specifications, except that the vector is modified to contain one or more restriction sites not present in CHV genomic DNA (e.g., Sse83871, I-Sce-I, or NotI) so that the cosmid inserts can be excised prior to cotransfection. A heterologous nucleic acid molecule in an expression cassette, such as one of those described in Examples 6–8, is inserted into a cosmid clone using standard procedures. A recombinant CHV is produced by co-transfection of a set of overlapping cosmid clones comprising the entire viral CHV genome, including the cosmid comprising a heterologous nucleic acid molecule, using techniques as described in van Zihl et al., 1988, J. Virol. 62, 2191–2195.

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
    ( A ) LENGTH: 5495 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

| | | | | | |
|---|---|---|---|---|---|
| CTGCAGTGTA | TTTAAAAAAT | AAAATCTATG | AATGAAATCT | ATGAATGAAA | TCTATGAATG | 60 |
| AAATCTATGA | ATGAAATCTA | TGAATGAAAT | CTATGAATGA | AATCTATGAA | TGAAATCTAT | 120 |
| GAATGAAATC | TATGAATGAA | ATCTATGAAT | GAAATCTATG | AATGAAATCT | ATGAATGAAA | 180 |
| TCTATGAATG | AAATCTATGA | ATGAAATCTA | TGAATGAAAT | CTATGAATGA | AATCTATGAA | 240 |
| TGAAATCTAT | GAATGAAATC | TATGAATGAA | ATCTATGAAT | GAAATCTATG | AATGAAATCT | 300 |
| ATGAGACAAG | TATTTTAAAA | ATATTTAAA | TTTATAAGGT | TAAGTACAGT | AGGCGGTTGG | 360 |
| GTAAACATTT | TTAGTTTTTC | AAGTTTTTAG | TTTTCTGGT | ATCCTACCCA | ACACAAATGC | 420 |
| ATCTTCGGAT | ACATTTATTT | TAAGAGAGTA | ATCACTTTTT | AGAATATATC | TTATTGGTGG | 480 |
| TACATTTATA | AATTTTGGAC | CATCCCAATA | ACACTTCGAT | TCCACAAGCG | AAGAAGGTAC | 540 |
| TTCCATAAGC | TGAGAAGCGT | TTACTTGATT | GTAGGGAGAA | CTTGGCGTTT | CAAAATCCTT | 600 |
| TAGAACGTAT | AGTCTGCAAT | ACATAGGTTC | AATATCATCT | TCATACCTCT | CATCAGGATA | 660 |
| TGAAAATGGA | AGTTTCACAA | AGGTTCCATC | ACGAAGCTTT | TTGAAGAATC | GTACATCCGT | 720 |
| AGGTGGTGTA | GGAACAATAG | TGAAGGCGTG | CGGTTCACCC | TGGTTTTTCA | CACGTGCAAG | 780 |
| CGCTGGTGTG | GTTTTAGGGC | GAACTGGAAA | ATAACCAGGC | GGAACTTGTG | CGTAGAATCC | 840 |
| TTCATTAAGT | TCTCCACGAC | AGCGTCTGAA | GTATGATGGC | ATATTAGCTT | GATCGGAGTT | 900 |
| GTTATCAAAT | AGAGCAAATG | AAGCACTCAT | TTTAAAACTT | TTTAGTTAAG | CTTTAAAAAC | 960 |
| AAGTGAAGAT | TTAAAAATGT | AGGATAAAAT | GCCAGTTTAT | ATACAGTAAG | AATATGGGAG | 1020 |
| TGGTTCACAT | AAAAAACCAG | AATTTCAGGT | TTACATCTAC | TGTTTATTCA | CAACAAATAT | 1080 |
| AAACAAACTT | AGTTTCCACA | TAAACATGAA | CTAAATAGAG | ATGAACGTTG | AGCGTTGGTA | 1140 |
| GGTTGTGTAG | AAGACATACC | ATCGTTTTCA | TTTTGGTTA | TTGTTTTGGC | GCGCCTTGAA | 1200 |
| AATAATCGTT | TAAAAATATT | TGGTTTGGAT | AGCCTTTTCA | TAGGTTTCAC | CCCATGCAAG | 1260 |
| TCATCCTCTT | CTGGTTCAGG | AATTTCTTCA | TAACCATTAT | GGGATATTAT | TGCACACATA | 1320 |
| AATGATTCGA | TTACCGGGGG | GGCAGAACGT | GTCTCATTTA | TATAAAGAGA | ATCACATACA | 1380 |
| TCGCTTATAG | AACATGTAGA | ACTGTCAGAA | TCCTCTTTAA | AACTATTTTT | AATTTCACAA | 1440 |
| TTAGTTTCTT | CTAGTTCATT | ATCCACCATC | GCATTAGCGT | ATTTCCAAAT | ATCATTCTCT | 1500 |
| GAGGAATAAT | GAGATGCAGA | GCATGAAGAA | GAGGATGAGG | AGGAGGAGGA | TGAAGATGAG | 1560 |
| GATATAGAGG | GACATCTTGG | AGAGCTTTCA | AAGTTGAATG | GAGTATTAAA | TGTTGTACCA | 1620 |
| TAAAAAATGT | CACTTAACAT | AGGGGGTACT | TTAAAGGAGG | ACAGAAAGGT | GTCTAATACA | 1680 |
| GGTACCCATA | TAAACGAGGG | GCAATAAACA | CTCCCAGAAT | CATCGATATG | TTTTACATTA | 1740 |
| TTTTTGGAAA | TCTCAAGACA | CTCAGGTTTC | CAGGATGGTT | CCGGCCATTC | ACATGATACA | 1800 |
| TATGCATAAA | TTAGTCGCTT | TGGTCCTGGG | ATATTAGAAA | TGACTGGCTC | ACATAAATCC | 1860 |
| GCTGCACCGA | AAACCCATAG | ATTAAGAGGA | TAGTTTCCAA | ATATACCAGA | GTTTAGATAG | 1920 |
| TTATACCCCG | AAACAGCCGA | TTTCCATTCG | ATGCTAGCCC | CAGGTTTATC | CTCATAAAAT | 1980 |
| AAAAAGTCCT | CCTCCTCCCC | CTCCGTTGGT | TTTAAAAATT | TACTATTAGA | GGTTGATGTT | 2040 |
| CTTACTATAG | GCCTTGAAAC | TCTAGGTAGA | TGTTTTATAG | AGTCCATAAA | ATAACATAAG | 2100 |

```
TTTGCAGATC  GTAATATTAT  AGGCATAGCC  AATCGTGTGA  GAGAAAGGAT  ATAGCATTGT   2160
CTAGCCATAA  AACACCAAAG  ATCAGGATGA  ACATCTTGGG  AGTTTCCTGG  TAACGCCCCA   2220
TTTTTGTCAA  TAAACGTAAC  AATATTAACT  TCAACCACAC  CCATAATTAA  ATTTTATGTA   2280
TGAATCCAAT  AAAGGTTAAT  ACACACCTAA  TTTATGTTAT  AATTTAGAA   GAAGCTGCAG   2340
TTGATGAGTT  GATATTAACA  TAACAATTTC  ACAATTACCT  GATATGGCAA  AGTGTACCAC   2400
CGAAAAGTTT  TGTTGTATCA  GCGTGAATAG  AGAATCTTCT  GTCGATCCAG  AAGACTTCTA   2460
TAAACCGGTT  CCTCTAACTT  CAGATTTGAT  TGAAGAGGAT  AACCTACATC  AAGACAAAAT   2520
AATGGATGAG  GATTTATACT  CGGATTTTAG  TGATGATGAC  TTTATGGATT  ATACAAAAAA   2580
TCCAACTGAA  AGTGAAAATG  AAAGAGAAAG  TGACGAAGAA  GTTGAAGAAA  GTTATGAAAG   2640
TGATGAAGAT  AAAAAAGTT   TATCTCCTAC  TAAAAGCGAA  GGAATTGAAG  CGGCTGAAGC   2700
GCTAAAGTTT  TCTGTTGTTA  AATCGTTAAC  GCCTGGGTCA  GAAGGAAGAG  TTTTTATTGC   2760
TCTTAAAAAA  GATAAAGATA  CAAGCTATAA  GGTAATTTTA  AAAATTGGAC  AAAGGGGAAA   2820
CACGCTTGTG  GAATCGTTAA  TTTGAGAAA   TATTAGTCAC  CAATCTATAA  TTAAACTTCA   2880
AGACACTCTT  TTTTATAAAG  AGTTAACATG  TTTGGTGTTA  CCGTATTATA  AATATGATCT   2940
ATATAATTTT  TTAATGGATC  ATGGGAAATC  TCTGTCTTTT  GAATCTGTAA  TTAAAATTGA   3000
AAAACAAATA  TTAACTGGAC  TTCAATATAT  TCATGGAAAA  AAAATTATTC  ATCGAGATAT   3060
AAAAACTGAA  ATATTTTCT   TGGATAATGA  CTCTAATGTT  TGTATAGGTG  ATTTGGGGC    3120
TTCTCAATTT  CCTGTTTCCT  CACCAGATTA  TTTGGGAATT  GCGGGGACTA  TTGAAACTAA   3180
TGCTCCTGAA  GTTCTATCAA  AGGATGCGTA  CAACTGTAAA  GCTGATATTT  GGAGTGCTGG   3240
TATAATTTA   TTTGAAATGC  TTGCATATCC  TAATGTTTTG  TTTGAGGAGG  AAGAAAGAGA   3300
TAGTAGCGAT  TTAATAAACA  ATTGTAATCT  TCATCTTATA  AAAATTATAT  CAACTCTGAA   3360
GATTAACCCA  AATGAATTTC  CATCTGATTT  GGAATCTAAT  CTAGTAAAAC  ATTTTATAAA   3420
ATATGCTAAT  AATGATAGAC  CTCCATTTAC  ACGATATAAT  CGTCTAAATA  ACCTTAAATT   3480
ACATCTCGAT  GGTGAATTTT  TAATTCATAA  AATGCTAACA  TTTGATGCAT  CTCTACGACC   3540
AAGTGCGGAA  GAACTATTAT  CCTATCAGAT  TTTTAGTAAA  CAATAAATTT  CATAAAAATG   3600
GGCGTGGAAT  TTTTTATTGT  TTTATATAAA  ACGGGTGTTT  GAAAGCTCTT  TTTTATTAAT   3660
TTTATTTTA   CATCCTAGCT  ACAATATTAT  AGTTATCATG  TTGTATACGC  TGTTTTTTGT   3720
TTTTTATTTT  AAGGTAGTTT  TATCTCGCAT  AGCTCCGCTA  GAGTTGTGTT  ATGCGGATCC   3780
TAAAGAAAAT  ACAACTGAAC  CTACACAACT  TCCTACAGGG  AACAATCTA   AGACTCTTAT   3840
TCCCGTGGTA  ACAAACGGAT  ATGTTGAATA  CTCTAAAGGA  TGTGAACTAC  GATTACTAGA   3900
TACATATGTA  AATGTATCTT  CACGACCAGA  AAAAAAGGTT  AATGCTACAA  TTGGATGGTC   3960
ATTTGATCTT  GGTTGTCAAA  TTCCTTTAAT  TTATAGAGAA  TATTATAATT  GTACTGGTAA   4020
TATAATACCA  TCACCAGAAA  CTTGTGATGG  TTATTCTTTA  ACTTGGTAA   AATCTGAAAG   4080
TATATCATCT  TATGCACTTG  TTAATGTTAG  TTTGCTTATT  CAACCAGGAA  TTTTTGATTC   4140
TGGTAGATAT  TTATACTCAC  TTGTTTTTGG  AAACGATAGT  TATAACGGAA  GAATTGAAGT   4200
TCGAGTGGAT  AATGAGACAG  ACTATCCATG  TTTTATGATG  CATGGATTGA  CTGTAAAAAA   4260
GGGTGATAAA  CTTCATATTC  CTTATAAACC  ATCCACAAAT  CCTAATCATA  AACGATATAG   4320
AGGTTGTTTT  CCAATATCAA  ATACTGAGCT  ATGGAATAAT  ATTAGTGATG  AAAGTGTTGG   4380
TAGATATTCA  TATGATGAAG  AATATGAAGA  ATATGAAGAA  GAAAACGAAG  ATTTTGAAGA   4440
TCTACAATCA  AAAGATTGCC  GCAAATCCAA  TCTTTTTGAT  ATGAAGAAGA  CTTTTAATTT   4500
```

-continued

| | | | | | |
|---|---|---|---|---|---|
| GGCTGCAGGT | TCTCAAAGTT | TATTGATTGC | TAGTTTGGGT | AAATCAATTT | CAGAACAACC | 4560 |
| GTGGTCATTT | AAAATTAATG | AAAGTTATGA | ACTTTTTAAT | AATTTGTCTA | TCACCCTTCA | 4620 |
| ATCGGAAGAA | GATTCTAATA | TACTGAATCC | TGAAATTGTA | ACGTTACCA | CACCACCACC | 4680 |
| TACTGAAAAT | ACACATATGT | TTATGTCAAA | TAATGAAACT | ATGTATGAAG | AAGAAAGTGT | 4740 |
| TTAAGCATT | ATTCAATTGT | TTAACAATGG | TTATAATAAT | TGTAATACCC | ATATAAAGGT | 4800 |
| AATTGGATTT | GGAACAATTA | TCTTTATTAT | TTTATTTTTT | GTTGCTGTGT | TTTTTGTGG | 4860 |
| ATATACTTGT | GTATTAAACT | CTCGTATTAA | AATGATTAAC | CATGCTTATA | TACAACCCCA | 4920 |
| GAAATTAAAT | TTTTATGATA | TTTAATAAAA | CTATTATGAA | ACTTCTTATA | ACTTATTTGT | 4980 |
| TTTTATTAAA | TGGGTTGGGT | TGGTTTTAAA | ATTACATACG | TGTATTAAGA | ATTAACATCA | 5040 |
| TAAAGGACAC | ACCCATGAAA | AACATTTAAA | TTCTATTAAT | TTGAACGGAT | TAAACATTTT | 5100 |
| CTCATTTTAA | GAGTTGCTAC | GACTTTTGAT | AGTAAAATGA | TTAAACTTCT | ATTTATCTTA | 5160 |
| TTTTATTTTA | ACCCAATAAC | TGGATATAAA | TGGGTAGACC | CTCCTCGTAG | GTATAATTAC | 5220 |
| ACCGTTTTAA | GAATGATTCC | AGATATTCCA | AATCCAATGG | ATCCTTCTAA | AAACGCTGAA | 5280 |
| GTTCGGTATG | TAACTTCTAC | TGACCCATGT | GATATGGTTG | CTTTGATTTC | TAATCCAAAT | 5340 |
| ATAGAATCTA | CAATTAAAAC | GATTCAATTT | GTGCAAAAGA | AAAAATTTTA | CAATGCATCT | 5400 |
| CTTAGTTGGT | TTAAAGTTGG | AGATGATTGT | ACATATCCAA | TATATTTAAT | TCAATATTTT | 5460 |
| GATTGTGATC | CTCAAAGAGA | ATTGGCATA | TGTTT | | | 5495 |

( 2 ) INFORMATION FOR SEQ ID NO:2:

( i ) SEQUENCE CHARACTERISTICS:
        ( A ) LENGTH: 5495 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
| AAACATATGC | CAAATTCTCT | TTGAGGATCA | CAATCAAAAT | ATTGAATTAA | ATATATTGGA | 60 |
| TATGTACAAT | CATCTCCAAC | TTTAAACCAA | CTAAGAGATG | CATTGTAAAA | TTTTTTCTTT | 120 |
| TGCACAAATT | GAATCGTTTT | AATTGTAGAT | TCTATATTTG | GATTAGAAAT | CAAAGCAACC | 180 |
| ATATCACATG | GGTCAGTAGA | AGTTACATAC | CGAACTTCAG | CGTTTTTAGA | AGGATCCATT | 240 |
| GGATTTGGAA | TATCTGGAAT | CATTCTTAAA | ACGGTGTAAT | TATACCTACG | AGGAGGGTCT | 300 |
| ACCCATTTAT | ATCCAGTTAT | TGGGTTAAAA | TAAAATAAGA | TAAATAGAAG | TTTAATCATT | 360 |
| TTACTATCAA | AAGTCGTAGC | AACTCTTAAA | ATGAGAAAAT | GTTAATCCG | TTCAAATTAA | 420 |
| TAGAATTTAA | ATGTTTTTCA | TGGGTGTGTC | CTTTATGATG | TTAATTCTTA | ATACACGTAT | 480 |
| GTAATTTTAA | AACCAACCCA | ACCCATTTAA | TAAAACAAA | TAAGTTATAA | GAAGTTTCAT | 540 |
| AATAGTTTTA | TTAAATATCA | TAAAAATTTA | ATTTCTGGGG | TTGTATATAA | GCATGGTTAA | 600 |
| TCATTTTAAT | ACGAGAGTTT | AATACACAAG | TATATCCACA | AAAAACACA | GCAACAAAAA | 660 |
| ATAAATAAT | AAAGATAATT | GTTCCAAATC | CAATTACCTT | TATATGGGTA | TTACAATTAT | 720 |
| TATAACCATT | GTTAAACAAT | TGAATAATGC | TTAAAACACT | TTCTTCTTCA | TACATAGTTT | 780 |
| CATTATTTGA | CATAAACATA | TGTGTATTTT | CAGTAGGTGG | TGGTGTGGTA | AACGTTACAA | 840 |
| TTTCAGGATT | CAGTATATTA | GAATCTTCTT | CCGATTGAAG | GGTGATAGAC | AAATTATTAA | 900 |
| AAAGTTCATA | ACTTTCATTA | ATTTTAAATG | ACCACGGTTG | TTCTGAAATT | GATTTACCCA | 960 |

```
AACTAGCAAT CAATAAACTT TGAGAACCTG CAGCCAAATT AAAAGTCTTC TTCATATCAA   1020
AAAGATTGGA TTTGCGGCAA TCTTTTGATT GTAGATCTTC AAAATCTTCG TTTTCTTCTT   1080
CATATTCTTC ATATTCTTCA TCATATGAAT ATCTACCAAC ACTTTCATCA CTAATATTAT   1140
TCCATAGCTC AGTATTTGAT ATTGGAAAAC AACCTCTATA TCGTTATGA TTAGGATTTG   1200
TGGATGGTTT ATAAGGAATA TGAAGTTTAT CACCCTTTTT TACAGTCAAT CCATGCATCA   1260
TAAAACATGG ATAGTCTGTC TCATTATCCA CTCGAACTTC AATTCTTCCG TTATAACTAT   1320
CGTTTCCAAA AACAAGTGAG TATAAATATC TACCAGAATC AAAAATTCCT GGTTGAATAA   1380
GCAAACTAAC ATTAACAAGT GCATAAGATG ATATACTTTC AGATTTTACC AAAGTTAAAG   1440
AATAACCATC ACAAGTTTCT GGTGATGGTA TTATATTACC AGTACAATTA TAATATTCTC   1500
TATAAATTAA AGGAATTTGA CAACCAAGAT CAAATGACCA TCCAATTGTA GCATTAACCT   1560
TTTTTTCTGG TCGTGAAGAT ACATTTACAT ATGTATCTAG TAATCGTAGT TCACATCCTT   1620
TAGAGTATTC AACATATCCG TTTGTTACCA CGGGAATAAG AGTCTTAGAT TGTTCCCCTG   1680
TAGGAAGTTG TGTAGGTTCA GTTGTATTTT CTTAGGATC CGCATAACAC AACTCTAGCG   1740
GAGCTATGCG AGATAAAACT ACCTTAAAAT AAAAACAAA AACAGCGTA TACAACATGA     1800
TAACTATAAT ATTGTAGCTA GGATGTAAAA ATAAAATTAA TAAAAAGAG CTTTCAAACA    1860
CCCGTTTTAT ATAAAACAAT AAAAAATTCC ACGCCCATTT TTATGAAATT TATTGTTTAC   1920
TAAAAATCTG ATAGGATAAT AGTTCTTCCG CACTTGGTCG TAGAGATGCA TCAAATGTTA   1980
GCATTTATG AATTAAAAAT TCACCATCGA GATGTAATTT AAGGTTATTT AGACGATTAT    2040
ATCGTGTAAA TGGAGGTCTA TCATTATTAG CATATTTTAT AAAATGTTTT ACTAGATTAG   2100
ATTCCAAATC AGATGGAAAT TCATTGGGT TAATCTTCAG AGTTGATATA ATTTTATAA     2160
GATGAAGATT ACAATTGTTT ATTAAATCGC TACTATCTCT TTCTTCCTCC TCAAACAAAA   2220
CATTAGGATA TGCAAGCATT TCAAATAAAA TTATACCAGC ACTCCAAATA TCAGCTTTAC   2280
AGTTGTACGC ATCCTTGAT AGAACTTCAG GAGCATTAGT TTCAATAGTC CCCGCAATTC    2340
CCAAATAATC TGGTGAGGAA ACAGGAAATT GAGAAGCCCC AAAATCACCT ATACAAACAT   2400
TAGAGTCATT ATCCAAGAAA ATATTTCAG TTTTTATATC TCGATGAATA ATTTTTTTC     2460
CATGAATATA TTGAAGTCCA GTTAATATTT GTTTTCAAT TTAATTACA GATTCAAAAG     2520
ACAGAGATTT CCCATGATCC ATTAAAAAAT TATATAGATC ATATTTATAA TACGGTAACA   2580
CCAAACATGT TAACTCTTTA TAAAAAGAG TGTCTTGAAG TTTAATTATA GATTGGTGAC    2640
TAATATTTCT CAAAATTAAC GATTCCACAA GCGTGTTTCC CCTTTGTCCA ATTTTAAAA    2700
TTACCTTATA GCTTGTATCT TTATCTTTTT TAAGAGCAAT AAAAACTCTT CCTTCTGACC   2760
CAGGCGTTAA CGATTTAACA ACAGAAAACT TTAGCGCTTC AGCCGCTTCA ATTCCTTCGC   2820
TTTTAGTAGG AGATAAACTT TTTTATCTT CATCACTTTC ATAACTTTCT TCAACTTCTT    2880
CGTCACTTTC TCTTTCATTT TCACTTTCAG TTGGATTTTT TGTATAATCC ATAAAGTCAT   2940
CATCACTAAA ATCCGAGTAT AAATCCTCAT CCATTATTTT GTCTTGATGT AGGTTATCCT   3000
CTTCAATCAA ATCTGAAGTT AGAGGAACCG GTTATAGAA GTCTTCTGGA TCGACAGAAG    3060
ATTCTCTATT CACGCTGATA CAACAAAACT TTCGGTGGT ACACTTTGCC ATATCAGGTA    3120
ATTGTGAAAT TGTTATGTTA ATATCAACTC ATCAACTGCA GCTTCTTCTA AAATTATAAC   3180
ATAAATTAGG TGTGTATTAA CCTTTATTGG ATTCATACAT AAAATTTAAT TATGGGTGTG   3240
GTTGAAGTTA ATATTGTTAC GTTATTGAC AAAAATGGGG CGTTACCAGG AAACTCCCAA    3300
GATGTTCATC CTGATCTTTG GTGTTTTATG GCTAGACAAT GCTATATCCT TTCTCTCACA   3360
```

-continued

```
CGATTGGCTA TGCCTATAAT ATTACGATCT GCAAACTTAT GTTATTTTAT GGACTCTATA    3420
AAACATCTAC CTAGAGTTTC AAGGCCTATA GTAAGAACAT CAACCTCTAA TAGTAAATTT    3480
TTAAAACCAA CGGAGGGGGA GGAGGAGGAC TTTTTATTTT ATGAGGATAA ACCTGGGGCT    3540
AGCATCGAAT GGAAATCGGC TGTTTCGGGG TATAACTATC TAAACTCTGG TATATTGGA     3600
AACTATCCTC TTAATCTATG GGTTTTCGGT GCAGCGGATT TATGTGAGCC AGTCATTTCT    3660
AATATCCCAG GACCAAAGCG ACTAATTTAT GCATATGTAT CATGTGAATG GCCGGAACCA    3720
TCCTGGAAAC CTGAGTGTCT TGAGATTTCC AAAAATAATG TAAAACATAT CGATGATTCT    3780
GGGAGTGTTT ATTGCCCCTC GTTATATGG GTACCTGTAT TAGACACCTT TCTGTCCTCC     3840
TTTAAAGTAC CCCCTATGTT AAGTGACATT TTTTATGGTA CAACATTTAA TACTCCATTC    3900
AACTTTGAAA GCTCTCCAAG ATGTCCCTCT ATATCCTCAT CTTCATCCTC CTCCTCCTCA    3960
TCCTCTTCTT CATGCTCTGC ATCTCATTAT TCCTCAGAGA ATGATATTTG GAAATACGCT    4020
AATGCGATGG TGGATAATGA ACTAGAAGAA ACTAATTGTG AAATTAAAAA TAGTTTTAAA    4080
GAGGATTCTG ACAGTTCTAC ATGTTCTATA AGCGATGTAT GTGATTCTCT TTATATAAAT    4140
GAGACACGTT CTGCCCCCCC GGTAATCGAA TCATTTATGT GTGCAATAAT ATCCCATAAT    4200
GGTTATGAAG AAATTCCTGA ACCAGAAGAG GATGACTTGC ATGGGGTGAA ACCTATGAAA    4260
AGGCTATCCA AACCAAATAT TTTTAAACGA TTATTTTCAA GGCGCGCCAA AACAATAACC    4320
AAAAATGAAA ACGATGGTAT GTCTTCTACA CAACCTACCA ACGCTCAACG TTCATCTCTA    4380
TTTAGTTCAT GTTTATGTGG AAACTAAGTT TGTTTATATT TGTTGTGAAT AAACAGTAGA    4440
TGTAAACCTG AAATTCTGGT TTTTTATGTG AACCACTCCC ATATTCTTAC TGTATATAAA    4500
CTGGCATTTT ATCCTACATT TTTAAATCTT CACTTGTTTT TAAAGCTTAA CTAAAAAGTT    4560
TTAAAATGAG TGCTTCATTT GCTCTATTTG ATAACAACTC CGATCAAGCT AATATGCCAT    4620
CATACTTCAG ACGCTGTCGT GGAGAACTTA ATGAAGGATT CTACGCACAA GTTCCGCCTG    4680
GTTATTTTCC AGTTCGCCCT AAAACCACAC CAGCGCTTGC ACGTGTGAAA AACCAGGGTG    4740
AACCGCACGC CTTCACTATT GTTCCTACAC CACCTACGGA TGTACGATTC TTCAAAAAGC    4800
TTCGTGATGG AACCTTTGTG AAACTTCCAT TTTCATATCC TGATGAGAGG TATGAAGATG    4860
ATATTGAACC TATGTATTGC AGACTATACG TTCTAAGGA TTTTGAAACG CCAAGTTCTC     4920
CCTACAATCA AGTAAACGCT TCTCAGCTTA TGGAAGTACC TTCTTCGCTT GTGGAATCGA    4980
AGTGTTATTG GGATGGTCCA AAATTTATAA ATGTACCACC AATAAGATAT ATTCTAAAAA    5040
GTGATTACTC TCTTAAAATA AATGTATCCG AAGATGCATT TGTGTTGGGT AGGATACCAG    5100
AAAAACTAAA AACTTGAAAA ACTAAAAATG TTTACCCAAC CGCCTACTGT ACTTAACCTT    5160
ATAAATTTAA AATATTTTTA AAATACTTGT CTCATAGATT TCATTCATAG ATTTCATTCA    5220
TAGATTTCAT TCATAGATTT CATTCATAGA TTTCATTCAT AGATTTCATT CATAGATTTC    5280
ATTCATAGAT TTCATTCATA GATTTCATTC ATAGATTTCA TTCATAGATT TCATTCATAG    5340
ATTTCATTCA TAGATTTCAT TCATAGATTT CATTCATAGA TTTCATTCAT AGATTTCATT    5400
CATAGATTTC ATTCATAGAT TCATTCATA GATTTCATTC ATAGATTTCA TTCATAGATT     5460
TCATTCATAG ATTTTATTTT TTAAATACAC TGCAG                                5495
```

( 2 ) INFORMATION FOR SEQ ID NO:3:

( i ) SEQUENCE CHARACTERISTICS:
        ( A ) LENGTH: 552 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 1..552

( x i ) SEQUENCE DESCRIPTION: SEQ ID NO:3:

| ATG | AGT | GCT | TCA | TTT | GCT | CTA | TTT | GAT | AAC | AAC | TCC | GAT | CAA | GCT | AAT | 48 |
| Met | Ser | Ala | Ser | Phe | Ala | Leu | Phe | Asp | Asn | Asn | Ser | Asp | Gln | Ala | Asn | |
| 1 | | | | 5 | | | | | 10 | | | | | 15 | | |

| ATG | CCA | TCA | TAC | TTC | AGA | CGC | TGT | CGT | GGA | GAA | CTT | AAT | GAA | GGA | TTC | 96 |
| Met | Pro | Ser | Tyr | Phe | Arg | Arg | Cys | Arg | Gly | Glu | Leu | Asn | Glu | Gly | Phe | |
| | | | 20 | | | | 25 | | | | | 30 | | | | |

| TAC | GCA | CAA | GTT | CCG | CCT | GGT | TAT | TTT | CCA | GTT | CGC | CCT | AAA | ACC | ACA | 144 |
| Tyr | Ala | Gln | Val | Pro | Pro | Gly | Tyr | Phe | Pro | Val | Arg | Pro | Lys | Thr | Thr | |
| | | 35 | | | | 40 | | | | | 45 | | | | | |

| CCA | GCG | CTT | GCA | CGT | GTG | AAA | AAC | CAG | GGT | GAA | CCG | CAC | GCC | TTC | ACT | 192 |
| Pro | Ala | Leu | Ala | Arg | Val | Lys | Asn | Gln | Gly | Glu | Pro | His | Ala | Phe | Thr | |
| | 50 | | | | | 55 | | | | | 60 | | | | | |

| ATT | GTT | CCT | ACA | CCA | CCT | ACG | GAT | GTA | CGA | TTC | TTC | AAA | AAG | CTT | CGT | 240 |
| Ile | Val | Pro | Thr | Pro | Pro | Thr | Asp | Val | Arg | Phe | Phe | Lys | Lys | Leu | Arg | |
| 65 | | | | | 70 | | | | | 75 | | | | | 80 | |

| GAT | GGA | ACC | TTT | GTG | AAA | CTT | CCA | TTT | TCA | TAT | CCT | GAT | GAG | AGG | TAT | 288 |
| Asp | Gly | Thr | Phe | Val | Lys | Leu | Pro | Phe | Ser | Tyr | Pro | Asp | Glu | Arg | Tyr | |
| | | | | 85 | | | | | 90 | | | | | 95 | | |

| GAA | GAT | GAT | ATT | GAA | CCT | ATG | TAT | TGC | AGA | CTA | TAC | GTT | CTA | AAG | GAT | 336 |
| Glu | Asp | Asp | Ile | Glu | Pro | Met | Tyr | Cys | Arg | Leu | Tyr | Val | Leu | Lys | Asp | |
| | | | 100 | | | | | 105 | | | | | 110 | | | |

| TTT | GAA | ACG | CCA | AGT | TCT | CCC | TAC | AAT | CAA | GTA | AAC | GCT | TCT | CAG | CTT | 384 |
| Phe | Glu | Thr | Pro | Ser | Ser | Pro | Tyr | Asn | Gln | Val | Asn | Ala | Ser | Gln | Leu | |
| | | 115 | | | | | 120 | | | | | 125 | | | | |

| ATG | GAA | GTA | CCT | TCT | TCG | CTT | GTG | GAA | TCG | AAG | TGT | TAT | TGG | GAT | GGT | 432 |
| Met | Glu | Val | Pro | Ser | Ser | Leu | Val | Glu | Ser | Lys | Cys | Tyr | Trp | Asp | Gly | |
| | 130 | | | | | 135 | | | | | 140 | | | | | |

| CCA | AAA | TTT | ATA | AAT | GTA | CCA | CCA | ATA | AGA | TAT | ATT | CTA | AAA | AGT | GAT | 480 |
| Pro | Lys | Phe | Ile | Asn | Val | Pro | Pro | Ile | Arg | Tyr | Ile | Leu | Lys | Ser | Asp | |
| 145 | | | | | 150 | | | | | 155 | | | | | 160 | |

| TAC | TCT | CTT | AAA | ATA | AAT | GTA | TCC | GAA | GAT | GCA | TTT | GTG | TTG | GGT | AGG | 528 |
| Tyr | Ser | Leu | Lys | Ile | Asn | Val | Ser | Glu | Asp | Ala | Phe | Val | Leu | Gly | Arg | |
| | | | | 165 | | | | | 170 | | | | | 175 | | |

| ATA | CCA | GAA | AAA | CTA | AAA | ACT | TGA | | | | | | | | | 552 |
| Ile | Pro | Glu | Lys | Leu | Lys | Thr | * | | | | | | | | | |
| | | | 180 | | | | | | | | | | | | | |

( 2 ) INFORMATION FOR SEQ ID NO:4:

( i ) SEQUENCE CHARACTERISTICS:
        ( A ) LENGTH: 183 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ser | Ala | Ser | Phe | Ala | Leu | Phe | Asp | Asn | Asn | Ser | Asp | Gln | Ala | Asn |
| 1 | | | | 5 | | | | | 10 | | | | | 15 | |

| Met | Pro | Ser | Tyr | Phe | Arg | Arg | Cys | Arg | Gly | Glu | Leu | Asn | Glu | Gly | Phe |
| | | | 20 | | | | 25 | | | | | 30 | | | |

| Tyr | Ala | Gln | Val | Pro | Pro | Gly | Tyr | Phe | Pro | Val | Arg | Pro | Lys | Thr | Thr |
| | | 35 | | | | 40 | | | | | 45 | | | | |

| Pro | Ala | Leu | Ala | Arg | Val | Lys | Asn | Gln | Gly | Glu | Pro | His | Ala | Phe | Thr |
| | 50 | | | | | 55 | | | | | 60 | | | | |

```
Ile  Val  Pro  Thr  Pro  Pro  Thr  Asp  Val  Arg  Phe  Phe  Lys  Lys  Leu  Arg
65             70                       75                       80

Asp  Gly  Thr  Phe  Val  Lys  Leu  Pro  Phe  Ser  Tyr  Pro  Asp  Glu  Arg  Tyr
                    85                  90                       95

Glu  Asp  Asp  Ile  Glu  Pro  Met  Tyr  Cys  Arg  Leu  Tyr  Val  Leu  Lys  Asp
               100                     105                      110

Phe  Glu  Thr  Pro  Ser  Ser  Pro  Tyr  Asn  Gln  Val  Asn  Ala  Ser  Gln  Leu
          115                      120                       125

Met  Glu  Val  Pro  Ser  Ser  Leu  Val  Glu  Ser  Lys  Cys  Tyr  Trp  Asp  Gly
     130                     135                  140

Pro  Lys  Phe  Ile  Asn  Val  Pro  Pro  Ile  Arg  Tyr  Ile  Leu  Lys  Ser  Asp
145                      150                 155                       160

Tyr  Ser  Leu  Lys  Ile  Asn  Val  Ser  Glu  Asp  Ala  Phe  Val  Leu  Gly  Arg
                    165                      170                      175

Ile  Pro  Glu  Lys  Leu  Lys  Thr
                    180
```

( 2 ) INFORMATION FOR SEQ ID NO:5:

( i ) SEQUENCE CHARACTERISTICS:
        ( A ) LENGTH: 1176 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1176

( x i ) SEQUENCE DESCRIPTION: SEQ ID NO:5:

```
ATG  GGT  GTG  GTT  GAA  GTT  AAT  ATT  GTT  ACG  TTT  ATT  GAC  AAA  AAT  GGG       48
Met  Gly  Val  Val  Glu  Val  Asn  Ile  Val  Thr  Phe  Ile  Asp  Lys  Asn  Gly
1                   5                        10                      15

GCG  TTA  CCA  GGA  AAC  TCC  CAA  GAT  GTT  CAT  CCT  GAT  CTT  TGG  TGT  TTT       96
Ala  Leu  Pro  Gly  Asn  Ser  Gln  Asp  Val  His  Pro  Asp  Leu  Trp  Cys  Phe
                    20                       25                      30

ATG  GCT  AGA  CAA  TGC  TAT  ATC  CTT  TCT  CTC  ACA  CGA  TTG  GCT  ATG  CCT      144
Met  Ala  Arg  Gln  Cys  Tyr  Ile  Leu  Ser  Leu  Thr  Arg  Leu  Ala  Met  Pro
          35                       40                       45

ATA  ATA  TTA  CGA  TCT  GCA  AAC  TTA  TGT  TAT  TTT  ATG  GAC  TCT  ATA  AAA      192
Ile  Ile  Leu  Arg  Ser  Ala  Asn  Leu  Cys  Tyr  Phe  Met  Asp  Ser  Ile  Lys
50                       55                       60

CAT  CTA  CCT  AGA  GTT  TCA  AGG  CCT  ATA  GTA  AGA  ACA  TCA  ACC  TCT  AAT      240
His  Leu  Pro  Arg  Val  Ser  Arg  Pro  Ile  Val  Arg  Thr  Ser  Thr  Ser  Asn
65                  70                       75                       80

AGT  AAA  TTT  TTA  AAA  CCA  ACG  GAG  GGG  GAG  GAG  GAG  GAC  TTT  TTA  TTT      288
Ser  Lys  Phe  Leu  Lys  Pro  Thr  Glu  Gly  Glu  Glu  Glu  Asp  Phe  Leu  Phe
                    85                       90                      95

TAT  GAG  GAT  AAA  CCT  GGG  GCT  AGC  ATC  GAA  TGG  AAA  TCG  GCT  GTT  TCG      336
Tyr  Glu  Asp  Lys  Pro  Gly  Ala  Ser  Ile  Glu  Trp  Lys  Ser  Ala  Val  Ser
               100                      105                      110

GGG  TAT  AAC  TAT  CTA  AAC  TCT  GGT  ATA  TTT  GGA  AAC  TAT  CCT  CTT  AAT      384
Gly  Tyr  Asn  Tyr  Leu  Asn  Ser  Gly  Ile  Phe  Gly  Asn  Tyr  Pro  Leu  Asn
          115                      120                      125

CTA  TGG  GTT  TTC  GGT  GCA  GCG  GAT  TTA  TGT  GAG  CCA  GTC  ATT  TCT  AAT      432
Leu  Trp  Val  Phe  Gly  Ala  Ala  Asp  Leu  Cys  Glu  Pro  Val  Ile  Ser  Asn
     130                     135                      140

ATC  CCA  GGA  CCA  AAG  CGA  CTA  ATT  TAT  GCA  TAT  GTA  TCA  TGT  GAA  TGG      480
Ile  Pro  Gly  Pro  Lys  Arg  Leu  Ile  Tyr  Ala  Tyr  Val  Ser  Cys  Glu  Trp
```

|  145 |  |  | 150 |  |  |  | 155 |  |  |  | 160 |  |  |  |  |
|---|---|---|---|---|---|---|---|---|---|---|---|---|---|---|---|
| CCG | GAA | CCA | TCC | TGG | AAA | CCT | GAG | TGT | CTT | GAG | ATT | TCC | AAA | AAT | AAT | 528 |
| Pro | Glu | Pro | Ser | Trp 165 | Lys | Pro | Glu | Cys 170 | Leu | Glu | Ile | Ser | Lys 175 | Asn | Asn | |
| GTA | AAA | CAT | ATC | GAT | GAT | TCT | GGG | AGT | GTT | TAT | TGC | CCC | TCG | TTT | ATA | 576 |
| Val | Lys | His | Ile 180 | Asp | Asp | Ser | Gly | Ser 185 | Val | Tyr | Cys | Pro | Ser 190 | Phe | Ile | |
| TGG | GTA | CCT | GTA | TTA | GAC | ACC | TTT | CTG | TCC | TCC | TTT | AAA | GTA | CCC | CCT | 624 |
| Trp | Val | Pro 195 | Val | Leu | Asp | Thr | Phe 200 | Leu | Ser | Ser | Phe | Lys 205 | Val | Pro | Pro | |
| ATG | TTA | AGT | GAC | ATT | TTT | TAT | GGT | ACA | ACA | TTT | AAT | ACT | CCA | TTC | AAC | 672 |
| Met | Leu 210 | Ser | Asp | Ile | Phe | Tyr 215 | Gly | Thr | Thr | Phe | Asn 220 | Thr | Pro | Phe | Asn | |
| TTT | GAA | AGC | TCT | CCA | AGA | TGT | CCC | TCT | ATA | TCC | TCA | TCT | TCA | TCC | TCC | 720 |
| Phe 225 | Glu | Ser | Ser | Pro | Arg 230 | Cys | Pro | Ser | Ile 235 | Ser | Ser | Ser | Ser | Ser 240 | Ser | |
| TCC | TCC | TCA | TCC | TCT | TCT | TCA | TGC | TCT | GCA | TCT | CAT | TAT | TCC | TCA | GAG | 768 |
| Ser | Ser | Ser | Ser | Ser 245 | Ser | Ser | Cys | Ser | Ala 250 | Ser | His | Tyr | Ser | Ser 255 | Glu | |
| AAT | GAT | ATT | TGG | AAA | TAC | GCT | AAT | GCG | ATG | GTG | GAT | AAT | GAA | CTA | GAA | 816 |
| Asn | Asp | Ile | Trp 260 | Lys | Tyr | Ala | Asn | Ala 265 | Met | Val | Asp | Asn | Glu 270 | Leu | Glu | |
| GAA | ACT | AAT | TGT | GAA | ATT | AAA | AAT | AGT | TTT | AAA | GAG | GAT | TCT | GAC | AGT | 864 |
| Glu | Thr | Asn 275 | Cys | Glu | Ile | Lys | Asn 280 | Ser | Phe | Lys | Glu | Asp 285 | Ser | Asp | Ser | |
| TCT | ACA | TGT | TCT | ATA | AGC | GAT | GTA | TGT | GAT | TCT | CTT | TAT | ATA | AAT | GAG | 912 |
| Ser | Thr 290 | Cys | Ser | Ile | Ser | Asp 295 | Val | Cys | Asp | Ser | Leu 300 | Tyr | Ile | Asn | Glu | |
| ACA | CGT | TCT | GCC | CCC | CCG | GTA | ATC | GAA | TCA | TTT | ATG | TGT | GCA | ATA | ATA | 960 |
| Thr 305 | Arg | Ser | Ala | Pro | Pro 310 | Val | Ile | Glu | Ser | Phe 315 | Met | Cys | Ala | Ile | Ile 320 | |
| TCC | CAT | AAT | GGT | TAT | GAA | GAA | ATT | CCT | GAA | CCA | GAA | GAG | GAT | GAC | TTG | 1008 |
| Ser | His | Asn | Gly | Tyr 325 | Glu | Glu | Ile | Pro | Glu 330 | Pro | Glu | Glu | Asp | Asp 335 | Leu | |
| CAT | GGG | GTG | AAA | CCT | ATG | AAA | AGG | CTA | TCC | AAA | CCA | AAT | ATT | TTT | AAA | 1056 |
| His | Gly | Val | Lys 340 | Pro | Met | Lys | Arg | Leu 345 | Ser | Lys | Pro | Asn | Ile 350 | Phe | Lys | |
| CGA | TTA | TTT | TCA | AGG | CGC | GCC | AAA | ACA | ATA | ACC | AAA | AAT | GAA | AAC | GAT | 1104 |
| Arg | Leu | Phe 355 | Ser | Arg | Arg | Ala | Lys 360 | Thr | Ile | Thr | Lys | Asn 365 | Glu | Asn | Asp | |
| GGT | ATG | TCT | TCT | ACA | CAA | CCT | ACC | AAC | GCT | CAA | CGT | TCA | TCT | CTA | TTT | 1152 |
| Gly | Met | Ser | Ser 370 | Thr | Gln | Pro | Thr | Asn 375 | Ala | Gln | Arg | Ser | Ser 380 | Leu | Phe | |
| AGT | TCA | TGT | TTA | TGT | GGA | AAC | TAA |  |  |  |  |  |  |  |  | 1176 |
| Ser 385 | Ser | Cys | Leu | Cys | Gly 390 | Asn | * |  |  |  |  |  |  |  |  | |

( 2 ) INFORMATION FOR SEQ ID NO:6:

( i ) SEQUENCE CHARACTERISTICS:
( A ) LENGTH: 391 amino acids
( B ) TYPE: amino acid
( D ) TOPOLOGY: linear ( i i ) MOLECULE TYPE: protein ( x i ) SEQUENCE DESCRIPTION: SEQ ID NO:6:

| Met | Gly | Val | Val | Glu | Val | Asn | Ile | Val | Thr | Phe | Ile | Asp | Lys | Asn | Gly |
|---|---|---|---|---|---|---|---|---|---|---|---|---|---|---|---|
| 1 |  |  |  | 5 |  |  |  |  | 10 |  |  |  |  | 15 |  |
| Ala | Leu | Pro | Gly | Asn | Ser | Gln | Asp | Val | His | Pro | Asp | Leu | Trp | Cys | Phe |
|  |  |  | 20 |  |  |  |  | 25 |  |  |  |  | 30 |  |  |

```
Met Ala Arg Gln Cys Tyr Ile Leu Ser Leu Thr Arg Leu Ala Met Pro
         35                      40                  45
Ile Ile Leu Arg Ser Ala Asn Leu Cys Tyr Phe Met Asp Ser Ile Lys
     50                  55                  60
His Leu Pro Arg Val Ser Arg Pro Ile Val Arg Thr Ser Thr Ser Asn
 65                  70                  75                   80
Ser Lys Phe Leu Lys Pro Thr Glu Gly Glu Glu Asp Phe Leu Phe
                 85                  90                  95
Tyr Glu Asp Lys Pro Gly Ala Ser Ile Glu Trp Lys Ser Ala Val Ser
             100                 105                 110
Gly Tyr Asn Tyr Leu Asn Ser Gly Ile Phe Gly Asn Tyr Pro Leu Asn
         115                 120                 125
Leu Trp Val Phe Gly Ala Ala Asp Leu Cys Glu Pro Val Ile Ser Asn
     130                 135                 140
Ile Pro Gly Pro Lys Arg Leu Ile Tyr Ala Tyr Val Ser Cys Glu Trp
 145                 150                 155                 160
Pro Glu Pro Ser Trp Lys Pro Glu Cys Leu Glu Ile Ser Lys Asn Asn
                 165                 170                 175
Val Lys His Ile Asp Asp Ser Gly Ser Val Tyr Cys Pro Ser Phe Ile
             180                 185                 190
Trp Val Pro Val Leu Asp Thr Phe Leu Ser Ser Phe Lys Val Pro Pro
         195                 200                 205
Met Leu Ser Asp Ile Phe Tyr Gly Thr Thr Phe Asn Thr Pro Phe Asn
     210                 215                 220
Phe Glu Ser Ser Pro Arg Cys Pro Ser Ile Ser Ser Ser Ser Ser Ser
 225                 230                 235                 240
Ser Ser Ser Ser Ser Ser Ser Cys Ser Ala Ser His Tyr Ser Ser Glu
                 245                 250                 255
Asn Asp Ile Trp Lys Tyr Ala Asn Ala Met Val Asp Asn Glu Leu Glu
             260                 265                 270
Glu Thr Asn Cys Glu Ile Lys Asn Ser Phe Lys Glu Asp Ser Asp Ser
         275                 280                 285
Ser Thr Cys Ser Ile Ser Asp Val Cys Asp Ser Leu Tyr Ile Asn Glu
     290                 295                 300
Thr Arg Ser Ala Pro Pro Val Ile Glu Ser Phe Met Cys Ala Ile Ile
 305                 310                 315                 320
Ser His Asn Gly Tyr Glu Glu Ile Pro Glu Pro Glu Glu Asp Asp Leu
                 325                 330                 335
His Gly Val Lys Pro Met Lys Arg Leu Ser Lys Pro Asn Ile Phe Lys
             340                 345                 350
Arg Leu Phe Ser Arg Arg Ala Lys Thr Ile Thr Lys Asn Glu Asn Asp
         355                 360                 365
Gly Met Ser Ser Thr Gln Pro Thr Asn Ala Gln Arg Ser Ser Leu Phe
     370                 375                 380
Ser Ser Cys Leu Cys Gly Asn
 385                 390
```

( 2 ) INFORMATION FOR SEQ ID NO:7:

( i ) SEQUENCE CHARACTERISTICS:
        ( A ) LENGTH: 1203 base pairs
        ( B ) TYPE: nucleic acid
        ( C ) STRANDEDNESS: single
        ( D ) TOPOLOGY: linear ( i i ) MOLECULE TYPE: cDNA (ix) FEATURE:
  (A) NAME/KEY: CDS
  (B) LOCATION: 1..1203

(xi) SEQUENCE DESCRIPTION: SEQ ID NO:7:

```
ATG GCA AAG TGT ACC ACC GAA AAG TTT TGT TGT ATC AGC GTG AAT AGA      48
Met Ala Lys Cys Thr Thr Glu Lys Phe Cys Cys Ile Ser Val Asn Arg
 1               5                  10                  15

GAA TCT TCT GTC GAT CCA GAA GAC TTC TAT AAA CCG GTT CCT CTA ACT      96
Glu Ser Ser Val Asp Pro Glu Asp Phe Tyr Lys Pro Val Pro Leu Thr
                20                  25                  30

TCA GAT TTG ATT GAA GAG GAT AAC CTA CAT CAA GAC AAA ATA ATG GAT     144
Ser Asp Leu Ile Glu Glu Asp Asn Leu His Gln Asp Lys Ile Met Asp
             35                  40                  45

GAG GAT TTA TAC TCG GAT TTT AGT GAT GAT GAC TTT ATG GAT TAT ACA     192
Glu Asp Leu Tyr Ser Asp Phe Ser Asp Asp Asp Phe Met Asp Tyr Thr
         50                  55                  60

AAA AAT CCA ACT GAA AGT GAA AAT GAA AGA GAA AGT GAC GAA GAA GTT     240
Lys Asn Pro Thr Glu Ser Glu Asn Glu Arg Glu Ser Asp Glu Glu Val
 65                  70                  75                  80

GAA GAA AGT TAT GAA AGT GAT GAA GAT AAA AAA AGT TTA TCT CCT ACT     288
Glu Glu Ser Tyr Glu Ser Asp Glu Asp Lys Lys Ser Leu Ser Pro Thr
                 85                  90                  95

AAA AGC GAA GGA ATT GAA GCG GCT GAA GCG CTA AAG TTT TCT GTT GTT     336
Lys Ser Glu Gly Ile Glu Ala Ala Glu Ala Leu Lys Phe Ser Val Val
                100                 105                 110

AAA TCG TTA ACG CCT GGG TCA GAA GGA AGA GTT TTT ATT GCT CTT AAA     384
Lys Ser Leu Thr Pro Gly Ser Glu Gly Arg Val Phe Ile Ala Leu Lys
             115                 120                 125

AAA GAT AAA GAT ACA AGC TAT AAG GTA ATT TTA AAA ATT GGA CAA AGG     432
Lys Asp Lys Asp Thr Ser Tyr Lys Val Ile Leu Lys Ile Gly Gln Arg
         130                 135                 140

GGA AAC ACG CTT GTG GAA TCG TTA ATT TTG AGA AAT ATT AGT CAC CAA     480
Gly Asn Thr Leu Val Glu Ser Leu Ile Leu Arg Asn Ile Ser His Gln
145                 150                 155                 160

TCT ATA ATT AAA CTT CAA GAC ACT CTT TTT TAT AAA GAG TTA ACA TGT     528
Ser Ile Ile Lys Leu Gln Asp Thr Leu Phe Tyr Lys Glu Leu Thr Cys
                165                 170                 175

TTG GTG TTA CCG TAT TAT AAA TAT GAT CTA TAT AAT TTT TTA ATG GAT     576
Leu Val Leu Pro Tyr Tyr Lys Tyr Asp Leu Tyr Asn Phe Leu Met Asp
                180                 185                 190

CAT GGG AAA TCT CTG TCT TTT GAA TCT GTA ATT AAA ATT GAA AAA CAA     624
His Gly Lys Ser Leu Ser Phe Glu Ser Val Ile Lys Ile Glu Lys Gln
             195                 200                 205

ATA TTA ACT GGA CTT CAA TAT ATT CAT GGA AAA AAA ATT ATT CAT CGA     672
Ile Leu Thr Gly Leu Gln Tyr Ile His Gly Lys Lys Ile Ile His Arg
         210                 215                 220

GAT ATA AAA ACT GAA AAT ATT TTC TTG GAT AAT GAC TCT AAT GTT TGT     720
Asp Ile Lys Thr Glu Asn Ile Phe Leu Asp Asn Asp Ser Asn Val Cys
225                 230                 235                 240

ATA GGT GAT TTT GGG GCT TCT CAA TTT CCT GTT TCC TCA CCA GAT TAT     768
Ile Gly Asp Phe Gly Ala Ser Gln Phe Pro Val Ser Ser Pro Asp Tyr
                245                 250                 255

TTG GGA ATT GCG GGG ACT ATT GAA ACT AAT GCT CCT GAA GTT CTA TCA     816
Leu Gly Ile Ala Gly Thr Ile Glu Thr Asn Ala Pro Glu Val Leu Ser
                260                 265                 270

AAG GAT GCG TAC AAC TGT AAA GCT GAT ATT TGG AGT GCT GGT ATA ATT     864
Lys Asp Ala Tyr Asn Cys Lys Ala Asp Ile Trp Ser Ala Gly Ile Ile
             275                 280                 285

TTA TTT GAA ATG CTT GCA TAT CCT AAT GTT TTG TTT GAG GAG GAA GAA     912
Leu Phe Glu Met Leu Ala Tyr Pro Asn Val Leu Phe Glu Glu Glu Glu
```

```
                290                              295                             300
AGA   GAT   AGT   AGC   GAT   TTA   ATA   AAC   AAT   TGT   AAT   CTT   CAT   CTT   ATA   AAA        960
Arg   Asp   Ser   Ser   Asp   Leu   Ile   Asn   Asn   Cys   Asn   Leu   His   Leu   Ile   Lys
305                           310                     315                           320

ATT   ATA   TCA   ACT   CTG   AAG   ATT   AAC   CCA   AAT   GAA   TTT   CCA   TCT   GAT   TTG       1008
Ile   Ile   Ser   Thr   Leu   Lys   Ile   Asn   Pro   Asn   Glu   Phe   Pro   Ser   Asp   Leu
                        325                           330                           335

GAA   TCT   AAT   CTA   GTA   AAA   CAT   TTT   ATA   AAA   TAT   GCT   AAT   AAT   GAT   AGA       1056
Glu   Ser   Asn   Leu   Val   Lys   His   Phe   Ile   Lys   Tyr   Ala   Asn   Asn   Asp   Arg
                        340                           345                           350

CCT   CCA   TTT   ACA   CGA   TAT   AAT   CGT   CTA   AAT   AAC   CTT   AAA   TTA   CAT   CTC       1104
Pro   Pro   Phe   Thr   Arg   Tyr   Asn   Arg   Leu   Asn   Asn   Leu   Lys   Leu   His   Leu
            355                           360                           365

GAT   GGT   GAA   TTT   TTA   ATT   CAT   AAA   ATG   CTA   ACA   TTT   GAT   GCA   TCT   CTA       1152
Asp   Gly   Glu   Phe   Leu   Ile   His   Lys   Met   Leu   Thr   Phe   Asp   Ala   Ser   Leu
      370                           375                           380

CGA   CCA   AGT   GCG   GAA   GAA   CTA   TTA   TCC   TAT   CAG   ATT   TTT   AGT   AAA   CAA       1200
Arg   Pro   Ser   Ala   Glu   Glu   Leu   Leu   Ser   Tyr   Gln   Ile   Phe   Ser   Lys   Gln
385                     390                           395                           400

TAA                                                                                                 1203
*
```

( 2 ) INFORMATION FOR SEQ ID NO:8:

( i ) SEQUENCE CHARACTERISTICS:
    ( A ) LENGTH: 400 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

```
Met   Ala   Lys   Cys   Thr   Thr   Glu   Lys   Phe   Cys   Cys   Ile   Ser   Val   Asn   Arg
1                       5                       10                            15

Glu   Ser   Ser   Val   Asp   Pro   Glu   Asp   Phe   Tyr   Lys   Pro   Val   Pro   Leu   Thr
                  20                            25                      30

Ser   Asp   Leu   Ile   Glu   Glu   Asp   Asn   Leu   His   Gln   Asp   Lys   Ile   Met   Asp
            35                            40                            45

Glu   Asp   Leu   Tyr   Ser   Asp   Phe   Ser   Asp   Asp   Phe   Met   Asp   Tyr   Thr
      50                            55                            60

Lys   Asn   Pro   Thr   Glu   Ser   Glu   Asn   Glu   Arg   Glu   Ser   Asp   Glu   Glu   Val
65                      70                            75                            80

Glu   Glu   Ser   Tyr   Glu   Ser   Asp   Glu   Asp   Lys   Lys   Ser   Leu   Ser   Pro   Thr
                  85                            90                            95

Lys   Ser   Glu   Gly   Ile   Glu   Ala   Ala   Glu   Ala   Leu   Lys   Phe   Ser   Val   Val
                  100                           105                     110

Lys   Ser   Leu   Thr   Pro   Gly   Ser   Glu   Gly   Arg   Val   Phe   Ile   Ala   Leu   Lys
            115                           120                     125

Lys   Asp   Lys   Asp   Thr   Ser   Tyr   Lys   Val   Ile   Leu   Lys   Ile   Gly   Gln   Arg
      130                           135                     140

Gly   Asn   Thr   Leu   Val   Glu   Ser   Leu   Ile   Leu   Arg   Asn   Ile   Ser   His   Gln
145                           150                           155                     160

Ser   Ile   Ile   Lys   Leu   Gln   Asp   Thr   Leu   Phe   Tyr   Lys   Glu   Leu   Thr   Cys
                  165                           170                           175

Leu   Val   Leu   Pro   Tyr   Tyr   Lys   Tyr   Asp   Leu   Tyr   Asn   Phe   Leu   Met   Asp
                  180                           185                           190

His   Gly   Lys   Ser   Leu   Ser   Phe   Glu   Ser   Val   Ile   Lys   Ile   Glu   Lys   Gln
            195                           200                           205
```

| | | | | | | | | | | | | | | | |
|---|---|---|---|---|---|---|---|---|---|---|---|---|---|---|---|
| Ile | Leu | Thr | Gly | Leu | Gln | Tyr | Ile | His | Gly | Lys | Lys | Ile | Ile | His | Arg |
| | 210 | | | | 215 | | | | 220 | | | | | | |
| Asp | Ile | Lys | Thr | Glu | Asn | Ile | Phe | Leu | Asp | Asn | Asp | Ser | Asn | Val | Cys |
| 225 | | | | | 230 | | | | 235 | | | | | | 240 |
| Ile | Gly | Asp | Phe | Gly | Ala | Ser | Gln | Phe | Pro | Val | Ser | Ser | Pro | Asp | Tyr |
| | | | | 245 | | | | | 250 | | | | | 255 | |
| Leu | Gly | Ile | Ala | Gly | Thr | Ile | Glu | Thr | Asn | Ala | Pro | Glu | Val | Leu | Ser |
| | | | | 260 | | | | | 265 | | | | | 270 | |
| Lys | Asp | Ala | Tyr | Asn | Cys | Lys | Ala | Asp | Ile | Trp | Ser | Ala | Gly | Ile | Ile |
| | | 275 | | | | | 280 | | | | | 285 | | | |
| Leu | Phe | Glu | Met | Leu | Ala | Tyr | Pro | Asn | Val | Leu | Phe | Glu | Glu | Glu | Glu |
| | 290 | | | | | 295 | | | | | 300 | | | | |
| Arg | Asp | Ser | Ser | Asp | Leu | Ile | Asn | Asn | Cys | Asn | Leu | His | Leu | Ile | Lys |
| 305 | | | | | 310 | | | | | 315 | | | | | 320 |
| Ile | Ile | Ser | Thr | Leu | Lys | Ile | Asn | Pro | Asn | Glu | Phe | Pro | Ser | Asp | Leu |
| | | | | 325 | | | | | 330 | | | | | 335 | |
| Glu | Ser | Asn | Leu | Val | Lys | His | Phe | Ile | Lys | Tyr | Ala | Asn | Asn | Asp | Arg |
| | | | 340 | | | | | 345 | | | | | 350 | | |
| Pro | Pro | Phe | Thr | Arg | Tyr | Asn | Arg | Leu | Asn | Asn | Leu | Lys | Leu | His | Leu |
| | | | 355 | | | | | 360 | | | | | 365 | | |
| Asp | Gly | Glu | Phe | Leu | Ile | His | Lys | Met | Leu | Thr | Phe | Asp | Ala | Ser | Leu |
| | | | 370 | | | | | 375 | | | | 380 | | | |
| Arg | Pro | Ser | Ala | Glu | Glu | Leu | Leu | Ser | Tyr | Gln | Ile | Phe | Ser | Lys | Gln |
| 385 | | | | | 390 | | | | | 395 | | | | | 400 |

(2) INFORMATION FOR SEQ ID NO:9:

(i) SEQUENCE CHARACTERISTICS:
        (A) LENGTH: 1248 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1248

(xi) SEQUENCE DESCRIPTION: SEQ ID NO:9:

| | | | | | | | | | | | | | | | | |
|---|---|---|---|---|---|---|---|---|---|---|---|---|---|---|---|---|
| ATG | TTG | TAT | ACG | CTG | TTT | TTT | GTT | TTT | TAT | TTT | AAG | GTA | GTT | TTA | TCT | 48 |
| Met | Leu | Tyr | Thr | Leu | Phe | Phe | Val | Phe | Tyr | Phe | Lys | Val | Val | Leu | Ser | |
| 1 | | | | 5 | | | | | 10 | | | | | 15 | | |
| CGC | ATA | GCT | CCG | CTA | GAG | TTG | TGT | TAT | GCG | GAT | CCT | AAA | GAA | AAT | ACA | 96 |
| Arg | Ile | Ala | Pro | Leu | Glu | Leu | Cys | Tyr | Ala | Asp | Pro | Lys | Glu | Asn | Thr | |
| | | | 20 | | | | | 25 | | | | | 30 | | | |
| ACT | GAA | CCT | ACA | CAA | CTT | CCT | ACA | GGG | GAA | CAA | TCT | AAG | ACT | CTT | ATT | 144 |
| Thr | Glu | Pro | Thr | Gln | Leu | Pro | Thr | Gly | Glu | Gln | Ser | Lys | Thr | Leu | Ile | |
| | | 35 | | | | | 40 | | | | | 45 | | | | |
| CCC | GTG | GTA | ACA | AAC | GGA | TAT | GTT | GAA | TAC | TCT | AAA | GGA | TGT | GAA | CTA | 192 |
| Pro | Val | Val | Thr | Asn | Gly | Tyr | Val | Glu | Tyr | Ser | Lys | Gly | Cys | Glu | Leu | |
| | 50 | | | | | 55 | | | | | 60 | | | | | |
| CGA | TTA | CTA | GAT | ACA | TAT | GTA | AAT | GTA | TCT | TCA | CGA | CCA | GAA | AAA | AAG | 240 |
| Arg | Leu | Leu | Asp | Thr | Tyr | Val | Asn | Val | Ser | Ser | Arg | Pro | Glu | Lys | Lys | |
| 65 | | | | | 70 | | | | | 75 | | | | | 80 | |
| GTT | AAT | GCT | ACA | ATT | GGA | TGG | TCA | TTT | GAT | CTT | GGT | TGT | CAA | ATT | CCT | 288 |
| Val | Asn | Ala | Thr | Ile | Gly | Trp | Ser | Phe | Asp | Leu | Gly | Cys | Gln | Ile | Pro | |
| | | | | 85 | | | | | 90 | | | | | 95 | | |
| TTA | ATT | TAT | AGA | GAA | TAT | TAT | AAT | TGT | ACT | GGT | AAT | ATA | ATA | CCA | TCA | 336 |
| Leu | Ile | Tyr | Arg | Glu | Tyr | Tyr | Asn | Cys | Thr | Gly | Asn | Ile | Ile | Pro | Ser | |
| | | | 100 | | | | | 105 | | | | | 110 | | | |

```
CCA GAA ACT TGT GAT GGT TAT TCT TTA ACT TTG GTA AAA TCT GAA AGT        384
Pro Glu Thr Cys Asp Gly Tyr Ser Leu Thr Leu Val Lys Ser Glu Ser
    115                 120                 125

ATA TCA TCT TAT GCA CTT GTT AAT GTT AGT TTG CTT ATT CAA CCA GGA        432
Ile Ser Ser Tyr Ala Leu Val Asn Val Ser Leu Leu Ile Gln Pro Gly
    130                 135                 140

ATT TTT GAT TCT GGT AGA TAT TTA TAC TCA CTT GTT TTT GGA AAC GAT        480
Ile Phe Asp Ser Gly Arg Tyr Leu Tyr Ser Leu Val Phe Gly Asn Asp
145                 150                 155                 160

AGT TAT AAC GGA AGA ATT GAA GTT CGA GTG GAT AAT GAG ACA GAC TAT        528
Ser Tyr Asn Gly Arg Ile Glu Val Arg Val Asp Asn Glu Thr Asp Tyr
            165                 170                 175

CCA TGT TTT ATG ATG CAT GGA TTG ACT GTA AAA AAG GGT GAT AAA CTT        576
Pro Cys Phe Met Met His Gly Leu Thr Val Lys Lys Gly Asp Lys Leu
                180                 185                 190

CAT ATT CCT TAT AAA CCA TCC ACA AAT CCT AAT CAT AAA CGA TAT AGA        624
His Ile Pro Tyr Lys Pro Ser Thr Asn Pro Asn His Lys Arg Tyr Arg
        195                 200                 205

GGT TGT TTT CCA ATA TCA AAT ACT GAG CTA TGG AAT AAT ATT AGT GAT        672
Gly Cys Phe Pro Ile Ser Asn Thr Glu Leu Trp Asn Asn Ile Ser Asp
    210                 215                 220

GAA AGT GTT GGT AGA TAT TCA TAT GAT GAA GAA TAT GAA GAA TAT GAA        720
Glu Ser Val Gly Arg Tyr Ser Tyr Asp Glu Glu Tyr Glu Glu Tyr Glu
225                 230                 235                 240

GAA GAA AAC GAA GAT TTT GAA GAT CTA CAA TCA AAA GAT TGC CGC AAA        768
Glu Glu Asn Glu Asp Phe Glu Asp Leu Gln Ser Lys Asp Cys Arg Lys
            245                 250                 255

TCC AAT CTT TTT GAT ATG AAG AAG ACT TTT AAT TTG GCT GCA GGT TCT        816
Ser Asn Leu Phe Asp Met Lys Lys Thr Phe Asn Leu Ala Ala Gly Ser
                260                 265                 270

CAA AGT TTA TTG ATT GCT AGT TTG GGT AAA TCA ATT TCA GAA CAA CCG        864
Gln Ser Leu Leu Ile Ala Ser Leu Gly Lys Ser Ile Ser Glu Gln Pro
        275                 280                 285

TGG TCA TTT AAA ATT AAT GAA AGT TAT GAA CTT TTT AAT AAT TTG TCT        912
Trp Ser Phe Lys Ile Asn Glu Ser Tyr Glu Leu Phe Asn Asn Leu Ser
    290                 295                 300

ATC ACC CTT CAA TCG GAA GAA GAT TCT AAT ATA CTG AAT CCT GAA ATT        960
Ile Thr Leu Gln Ser Glu Glu Asp Ser Asn Ile Leu Asn Pro Glu Ile
305                 310                 315                 320

GTA ACG TTT ACC ACA CCA CCA CCT ACT GAA AAT ACA CAT ATG TTT ATG       1008
Val Thr Phe Thr Thr Pro Pro Pro Thr Glu Asn Thr His Met Phe Met
            325                 330                 335

TCA AAT AAT GAA ACT ATG TAT GAA GAA GAA AGT GTT TTA AGC ATT ATT       1056
Ser Asn Asn Glu Thr Met Tyr Glu Glu Glu Ser Val Leu Ser Ile Ile
                340                 345                 350

CAA TTG TTT AAC AAT GGT TAT AAT AAT TGT AAT ACC CAT ATA AAG GTA       1104
Gln Leu Phe Asn Asn Gly Tyr Asn Asn Cys Asn Thr His Ile Lys Val
        355                 360                 365

ATT GGA TTT GGA ACA ATT ATC TTT ATT ATT TTA TTT TTT GTT GCT GTG       1152
Ile Gly Phe Gly Thr Ile Ile Phe Ile Ile Leu Phe Phe Val Ala Val
    370                 375                 380

TTT TTT TGT GGA TAT ACT TGT GTA TTA AAC TCT CGT ATT AAA ATG ATT       1200
Phe Phe Cys Gly Tyr Thr Cys Val Leu Asn Ser Arg Ile Lys Met Ile
385                 390                 395                 400

AAC CAT GCT TAT ATA CAA CCC CAG AAA TTA AAT TTT TAT GAT ATT TAA       1248
Asn His Ala Tyr Ile Gln Pro Gln Lys Leu Asn Phe Tyr Asp Ile *
            405                 410                 415
```

( 2 ) INFORMATION FOR SEQ ID NO:10:

( i ) SEQUENCE CHARACTERISTICS:
  ( A ) LENGTH: 415 amino acids
  ( B ) TYPE: amino acid
  ( D ) TOPOLOGY: linear ( i i ) MOLECULE TYPE: protein ( x i ) SEQUENCE DESCRIPTION: SEQ ID NO:10:

| Met<br>1 | Leu | Tyr | Thr | Leu<br>5 | Phe | Phe | Val | Phe | Tyr<br>10 | Phe | Lys | Val | Val | Leu<br>15 | Ser |
|---|---|---|---|---|---|---|---|---|---|---|---|---|---|---|---|
| Arg | Ile | Ala | Pro<br>20 | Leu | Glu | Leu | Cys | Tyr<br>25 | Ala | Asp | Pro | Lys | Glu<br>30 | Asn | Thr |
| Thr | Glu | Pro<br>35 | Thr | Gln | Leu | Pro | Thr<br>40 | Gly | Glu | Gln | Ser | Lys<br>45 | Thr | Leu | Ile |
| Pro | Val<br>50 | Val | Thr | Asn | Gly | Tyr<br>55 | Val | Glu | Tyr | Ser | Lys<br>60 | Gly | Cys | Glu | Leu |
| Arg<br>65 | Leu | Leu | Asp | Thr | Tyr<br>70 | Val | Asn | Val | Ser | Ser<br>75 | Arg | Pro | Glu | Lys | Lys<br>80 |
| Val | Asn | Ala | Thr | Ile<br>85 | Gly | Trp | Ser | Phe | Asp<br>90 | Leu | Gly | Cys | Gln | Ile<br>95 | Pro |
| Leu | Ile | Tyr | Arg<br>100 | Glu | Tyr | Tyr | Asn | Cys<br>105 | Thr | Gly | Asn | Ile | Ile<br>110 | Pro | Ser |
| Pro | Glu | Thr<br>115 | Cys | Asp | Gly | Tyr | Ser<br>120 | Leu | Thr | Leu | Val | Lys<br>125 | Ser | Glu | Ser |
| Ile | Ser<br>130 | Ser | Tyr | Ala | Leu | Val<br>135 | Asn | Val | Ser | Leu | Leu<br>140 | Ile | Gln | Pro | Gly |
| Ile<br>145 | Phe | Asp | Ser | Gly | Arg<br>150 | Tyr | Leu | Tyr | Ser | Leu<br>155 | Val | Phe | Gly | Asn | Asp<br>160 |
| Ser | Tyr | Asn | Gly | Arg<br>165 | Ile | Glu | Val | Arg | Val<br>170 | Asp | Asn | Glu | Thr | Asp<br>175 | Tyr |
| Pro | Cys | Phe | Met<br>180 | Met | His | Gly | Leu | Thr<br>185 | Val | Lys | Lys | Gly | Asp<br>190 | Lys | Leu |
| His | Ile | Pro<br>195 | Tyr | Lys | Pro | Ser | Thr<br>200 | Asn | Pro | Asn | His | Lys<br>205 | Arg | Tyr | Arg |
| Gly | Cys<br>210 | Phe | Pro | Ile | Ser | Asn<br>215 | Thr | Glu | Leu | Trp | Asn<br>220 | Asn | Ile | Ser | Asp |
| Glu<br>225 | Ser | Val | Gly | Arg | Tyr<br>230 | Ser | Tyr | Asp | Glu | Glu<br>235 | Tyr | Glu | Glu | Tyr | Glu<br>240 |
| Glu | Glu | Asn | Glu | Asp<br>245 | Phe | Glu | Asp | Leu | Gln<br>250 | Ser | Lys | Asp | Cys | Arg<br>255 | Lys |
| Ser | Asn | Leu | Phe<br>260 | Asp | Met | Lys | Lys | Thr<br>265 | Phe | Asn | Leu | Ala | Ala<br>270 | Gly | Ser |
| Gln | Ser | Leu<br>275 | Leu | Ile | Ala | Ser | Leu<br>280 | Gly | Lys | Ser | Ile | Ser<br>285 | Glu | Gln | Pro |
| Trp | Ser<br>290 | Phe | Lys | Ile | Asn | Glu<br>295 | Ser | Tyr | Glu | Leu | Phe<br>300 | Asn | Asn | Leu | Ser |
| Ile<br>305 | Thr | Leu | Gln | Ser | Glu<br>310 | Glu | Asp | Ser | Asn | Ile<br>315 | Leu | Asn | Pro | Glu | Ile<br>320 |
| Val | Thr | Phe | Thr | Thr<br>325 | Pro | Pro | Pro | Thr | Glu<br>330 | Asn | Thr | His | Met | Phe<br>335 | Met |
| Ser | Asn | Asn | Glu<br>340 | Thr | Met | Tyr | Glu | Glu<br>345 | Glu | Ser | Val | Leu | Ser<br>350 | Ile | Ile |
| Gln | Leu | Phe<br>355 | Asn | Asn | Gly | Tyr | Asn<br>360 | Asn | Cys | Asn | Thr | His<br>365 | Ile | Lys | Val |
| Ile | Gly<br>370 | Phe | Gly | Thr | Ile | Ile<br>375 | Phe | Ile | Ile | Leu | Phe<br>380 | Phe | Val | Ala | Val |

5,753,235

| Phe | Phe | Cys | Gly | Tyr | Thr | Cys | Val | Leu | Asn | Ser | Arg | Ile | Lys | Met | Ile |
| 385 | | | | 390 | | | | | 395 | | | | | | 400 |

| Asn | His | Ala | Tyr | Ile | Gln | Pro | Gln | Lys | Leu | Asn | Phe | Tyr | Asp | Ile |
| | | | | 405 | | | | | 410 | | | | | 415 |

( 2 ) INFORMATION FOR SEQ ID NO:11:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..357

( x i ) SEQUENCE DESCRIPTION: SEQ ID NO:11:

```
ATG ATT AAA CTT CTA TTT ATC TTA TTT TAT TTT AAC CCA ATA ACT GGA      48
Met Ile Lys Leu Leu Phe Ile Leu Phe Tyr Phe Asn Pro Ile Thr Gly
 1               5                   10                  15

TAT AAA TGG GTA GAC CCT CCT CGT AGG TAT AAT TAC ACC GTT TTA AGA      96
Tyr Lys Trp Val Asp Pro Pro Arg Arg Tyr Asn Tyr Thr Val Leu Arg
            20                  25                  30

ATG ATT CCA GAT ATT CCA AAT CCA ATG GAT CCT TCT AAA AAC GCT GAA     144
Met Ile Pro Asp Ile Pro Asn Pro Met Asp Pro Ser Lys Asn Ala Glu
         35                  40                  45

GTT CGG TAT GTA ACT TCT ACT GAC CCA TGT GAT ATG GTT GCT TTG ATT     192
Val Arg Tyr Val Thr Ser Thr Asp Pro Cys Asp Met Val Ala Leu Ile
     50                  55                  60

TCT AAT CCA AAT ATA GAA TCT ACA ATT AAA ACG ATT CAA TTT GTG CAA     240
Ser Asn Pro Asn Ile Glu Ser Thr Ile Lys Thr Ile Gln Phe Val Gln
 65                  70                  75                  80

AAG AAA AAA TTT TAC AAT GCA TCT CTT AGT TGG TTT AAA GTT GGA GAT     288
Lys Lys Lys Phe Tyr Asn Ala Ser Leu Ser Trp Phe Lys Val Gly Asp
             85                  90                  95

GAT TGT ACA TAT CCA ATA TAT TTA ATT CAA TAT TTT GAT TGT GAT CCT     336
Asp Cys Thr Tyr Pro Ile Tyr Leu Ile Gln Tyr Phe Asp Cys Asp Pro
             100                 105                 110

CAA AGA GAA TTT GGC ATA TGT                                          357
Gln Arg Glu Phe Gly Ile Cys
             115
```

( 2 ) INFORMATION FOR SEQ ID NO:12:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Met | Ile | Lys | Leu | Leu | Phe | Ile | Leu | Phe | Tyr | Phe | Asn | Pro | Ile | Thr | Gly |
| 1 | | | | 5 | | | | | 10 | | | | | 15 | |

| Tyr | Lys | Trp | Val | Asp | Pro | Pro | Arg | Arg | Tyr | Asn | Tyr | Thr | Val | Leu | Arg |
| | | | 20 | | | | | 25 | | | | | 30 | | |

| Met | Ile | Pro | Asp | Ile | Pro | Asn | Pro | Met | Asp | Pro | Ser | Lys | Asn | Ala | Glu |
| | | 35 | | | | | 40 | | | | | 45 | | | |

| Val | Arg | Tyr | Val | Thr | Ser | Thr | Asp | Pro | Cys | Asp | Met | Val | Ala | Leu | Ile |
| | 50 | | | | | 55 | | | | | 60 | | | | |

```
Ser Asn Pro Asn Ile Glu Ser Thr Ile Lys Thr Ile Gln Phe Val Gln
 65                 70                  75                  80

Lys Lys Lys Phe Tyr Asn Ala Ser Leu Ser Trp Phe Lys Val Gly Asp
                 85                  90                  95

Asp Cys Thr Tyr Pro Ile Tyr Leu Ile Gln Tyr Phe Asp Cys Asp Pro
                100                 105                 110

Gln Arg Glu Phe Gly Ile Cys
            115
```

( 2 ) INFORMATION FOR SEQ ID NO:13:

( i ) SEQUENCE CHARACTERISTICS:
        ( A ) LENGTH: 743 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CGAAGCGGGA  GGAGGATGCT  GGTTATGATA  TACCATCTCC  AAATTTAGTT  CAAATAAAAC    60
CGGGATATAG  TTACCTTTTT  TGTCTTCCTA  TTTTTCAATT  AGAAATGAAA  AACCCACCAA   120
TCGCTTGTAT  TTTTGGTAGA  TCATCCTTAA  ATTCAAGCGG  AATAATTGTT  CTTCCAACTA   180
TATGGAAACC  AAAAACAATT  TGTCAATTTT  TTATTAAAAA  TATATCCTCT  AAAACTGTAA   240
CTATAGAAAA  AGGTCAGAGA  ATAGCTCAGT  TAGTTCTTTT  AAAAACAAT   CAACCACTAT   300
GGTTACAACC  ACAAATTAAT  TGTCATTCTT  TATTTCCAAA  GTCAAACTAT  TTAAGCTTAT   360
CAAATCGAGA  ATGTGATATG  TGGAAGTTTA  CAGAAGATCT  GAATTTTGAA  GCACCGAAAA   420
GTTACGAGG   AATAAATGGA  TTTGGATCCA  CGGGATTGTA  AAATTCGTTA  ATAAAGTTAT   480
ATTTAAAGTG  CCAAACTTTC  ACGTGTCATT  TTTTGGGAC   CGTTCTTTT   TTGTTTAGTC   540
GATAAAATAT  TTTCAGTTTC  CATAGAACTT  ATTAGAGGTT  CTGTATCTAG  TATATCTGTA   600
GAATTATTTT  CATCATATTT  AACGGTTTGA  AGAGATAAGG  GTTTTGTTGT  ATTAGAATCT   660
ATACCAAGGG  TTTTTTCTAA  AACCGCTACA  TCTGCCATAA  CAATATTATT  TTCTGAAGTC   720
ATTTTTATGG  CTTGGGCACC  ACC                                              743
```

( 2 ) INFORMATION FOR SEQ ID NO:14:

( i ) SEQUENCE CHARACTERISTICS:
        ( A ) LENGTH: 743 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
GGTGGTGCCC  AAGCCATAAA  AATGACTTCA  GAAAATAATA  TTGTTATGGC  AGATGTAGCG    60
GTTTTAGAAA  AAACCCTTGG  TATAGATTCT  AATACAACAA  AACCCTTATC  TCTTCAAACC   120
GTTAAATATG  ATGAAAATAA  TTCTACAGAT  ATACTAGATA  CAGAACCTCT  AATAAGTTCT   180
ATGGAAACTG  AAAATATTTT  ATCGACTAAA  CAAAAAAGAA  ACGGTCCCAA  AAAAATGACA   240
CGTGAAAGTT  TGGCACTTTA  AATATAACTT  TATTAACGAA  TTTTACAATC  CCGTGGATCC   300
AAATCCATTT  ATTCCTCGTA  AACTTTTCGG  TGCTTCAAAA  TTCAGATCTT  CTGTAAACTT   360
CCACATATCA  CATTCTCGAT  TTGATAAGCT  TAAATAGTTT  GACTTTGGAA  ATAAAGAATG   420
ACAATTAATT  TGTGGTTGTA  ACCATAGTGG  TTGATTGTTT  TTAAAAGAA   CTAACTGAGC   480
```

-continued

```
TATTCTCTGA CCTTTTTCTA TAGTTACAGT TTTAGAGGAT ATATTTTTAA TAAAAAATTG    540

ACAAATTGTT TTTGGTTTCC ATATAGTTGG AAGAACAATT ATTCCGCTTG AATTTAAGGA    600

TGATCTACCA AAAATACAAG CGATTGGTGG GTTTTTCATT TCTAATTGAA AAATAGGAAG    660

ACAAAAAAGG TAACTATATC CCGGTTTTAT TTGAACTAAA TTTGGAGATG GTATATCATA    720

ACCAGCATCC TCCTCCCGCT TCG    743
```

( 2 ) INFORMATION FOR SEQ ID NO:15:

( i ) SEQUENCE CHARACTERISTICS:
        ( A ) LENGTH: 459 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..459

( x i ) SEQUENCE DESCRIPTION: SEQ ID NO:15:

```
AAG CGG GAG GAG GAT GCT GGT TAT GAT ATA CCA TCT CCA AAT TTA GTT     48
Lys Arg Glu Glu Asp Ala Gly Tyr Asp Ile Pro Ser Pro Asn Leu Val
 1               5                  10                  15

CAA ATA AAA CCG GGA TAT AGT TAC CTT TTT TGT CTT CCT ATT TTT CAA     96
Gln Ile Lys Pro Gly Tyr Ser Tyr Leu Phe Cys Leu Pro Ile Phe Gln
                20                  25                  30

TTA GAA ATG AAA AAC CCA CCA ATC GCT TGT ATT TTT GGT AGA TCA TCC    144
Leu Glu Met Lys Asn Pro Pro Ile Ala Cys Ile Phe Gly Arg Ser Ser
            35                  40                  45

TTA AAT TCA AGC GGA ATA ATT GTT CTT CCA ACT ATA TGG AAA CCA AAA    192
Leu Asn Ser Ser Gly Ile Ile Val Leu Pro Thr Ile Trp Lys Pro Lys
        50                  55                  60

ACA ATT TGT CAA TTT TTT ATT AAA AAT ATA TCC TCT AAA ACT GTA ACT    240
Thr Ile Cys Gln Phe Phe Ile Lys Asn Ile Ser Ser Lys Thr Val Thr
 65                 70                  75                  80

ATA GAA AAA GGT CAG AGA ATA GCT CAG TTA GTT CTT TTA AAA AAC AAT    288
Ile Glu Lys Gly Gln Arg Ile Ala Gln Leu Val Leu Leu Lys Asn Asn
                85                  90                  95

CAA CCA CTA TGG TTA CAA CCA CAA ATT AAT TGT CAT TCT TTA TTT CCA    336
Gln Pro Leu Trp Leu Gln Pro Gln Ile Asn Cys His Ser Leu Phe Pro
            100                 105                 110

AAG TCA AAC TAT TTA AGC TTA TCA AAT CGA GAA TGT GAT ATG TGG AAG    384
Lys Ser Asn Tyr Leu Ser Leu Ser Asn Arg Glu Cys Asp Met Trp Lys
        115                 120                 125

TTT ACA GAA GAT CTG AAT TTT GAA GCA CCG AAA AGT TTA CGA GGA ATA    432
Phe Thr Glu Asp Leu Asn Phe Glu Ala Pro Lys Ser Leu Arg Gly Ile
130                 135                 140

AAT GGA TTT GGA TCC ACG GGA TTG TAA                                459
Asn Gly Phe Gly Ser Thr Gly Leu *
145                 150
```

( 2 ) INFORMATION FOR SEQ ID NO:16:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Lys Arg Glu Glu Asp Ala Gly Tyr Asp Ile Pro Ser Pro Asn Leu Val
```

|   | 1 |   |   |   | 5 |   |   |   |   | 10 |   |   |   |   | 15 |
|---|---|---|---|---|---|---|---|---|---|---|---|---|---|---|---|

Gln Ile Lys Pro Gly Tyr Ser Tyr Leu Phe Cys Leu Pro Ile Phe Gln
        20                  25                  30

Leu Glu Met Lys Asn Pro Pro Ile Ala Cys Ile Phe Gly Arg Ser Ser
          35                  40                  45

Leu Asn Ser Ser Gly Ile Ile Val Leu Pro Thr Ile Trp Lys Pro Lys
        50                  55                  60

Thr Ile Cys Gln Phe Phe Ile Lys Asn Ile Ser Ser Lys Thr Val Thr
65                  70                  75                  80

Ile Glu Lys Gly Gln Arg Ile Ala Gln Leu Val Leu Leu Lys Asn Asn
              85                  90                  95

Gln Pro Leu Trp Leu Gln Pro Gln Ile Asn Cys His Ser Leu Phe Pro
            100                 105                 110

Lys Ser Asn Tyr Leu Ser Leu Ser Asn Arg Glu Cys Asp Met Trp Lys
          115                 120                 125

Phe Thr Glu Asp Leu Asn Phe Glu Ala Pro Lys Ser Leu Arg Gly Ile
        130                 135                 140

Asn Gly Phe Gly Ser Thr Gly Leu
145             150

(2) INFORMATION FOR SEQ ID NO:17:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 54..503

(xi) SEQUENCE DESCRIPTION: SEQ ID NO:17:

```
AATTATTACT CTAAATCTCA CTTCATTATA CTTATATAAT AATATAAAAC CTT ATG                56
                                                          Met
                                                            1

TTT GTC ATT ATT AAC TTA ACA CTA GAT GGT ACT ATA AAG CTA ACT TAC              104
Phe Val Ile Ile Asn Leu Thr Leu Asp Gly Thr Ile Lys Leu Thr Tyr
          5                   10                  15

AAT ATA AAT AGT AAG ATT AGT TTA TAT AAA TTA CAT TTA ATG GCT TTA              152
Asn Ile Asn Ser Lys Ile Ser Leu Tyr Lys Leu His Leu Met Ala Leu
            20                  25                  30

CCA GAT AAC GTT TTT AGT ATT ATT AAT GAA AAT TAT ATC GAT GGA ATT              200
Pro Asp Asn Val Phe Ser Ile Ile Asn Glu Asn Tyr Ile Asp Gly Ile
        35                  40                  45

TTA ACT ATG AAA ATG GGT GAA GAA ATA GAA AGC TCA TCA CCA TTA AAT              248
Leu Thr Met Lys Met Gly Glu Glu Ile Glu Ser Ser Ser Pro Leu Asn
50                  55                  60                  65

GAA ACA AAT GTT AAT ATA GAT CAA CAT ACA ATA GAT ATT TTT GAT TAC              296
Glu Thr Asn Val Asn Ile Asp Gln His Thr Ile Asp Ile Phe Asp Tyr
              70                  75                  80

GAT TCA GAT AAT GGA TGT TAT TAT AGT GAA AGA GAT AAT GAA ACC GCA              344
Asp Ser Asp Asn Gly Cys Tyr Tyr Ser Glu Arg Asp Asn Glu Thr Ala
            85                  90                  95

ACT CTT TTT TTA AAA CGT GTT GGT TAT AGA GAA ACC TCA AAA AAG CGT              392
Thr Leu Phe Leu Lys Arg Val Gly Tyr Arg Glu Thr Ser Lys Lys Arg
        100                 105                 110

AAA CGG ATT TGT GGA TTT ATT GTT TTA GCA ATT TTT ATG GTT ATT ATA              440
Lys Arg Ile Cys Gly Phe Ile Val Leu Ala Ile Phe Met Val Ile Ile
```

```
                    115                    120                         125
TTA  TGT  TTT  TTA  TCA  ATA  ATT  TTG  GGA  GTT  TTT  ATA  GCG  CCT  CAT  ATT    488
Leu  Cys  Phe  Leu  Ser  Ile  Ile  Leu  Gly  Val  Phe  Ile  Ala  Pro  His  Ile
130                      135                      140                      145

TAT  AAA  GGC  CTA  TAG  TAAGAACATC  AACCTCTAAT  AGGTAAATTT  TTAAAACCAA           543
Tyr  Lys  Gly  Leu  *
                    150

CGGAGGGGGA  GGAGGAGGAC  TTTTTATTTT  ATGAGA                                        579
```

( 2 ) INFORMATION FOR SEQ ID NO:18:

( i ) SEQUENCE CHARACTERISTICS:
        ( A ) LENGTH: 149 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Phe  Val  Ile  Ile  Asn  Leu  Thr  Leu  Asp  Gly  Thr  Ile  Lys  Leu  Thr
  1                  5                        10                       15

Tyr  Asn  Ile  Asn  Ser  Lys  Ile  Ser  Leu  Tyr  Lys  Leu  His  Leu  Met  Ala
               20                       25                       30

Leu  Pro  Asp  Asn  Val  Phe  Ser  Ile  Ile  Asn  Glu  Asn  Tyr  Ile  Asp  Gly
              35                       40                       45

Ile  Leu  Thr  Met  Lys  Met  Gly  Glu  Glu  Ile  Glu  Ser  Ser  Pro  Leu
         50                       55                       60

Asn  Glu  Thr  Asn  Val  Asn  Ile  Asp  Gln  His  Thr  Ile  Asp  Ile  Phe  Asp
 65                       70                       75                       80

Tyr  Asp  Ser  Asp  Asn  Gly  Cys  Tyr  Tyr  Ser  Glu  Arg  Asp  Asn  Glu  Thr
                   85                       90                       95

Ala  Thr  Leu  Phe  Leu  Lys  Arg  Val  Gly  Tyr  Arg  Glu  Thr  Ser  Lys  Lys
              100                      105                      110

Arg  Lys  Arg  Ile  Cys  Gly  Phe  Ile  Val  Leu  Ala  Ile  Phe  Met  Val  Ile
             115                      120                      125

Ile  Leu  Cys  Phe  Leu  Ser  Ile  Ile  Leu  Gly  Val  Phe  Ile  Ala  Pro  His
         130                      135                      140

Ile  Tyr  Lys  Gly  Leu
145                      150
```

( 2 ) INFORMATION FOR SEQ ID NO:19:

( i ) SEQUENCE CHARACTERISTICS:
        ( A ) LENGTH: 579 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

```
TCTCATAAAA  TAAAAAGTCC  TCCTCCTCCC  CCTCCGTTGG  TTTTAAAAAT  TTACCTATTA     60
GAGGTTGATG  TTCTTACTAT  AGGCCTTTAT  AAATATGAGG  CGCTATAAAA  ACTCCCAAAA    120
TTATTGATAA  AAAACATAAT  ATAATAACCA  TAAAAATTGC  TAAAACAATA  AATCCACAAA    180
TCCGTTTACG  CTTTTTTGAG  GTTTCTCTAT  AACCAACACG  TTTAAAAAA   AGAGTTGCGG    240
TTTCATTATC  TCTTTCACTA  TAATAACATC  CATTATCTGA  ATCGTAATCA  AAAATATCTA    300
TTGTATGTTG  ATCTATATTA  ACATTTGTTT  CATTTAATGG  TGATGAGCTT  TCTATTTCTT    360
CACCCATTTT  CATAGTTAAA  ATTCCATCGA  TATAATTTTC  ATTAATAATA  CTAAAAACGT    420
```

```
TATCTGGTAA AGCCATTAAA TGTAATTTAT ATAAACTAAT CTTACTATTT ATATTGTAAG      480

TTAGCTTTAT AGTACCATCT AGTGTTAAGT TAATAATGAC AAACATAAGG TTTTATATTA      540

TTATATAAGT ATAATGAAGT GAGATTTAGA GTAATAATT                             579
```

( 2 ) INFORMATION FOR SEQ ID NO:20:

( i ) SEQUENCE CHARACTERISTICS:
        ( A ) LENGTH: 450 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

```
ATGTTTGTCA TTATTAACTT AACACTAGAT GGTACTATAA AGCTAACTTA CAATATAAAT       60

AGTAAGATTA GTTTATATAA ATTACATTTA ATGGCTTTAC CAGATAACGT TTTTAGTATT      120

ATTAATGAAA ATTATATCGA TGGAATTTTA ACTATGAAAA TGGGTGAAGA AATAGAAAGC      180

TCATCACCAT TAAATGAAAC AAATGTTAAT ATAGATCAAC ATACAATAGA TATTTTTGAT      240

TACGATTCAG ATAATGGATG TTATTATAGT GAAAGAGATA ATGAAACCGC AACTCTTTTT      300

TTAAAACGTG TTGGTTATAG AGAAACCTCA AAAAAGCGTA AACGGATTTG TGGATTTATT      360

GTTTAGCAA TTTTTATGGT TATTATATTA TGTTTTTTAT CAATAATTTT GGGAGTTTTT      420

ATAGCGCCTC ATATTTATAA AGGCCTATAG                                      450
```

( 2 ) INFORMATION FOR SEQ ID NO:21:

( i ) SEQUENCE CHARACTERISTICS:
        ( A ) LENGTH: 294 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..293

( i x ) FEATURE:
        ( A ) NAME/KEY: R =A or G
        ( B ) LOCATION: 49

( x i ) SEQUENCE DESCRIPTION: SEQ ID NO:21:

```
TC CAA AGT GTT TTT GTT TCA TTG TCT TAT TCT TGG AGC CAC CGA CGA          47
   Gln Ser Val Phe Val Ser Leu Ser Tyr Ser Trp Ser His Arg Arg
   1               5                  10                  15

CRG TTT GAG TGT ATA TTT CAT CCA ATT TTA TTT AAT CAT GGT ATT GTG         95
Xaa Phe Glu Cys Ile Phe His Pro Ile Leu Phe Asn His Gly Ile Val
                20                  25                  30

AAT TTG GAA AAT AAC CCT TTG ACA TTT AAG GAA CTA CAA AAA ATA AAT        143
Asn Leu Glu Asn Asn Pro Leu Thr Phe Lys Glu Leu Gln Lys Ile Asn
                35                  40                  45

TAT AGA CGT CAT ATT CTT GGT TTA CCA TTG ATT AGA GCT GGA TTG GTA        191
Tyr Arg Arg His Ile Leu Gly Leu Pro Leu Ile Arg Ala Gly Leu Val
                50                  55                  60

GAA GAA GAT AAT CAA CCT TTA ATG ATA CCT CCA GAG TTT TCC AGT AAA        239
Glu Glu Asp Asn Gln Pro Leu Met Ile Pro Pro Glu Phe Ser Ser Lys
        65                  70                  75

CTA CCT CGA ACA ATA GGA TTT TTA ACT CAA CAA ATT AGA GCC AAA ATG        287
Leu Pro Arg Thr Ile Gly Phe Leu Thr Gln Gln Ile Arg Ala Lys Met
80                  85                  90                  95
```

```
GAA GCT T                                                                                        294
Glu Ala
```

( 2 ) INFORMATION FOR SEQ ID NO:22:

( i ) SEQUENCE CHARACTERISTICS:
        ( A ) LENGTH: 97 amino acids
        ( B ) TYPE: amino acid
        ( D ) TOPOLOGY: linear ( i i ) MOLECULE TYPE: protein ( i x ) FEATURE:
        ( A ) NAME/KEY: Xaa =Arg or Gln
        ( B ) LOCATION: 16

( x i ) SEQUENCE DESCRIPTION: SEQ ID NO:22:

```
Gln Ser Val Phe Val Ser Leu Ser Tyr Ser Trp Ser His Arg Arg Xaa
 1           5                       10                      15

Phe Glu Cys Ile Phe His Pro Ile Leu Phe Asn His Gly Ile Val Asn
             20                  25                  30

Leu Glu Asn Asn Pro Leu Thr Phe Lys Glu Leu Gln Lys Ile Asn Tyr
         35                  40                  45

Arg Arg His Ile Leu Gly Leu Pro Leu Ile Arg Ala Gly Leu Val Glu
     50              55                  60

Glu Asp Asn Gln Pro Leu Met Ile Pro Pro Glu Phe Ser Ser Lys Leu
 65                  70                  75                  80

Pro Arg Thr Ile Gly Phe Leu Thr Gln Gln Ile Arg Ala Lys Met Glu
                 85                  90                  95

Ala
```

( 2 ) INFORMATION FOR SEQ ID NO:23:

( i ) SEQUENCE CHARACTERISTICS:
        ( A ) LENGTH: 294 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
AAGCTTCCAT TTTGGCTCTA ATTTGTTGAG TTAAAAATCC TATTGTTCGA GGTAGTTTAC     60
TGGAAAACTC TGGAGGTATC ATTAAAGGTT GATTATCTTC TTCTACCAAT CCAGCTCTAA    120
TCAATGGTAA ACCAAGAATA TGACGTCTAT AATTTATTTT TTGTAGTTCC TTAAATGTCA    180
AAGGGTTATT TTCCAAATTC ACAATACCAT GATTAAATAA AATTGGATGA AATATACACT    240
CAAAC YGTCG TCGGTGGCTC CAAGAATAAG ACAATGAAAC AAAAACACTT TGGA         294
```

( 2 ) INFORMATION FOR SEQ ID NO:24:

( i ) SEQUENCE CHARACTERISTICS:
        ( A ) LENGTH: 291 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
CAAAGTGTTT TTGTTTCATT GTCTTATTCT TGGAGCCACC GACGACRGTT TGAGTGTATA     60
TTTCATCCAA TTTTATTTAA TCATGGTATT GTGAATTTGG AAAATAACCC TTTGACATTT    120
```

AAGGAACTAC AAAAAATAAA TTATAGACGT CATATTCTTG GTTTACCATT GATTAGAGCT  180

GGATTGGTAG AAGAAGATAA TCAACCTTTA ATGATACCTC CAGAGTTTTC CAGTAAACTA  240

CCTCGAACAA TAGGATTTTT AACTCAACAA ATTAGAGCCA AAATGGAAGC T  291

( 2 ) INFORMATION FOR SEQ ID NO:25:

( i ) SEQUENCE CHARACTERISTICS:
        ( A ) LENGTH: 146 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..146

( x i ) SEQUENCE DESCRIPTION: SEQ ID NO:25:

```
CTA  GAA  GAT  TAT  ATA  ACA  CAT  CGA  ATT  AAT  GCC  GAT  ATT  TCA  GAG  GTT       48
Leu  Glu  Asp  Tyr  Ile  Thr  His  Arg  Ile  Asn  Ala  Asp  Ile  Ser  Glu  Val
  1                    5                         10                        15

GGT  GTA  TTG  AGA  AAT  TAT  ATT  TCT  GCT  GAT  AGA  CAG  AGT  TTA  AAA  GTT       96
Gly  Val  Leu  Arg  Asn  Tyr  Ile  Ser  Ala  Asp  Arg  Gln  Ser  Leu  Lys  Val
                  20                        25                        30

TCT  GAT  AGA  GAG  TTT  ATT  AAT  TAT  ATT  TAC  TTG  GCA  CAT  TTT  GAA  AGC  TT  146
Ser  Asp  Arg  Glu  Phe  Ile  Asn  Tyr  Ile  Tyr  Leu  Ala  His  Phe  Glu  Ser
              35                        40                        45
```

( 2 ) INFORMATION FOR SEQ ID NO:26:

( i ) SEQUENCE CHARACTERISTICS:
        ( A ) LENGTH: 48 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Leu  Glu  Asp  Tyr  Ile  Thr  His  Arg  Ile  Asn  Ala  Asp  Ile  Ser  Glu  Val
  1                    5                         10                        15

Gly  Val  Leu  Arg  Asn  Tyr  Ile  Ser  Ala  Asp  Arg  Gln  Ser  Leu  Lys  Val
                  20                        25                        30

Ser  Asp  Arg  Glu  Phe  Ile  Asn  Tyr  Ile  Tyr  Leu  Ala  His  Phe  Glu  Ser
              35                        40                        45
```

( 2 ) INFORMATION FOR SEQ ID NO:27:

( i ) SEQUENCE CHARACTERISTICS:
        ( A ) LENGTH: 146 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

AAGCTTTCAA AATGTGCCAA GTAAATATAA TTAATAAACT CTCTATCAGA AACTTTTAAA  60

CTCTGTCTAT CAGCAGAAAT ATAATTTCTC AATACACCAA CCTCTGAAAT ATCGGCATTA  120

ATTCGATGTG TTATATAATC TTCTAG  146

( 2 ) INFORMATION FOR SEQ ID NO:28:

( i ) SEQUENCE CHARACTERISTICS:
        ( A ) LENGTH: 144 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:28:

```
CTAGAAGATT ATATAACACA TCGAATTAAT GCCGATATTT CAGAGGTTGG TGTATTGAGA      60

AATTATATTT CTGCTGATAG ACAGAGTTTA AAAGTTTCTG ATAGAGAGTT TATTAATTAT     120

ATTTACTTGG CACATTTTGA AAGC                                            144
```

( 2 ) INFORMATION FOR SEQ ID NO:29:

( i ) SEQUENCE CHARACTERISTICS:
( A ) LENGTH: 161 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 3..161

( x i ) SEQUENCE DESCRIPTION: SEQ ID NO:29:

```
TT ATG TCA GTG GAC GTT ATA TTT CTC GAT GAC CAA CAT CTG TCA GTA        47
   Met Ser Val Asp Val Ile Phe Leu Asp Asp Gln His Leu Ser Val
   1               5                  10                  15

AAT AAT TAT AGC GGA ACT ATT GAG TTT ATT CAT TTT AAT AAC TCT TGT       95
Asn Asn Tyr Ser Gly Thr Ile Glu Phe Ile His Phe Asn Asn Ser Cys
             20                  25                  30

TAT ACC GTT TAT CAA ACT ATT GAA TAT TTT TCT TGT CCT CGC ATT TTT      143
Tyr Thr Val Tyr Gln Thr Ile Glu Tyr Phe Ser Cys Pro Arg Ile Phe
             35                  40                  45

AAT AAT GCT TTT AGA TCT                                              161
Asn Asn Ala Phe Arg Ser
            50
```

( 2 ) INFORMATION FOR SEQ ID NO:30:

( i ) SEQUENCE CHARACTERISTICS:
( A ) LENGTH: 53 amino acids
( B ) TYPE: amino acid
( D ) TOPOLOGY: linear ( i i ) MOLECULE TYPE: protein ( x i ) SEQUENCE DESCRIPTION: SEQ ID NO:30:

```
Met Ser Val Asp Val Ile Phe Leu Asp Asp Gln His Leu Ser Val Asn
1               5                  10                  15

Asn Tyr Ser Gly Thr Ile Glu Phe Ile His Phe Asn Asn Ser Cys Tyr
             20                  25                  30

Thr Val Tyr Gln Thr Ile Glu Tyr Phe Ser Cys Pro Arg Ile Phe Asn
             35                  40                  45

Asn Ala Phe Arg Ser
         50
```

( 2 ) INFORMATION FOR SEQ ID NO:31:

( i ) SEQUENCE CHARACTERISTICS:
( A ) LENGTH: 161 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:31:

| AGATCTAAAA | GCATTATTAA | AAATGCGAGG | ACAAGAAAAA | TATTCAATAG | TTTGATAAAC | 60 |
| GGTATAACAA | GAGTTATTAA | AATGAATAAA | CTCAATAGTT | CCGCTATAAT | TATTTACTGA | 120 |
| CAGATGTTGG | TCATCGAGAA | ATATAACGTC | CACTGACATA | A | | 161 |

( 2 ) INFORMATION FOR SEQ ID NO:32:

( i ) SEQUENCE CHARACTERISTICS:
    ( A ) LENGTH: 159 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:32:

| ATGTCAGTGG | ACGTTATATT | TCTCGATGAC | CAACATCTGT | CAGTAAATAA | TTATAGCGGA | 60 |
| ACTATTGAGT | TTATTCATTT | TAATAACTCT | TGTTATACCG | TTTATCAAAC | TATTGAATAT | 120 |
| TTTTCTTGTC | CTCGCATTTT | TAATAATGCT | TTTAGATCT | | | 159 |

( 2 ) INFORMATION FOR SEQ ID NO:33:

( i ) SEQUENCE CHARACTERISTICS:
    ( A ) LENGTH: 261 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 1..261

( x i ) SEQUENCE DESCRIPTION: SEQ ID NO:33:

| GGT | GGT | GCC | CAA | GCC | ATA | AAA | ATG | ACT | TCA | GAA | AAT | AAT | ATT | GTT | ATG | 48 |
| Gly | Gly | Ala | Gln | Ala | Ile | Lys | Met | Thr | Ser | Glu | Asn | Asn | Ile | Val | Met | |
| 1 | | | | 5 | | | | | 10 | | | | | 15 | | |

| GCA | GAT | GTA | GCG | GTT | TTA | GAA | AAA | ACC | CTT | GGT | ATA | GAT | TCT | AAT | ACA | 96 |
| Ala | Asp | Val | Ala | Val | Leu | Glu | Lys | Thr | Leu | Gly | Ile | Asp | Ser | Asn | Thr | |
| | | | 20 | | | | | 25 | | | | | 30 | | | |

| ACA | AAA | CCC | TTA | TCT | CTT | CAA | ACC | GTT | AAA | TAT | GAT | GAA | AAT | AAT | TCT | 144 |
| Thr | Lys | Pro | Leu | Ser | Leu | Gln | Thr | Val | Lys | Tyr | Asp | Glu | Asn | Asn | Ser | |
| | | 35 | | | | 40 | | | | | 45 | | | | | |

| ACA | GAT | ATA | CTA | GAT | ACA | GAA | CCT | CTA | ATA | AGT | TCT | ATG | GAA | ACT | GAA | 192 |
| Thr | Asp | Ile | Leu | Asp | Thr | Glu | Pro | Leu | Ile | Ser | Ser | Met | Glu | Thr | Glu | |
| | 50 | | | | 55 | | | | | 60 | | | | | | |

| AAT | ATT | TTA | TCG | ACT | AAA | CAA | AAA | AGA | AAC | GGT | CCC | AAA | AAA | ATG | ACA | 240 |
| Asn | Ile | Leu | Ser | Thr | Lys | Gln | Lys | Arg | Asn | Gly | Pro | Lys | Lys | Met | Thr | |
| 65 | | | | | 70 | | | | | 75 | | | | | 80 | |

| CGT | GAA | AGT | TTG | GCA | CTT | TAA | | | | | | | | | | 261 |
| Arg | Glu | Ser | Leu | Ala | Leu | * | | | | | | | | | | |
| | | | | 85 | | | | | | | | | | | | |

( 2 ) INFORMATION FOR SEQ ID NO:34:

( i ) SEQUENCE CHARACTERISTICS:
    ( A ) LENGTH: 86 amino acids
    ( B ) TYPE: amino acid
    ( D ) TOPOLOGY: linear ( i i ) MOLECULE TYPE: protein ( x i ) SEQUENCE DESCRIPTION: SEQ ID NO:34:

| Gly | Gly | Ala | Gln | Ala | Ile | Lys | Met | Thr | Ser | Glu | Asn | Asn | Ile | Val | Met |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Asp | Val | Ala | Val | Leu | Glu | Lys | Thr | Leu | Gly | Ile | Asp | Ser | Asn | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Lys | Pro | Leu | Ser | Leu | Gln | Thr | Val | Lys | Tyr | Asp | Glu | Asn | Asn | Ser |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Thr | Asp | Ile | Leu | Asp | Thr | Glu | Pro | Leu | Ile | Ser | Ser | Met | Glu | Thr | Glu |
|-----|-----|-----|-----|-----|-----|-----|-----|-----|-----|-----|-----|-----|-----|-----|-----|
|     | 50  |     |     |     |     | 55  |     |     |     |     |     | 60  |     |     |     |

| Asn | Ile | Leu | Ser | Thr | Lys | Gln | Lys | Arg | Asn | Gly | Pro | Lys | Lys | Met | Thr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Arg | Glu | Ser | Leu | Ala | Leu |
|-----|-----|-----|-----|-----|-----|
|     |     |     |     | 85  |     |

( 2 ) INFORMATION FOR SEQ ID NO:35:

( i ) SEQUENCE CHARACTERISTICS:
        ( A ) LENGTH: 280 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..280

( x i ) SEQUENCE DESCRIPTION: SEQ ID NO:35:

| T | GCA | TTA | AAT | TTT | ATT | AAA | TTA | GAA | AAA | AAT | AAT | CCA | GTA | TAT | TAT | 46 |
|---|-----|-----|-----|-----|-----|-----|-----|-----|-----|-----|-----|-----|-----|-----|-----|----|
|   | Ala | Leu | Asn | Phe | Ile | Lys | Leu | Glu | Lys | Asn | Asn | Pro | Val | Tyr | Tyr |    |
|   | 1   |     |     |     | 5   |     |     |     |     | 10  |     |     |     |     | 15  |    |

| TTT | CCG | GAA | CCT | ATG | GCA | TTC | TGG | CGT | ATC | ATC | CTA | GAA | ACA | GAT | ATT | 94 |
|-----|-----|-----|-----|-----|-----|-----|-----|-----|-----|-----|-----|-----|-----|-----|-----|----|
| Phe | Pro | Glu | Pro | Met | Ala | Phe | Trp | Arg | Ile | Ile | Leu | Glu | Thr | Asp | Ile |    |
|     |     |     |     | 20  |     |     |     |     | 25  |     |     |     |     | 30  |     |    |

| GTG | CAA | GGT | ATA | TAC | TCA | GTA | CAA | GAC | CGG | AAG | CTG | CGT | GGT | GAA | TTA | 142 |
|-----|-----|-----|-----|-----|-----|-----|-----|-----|-----|-----|-----|-----|-----|-----|-----|-----|
| Val | Gln | Gly | Ile | Tyr | Ser | Val | Gln | Asp | Arg | Lys | Leu | Arg | Gly | Glu | Leu |     |
|     |     |     | 35  |     |     |     |     | 40  |     |     |     |     | 45  |     |     |     |

| AGC | CTA | AAT | GAT | GCG | TCA | TTA | ATT | ACA | GCT | CAA | CTT | CAA | ACT | AAA | TTT | 190 |
|-----|-----|-----|-----|-----|-----|-----|-----|-----|-----|-----|-----|-----|-----|-----|-----|-----|
| Ser | Leu | Asn | Asp | Ala | Ser | Leu | Ile | Thr | Ala | Gln | Leu | Gln | Thr | Lys | Phe |     |
|     |     | 50  |     |     |     |     | 55  |     |     |     |     | 60  |     |     |     |     |

| TCT | ACG | CCA | TAT | ATT | TTA | CTT | CAT | TCC | AAT | GTA | TCC | AAA | TTT | TTT | GGA | 238 |
|-----|-----|-----|-----|-----|-----|-----|-----|-----|-----|-----|-----|-----|-----|-----|-----|-----|
| Ser | Thr | Pro | Tyr | Ile | Leu | Leu | His | Ser | Asn | Val | Ser | Lys | Phe | Phe | Gly |     |
|     | 65  |     |     |     |     | 70  |     |     |     |     | 75  |     |     |     |     |     |

| GAA | AAT | GTA | ACA | TTT | GGA | ATT | CCG | GAA | GTA | ATA | TTT | ATT | TTT | 280 |
|-----|-----|-----|-----|-----|-----|-----|-----|-----|-----|-----|-----|-----|-----|-----|
| Glu | Asn | Val | Thr | Phe | Gly | Ile | Pro | Glu | Val | Ile | Phe | Ile | Phe |     |
| 80  |     |     |     |     | 85  |     |     |     |     | 90  |     |     |     |     |

( 2 ) INFORMATION FOR SEQ ID NO:36:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

| Ala | Leu | Asn | Phe | Ile | Lys | Leu | Glu | Lys | Asn | Asn | Pro | Val | Tyr | Tyr | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Glu | Pro | Met | Ala | Phe | Trp | Arg | Ile | Ile | Leu | Glu | Thr | Asp | Ile | Val |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gln | Gly | Ile | Tyr | Ser | Val | Gln | Asp | Arg | Lys | Leu | Arg | Gly | Glu | Leu | Ser |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Leu | Asn | Asp | Ala | Ser | Leu | Ile | Thr | Ala | Gln | Leu | Gln | Thr | Lys | Phe | Ser |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Pro | Tyr | Ile | Leu | Leu | His | Ser | Asn | Val | Ser | Lys | Phe | Phe | Gly | Glu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Asn | Val | Thr | Phe | Gly | Ile | Pro | Glu | Val | Ile | Phe | Ile | Phe |
|-----|-----|-----|-----|-----|-----|-----|-----|-----|-----|-----|-----|-----|
|     |     |     |     | 85  |     |     |     |     | 90  |     |     |     |

( 2 ) INFORMATION FOR SEQ ID NO:37:

( i ) SEQUENCE CHARACTERISTICS:
        ( A ) LENGTH: 280 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

| AAAAATAAAT | ATTACTTCCG | GAATTCCAAA | TGTTACATTT | TCTCCAAAAA | ATTTGGATAC | 60  |
| ATTGGAATGA | AGTAAAATAT | ATGGCGTAGA | AAATTTAGTT | TGAAGTTGAG | CTGTAATTAA | 120 |
| TGACGCATCA | TTTAGGCTTA | ATTCACCACG | CAGCTTCCGG | TCTTGTACTG | AGTATATACC | 180 |
| TTGCACAATA | TCTGTTTCTA | GGATGATACG | CCAGAATGCC | ATAGGTTCCG | GAAAATAATA | 240 |
| TACTGGATTA | TTTTTTTCTA | ATTTAATAAA | ATTTAATGCA |            |            | 280 |

( 2 ) INFORMATION FOR SEQ ID NO:38:

( i ) SEQUENCE CHARACTERISTICS:
        ( A ) LENGTH: 279 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

| GCATTAAATT | TTATTAAATT | AGAAAAAAAT | AATCCAGTAT | ATTATTTTCC | GGAACCTATG | 60  |
| GCATTCTGGC | GTATCATCCT | AGAAACAGAT | ATTGTGCAAG | GTATATACTC | AGTACAAGAC | 120 |
| CGGAAGCTGC | GTGGTGAATT | AAGCCTAAAT | GATGCGTCAT | TAATTACAGC | TCAACTTCAA | 180 |
| ACTAAATTTT | CTACGCCATA | TATTTTACTT | CATTCCAATG | TATCCAAATT | TTTTGGAGAA | 240 |
| AATGTAACAT | TTGGAATTCC | GGAAGTAATA | TTTATTTTT  |            |            | 279 |

( 2 ) INFORMATION FOR SEQ ID NO:39:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..27
        ( D ) OTHER INFORMATION: /label=primer ( i x ) FEATURE:
        ( A ) NAME/KEY: N =Inosine
        ( B ) LOCATION: 11

( i x ) FEATURE:
        ( A ) NAME/KEY: N =Inosine ( B ) LOCATION: 17

( i x ) FEATURE:
                    ( A ) NAME/KEY: N =Inosine
                    ( B ) LOCATION: 20

( x i ) SEQUENCE DESCRIPTION: SEQ ID NO:39:

GGCGAATTCC NAARMGNGAN GARGA Y G                27

( 2 ) INFORMATION FOR SEQ ID NO:40:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: 1..24
                ( D ) OTHER INFORMATION: /label=primer ( i x ) FEATURE:
                ( A ) NAME/KEY: N =Inosine
                ( B ) LOCATION: 11

( i x ) FEATURE:
                ( A ) NAME/KEY: N =Inosine
                ( B ) LOCATION: 13

( i x ) FEATURE:
                ( A ) NAME/KEY: N =Inosine
                ( B ) LOCATION: 16

( i x ) FEATURE:
                ( A ) NAME/KEY: N =Inosine
                ( B ) LOCATION: 22

( x i ) SEQUENCE DESCRIPTION: SEQ ID NO:40:

CGCGGATCCG NTNSWNCC Y A ANCC                24

( 2 ) INFORMATION FOR SEQ ID NO:41:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: 1..26
                ( D ) OTHER INFORMATION: /label=primer ( i x ) FEATURE:
                ( A ) NAME/KEY: N =Inosine
                ( B ) LOCATION: 18

( i x ) FEATURE:
                ( A ) NAME/KEY: N =Inosine
                ( B ) LOCATION: 24

( x i ) SEQUENCE DESCRIPTION: SEQ ID NO:41:

GGCGAATTCT A Y CA Y WSNCA Y GT-
NTA                26

( 2 ) INFORMATION FOR SEQ ID NO:42:

( i ) SEQUENCE CHARACTERISTICS:
                ( A ) LENGTH: 30 base pairs ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: misc_feature
                    ( B ) LOCATION: 1..30
                    ( D ) OTHER INFORMATION: /label=primer ( i x ) FEATURE:
                    ( A ) NAME/KEY: N =Inosine
                    ( B ) LOCATION: 16

( i x ) FEATURE:
                    ( A ) NAME/KEY: N =Inosine
                    ( B ) LOCATION: 19

( i x ) FEATURE:
                    ( A ) NAME/KEY: N =Inosine
                    ( B ) LOCATION: 24

( i x ) FEATURE:
                    ( A ) NAME/KEY: N =Inosine
                    ( B ) LOCATION: 25

( i x ) FEATURE:
                    ( A ) NAME/KEY: N =Inosine
                    ( B ) LOCATION: 28

( x i ) SEQUENCE DESCRIPTION: SEQ ID NO:42:

CGCGGATCCR TCRTTNSWNG GDANNSWNGT          30

( 2 ) INFORMATION FOR SEQ ID NO:43:

( i ) SEQUENCE CHARACTERISTICS:
                    ( A ) LENGTH: 23 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: misc_feature
                    ( B ) LOCATION: 1..20
                    ( D ) OTHER INFORMATION: /label=primer ( i x ) FEATURE:
                    ( A ) NAME/KEY: N =Inosine
                    ( B ) LOCATION: 12

( i x ) FEATURE:
                    ( A ) NAME/KEY: N =Inosine
                    ( B ) LOCATION: 18

( i x ) FEATURE:
                    ( A ) NAME/KEY: N =Inosine
                    ( B ) LOCATION: 21

( x i ) SEQUENCE DESCRIPTION: SEQ ID NO:43:

GGCGAATTCG GNAARWSNAC NRC          23

( 2 ) INFORMATION FOR SEQ ID NO:44:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: misc_feature ( B ) LOCATION: 1..20
                        ( D ) OTHER INFORMATION: /label=primer ( i x ) FEATURE:
                        ( A ) NAME/KEY: N =Inosine
                        ( B ) LOCATION: 15

( x i ) SEQUENCE DESCRIPTION: SEQ ID NO:44:

GGCGGATCCG GTTGNCKRTC 20

( 2 ) INFORMATION FOR SEQ ID NO:45:

( i ) SEQUENCE CHARACTERISTICS:
                        ( A ) LENGTH: 30 base pairs
                        ( B ) TYPE: nucleic acid
                        ( C ) STRANDEDNESS: single
                        ( D ) TOPOLOGY: linear ( i i ) MOLECULE TYPE: DNA (genomic)

( i x ) FEATURE:
                        ( A ) NAME/KEY: misc_feature
                        ( B ) LOCATION: 1..30
                        ( D ) OTHER INFORMATION: /label=label ( x i ) SEQUENCE DESCRIPTION: SEQ ID NO:45:

CGCGGATCCA AGGTAATAAG TCAAAATGAG 30

( 2 ) INFORMATION FOR SEQ ID NO:46:

( i ) SEQUENCE CHARACTERISTICS:
                        ( A ) LENGTH: 29 base pairs
                        ( B ) TYPE: nucleic acid
                        ( C ) STRANDEDNESS: single
                        ( D ) TOPOLOGY: linear ( i i ) MOLECULE TYPE: DNA (genomic)

( i x ) FEATURE:
                        ( A ) NAME/KEY: misc_feature
                        ( B ) LOCATION: 1..29
                        ( D ) OTHER INFORMATION: /label=primer ( x i ) SEQUENCE DESCRIPTION: SEQ ID NO:46:

CGCGGATCCG ACAAAAACAA AAAGTAATG 29

( 2 ) INFORMATION FOR SEQ ID NO:47:

( i ) SEQUENCE CHARACTERISTICS:
                        ( A ) LENGTH: 28 base pairs
                        ( B ) TYPE: nucleic acid
                        ( C ) STRANDEDNESS: single
                        ( D ) TOPOLOGY: linear ( i i ) MOLECULE TYPE: DNA (genomic)

( i x ) FEATURE:
                        ( A ) NAME/KEY: misc_feature
                        ( B ) LOCATION: 1..26
                        ( D ) OTHER INFORMATION: /label=primer ( i x ) FEATURE:
                        ( A ) NAME/KEY: N =Inosine
                        ( B ) LOCATION: 11

( i x ) FEATURE:
                        ( A ) NAME/KEY: N =Inosine
                        ( B ) LOCATION: 20

( x i ) SEQUENCE DESCRIPTION: SEQ ID NO:47:

CCGAATTCYT NATGATHYTN ATHGARGG 28

(2) INFORMATION FOR SEQ ID NO:48:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..29
    (D) OTHER INFORMATION: /label=primer (ix) FEATURE:
    (A) NAME/KEY: N =Inosine
    (B) LOCATION: 21

(xi) SEQUENCE DESCRIPTION: SEQ ID NO:48:

CCGGATCC Y T CRAARAARTT NGTRTG Y TT          29

(2) INFORMATION FOR SEQ ID NO:49:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..35
    (D) OTHER INFORMATION: /label=primer (xi) SEQUENCE DESCRIPTION: SEQ ID NO:49:

TCCCCCGGGG GCGCGCCTTG ACATTGATTA TTGAC          35

(2) INFORMATION FOR SEQ ID NO:50:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..35
    (D) OTHER INFORMATION: /label=primer (xi) SEQUENCE DESCRIPTION: SEQ ID NO:50:

GCCCTTAAGG GGCGCGCCAA TGCGATGCAA TTTCC          35

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated canine herpesvirus (CHV) nucleic acid molecule that hybridizes under stringent hybridization conditions with a CHV nucleic acid region selected from the group consisting of a CdUPTase gene, a CgE gene, a CgG gene, a CgI gene, a CPK gene, a CTK gene, a CIR6 gene, a CUS2 gene, a CUS9 gene, a CUL49 gene, a CUL51 gene, a CUL48 gene, a CUL52 gene and a region of the CHV genome spanning from the 3' end of the coding region of the CUL41 gene through the 3' end of the coding region of the CUL38 gene.

2. The CHV nucleic acid molecule of claim 1, wherein said CdUTPase gene comprises $nCdUTP_{459}$, wherein said CgE gene comprises $nCgE_{750}$, wherein said CgG gene comprises $nCgG_{1248}$, wherein said CgI gene comprises $nCgI_{161}$, wherein said CPK gene comprises $nCPK_{1203}$, wherein said CTK gene comprises $nCTK_{280}$, wherein said CIR6 gene comprises $nCIR6_{552}$, wherein said CUS2 gene comprises $nCUS2_{1176}$, wherein said CUS9 gene comprises $nCUS9_{579}$, wherein said CUL49 gene is included in $nCHin_{3000}$, wherein said CUL51 gene comprises nCUL51$_{261}$, wherein said CUL48 gene comprises nCUL48$_{294}$, and wherein said CUL52 gene comprises nCUL52$_{146}$.

3. The CHV nucleic acid molecule of claim 1, wherein said CHV nucleic acid molecule comprises a nucleic acid sequence that is at least 80% identical to a nucleic acid sequence selected from the group consisting of SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, and SEQ ID NO:38.

4. The CHV nucleic acid molecule of claim 1, wherein said nucleic acid molecule hybridizes under stringent hybridization conditions with a nucleic acid molecule selected from the group consisting of nCIR6$_{552}$, nCUS2$_{1176}$, nCPK$_{1203}$, nCgG$_{1248}$, nCgI$_{161}$, nCgE750, nCUS9$_{579}$, nCdUTP/nCUL51$_{743}$, nCTK$_{280}$, nCUL48$_{294}$, and nCUL52$_{146}$.

5. The CHV nucleic acid molecule of claim 1, wherein said CHV nucleic acid molecule comprises a CHV nucleic acid molecule selected from the group consisting of nCAsc$_{9300}$, nCAsc$_{10000}$, nCHin$_{3000}$, nCHin$_{1900}$, nCUS$_{5495}$, nCIR6$_{552}$, nCUS2$_{1176}$, nCPK$_{1203}$, nCgG$_{1248}$, nCdUTP/CUL51$_{743}$, nCdUTP$_{459}$, nCUS9$_{579}$, nCUS9$_{450}$, nCUL48$_{294}$, nCUL48$_{291}$, nCUL52$_{146}$, nCUL52$_{144}$, nCgI$_{161}$, nCgI$_{159}$, nCgE$_{750}$, nCTK$_{280}$, nCTK$_{279}$, nCUL51$_{261}$, and allelic variants of said CHV nucleic acid molecules.

6. The CHV nucleic acid molecule of claim 1, wherein said CHV nucleic acid molecule is selected from the group consisting of: a CHV nucleic acid molecule comprising a nucleic acid sequence selected from the group consisting of SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, and SEQ ID NO:38; and a nucleic acid molecule comprising an allelic variant of any of said CHV nucleic acid molecules.

7. A recombinant molecule comprising a CHV nucleic acid molecule as set forth in claim 1 operatively linked to a transcription control sequence.

8. A recombinant virus comprising an isolated CHV nucleic acid region selected from the group consisting of a CdUTPase gene, a CgE gene, a CgG gene, a CgI gene, a CPK gene, a CTK gene, a CIR6 gene, a CUS2 gene, a CUS9 gene, a CUL49 gene, a CUL51 gene, a CUL48 gene, a CUL52 gene and a region of the CHV genome spanning from the 3' end of the coding region of the CUL41 gene through the 3' end of the coding region of the CUL38 gene and portions thereof, wherein a portion encodes an epitope that elicits an immune response against a CHV protein.

9. A recombinant cell comprising a CHV nucleic acid molecule as set forth in claim 1.

10. A recombinant vector comprising an isolated CHV nucleic acid region selected from the group consisting of a CdUTPase gene, a CgE gene, a CgG gene, a CgI gene, a CPK gene, a CTK gene, a CIR6 gene, a CUS2 gene, a CUS9 gene, a CUL49 gene, a CUL51 gene, a CUL48 gene, a CUL52 gene and a region of the CHV genome spanning from the 3' end of the coding region of the CUL41 gene through the 3' end of the coding region of the CUL38 gene and portions thereof, wherein the portion forms a stable hybrid with the complementary sequence of one of said regions.

11. A cell comprising said recombinant vector of claim 10.

12. A recombinant CHV comprising a recombinant CHV genome, said CHV genome comprising a heterologous nucleic acid molecule operatively linked to a transcription control region, said heterologous nucleic acid molecule being in a region of said CHV genome selected from the group consisting of a nonessential gene of said CHV genome and an intergenic region of said CHV genome, said CHV being reproduction competent.

13. The CHV of claim 12, wherein said CHV comprises a recombinant CHV genome having an inactive gene.

14. The CHV of claim 13, wherein said inactive gene comprises an alteration selected from the group consisting of a deletion of one or more nucleotides, an insertion of one or more nucleotides, an inversion of one or more nucleotides, and a substitution of one or more nucleotides.

15. The CHV of claim 13, wherein said inactive gene comprises said heterologous nucleic acid molecule.

16. The CHV of claim 12, wherein said CHV is selected from the group consisting of a CdUTPase negative CHV, a CgC negative CHV, a CgE negative CKV, a CgG negative CEV, a CgI negative CHV, a CPk negative CHV, a CTK negative CHV, a CIR6 negative CHV, a CUS2 negative CHV, a CUS9 negative CkIv, a CUL49 negative CHV and a CUL45 negative CHV.

17. The CHV of claim 16, wherein said CHV is attenuated.

18. The CHV of claim 12, wherein said CHV comprises a recombinant CHV genome having a heterologous nucleic acid molecule in a CHV gene of said CHV genome, wherein said CHV gene is selected from the group consisting of a CdUTPase gene, a CgC gene, a CgE gene, a CgG gene, a CgI gene, a CPK gene, a CTK gene, a CIR6 gene, a CUS2 gene, a CUS9 gene, a CUL49 gene, and a CUL45 gene.

19. The CHV of claim 12, wherein said CHV comprises a recombinant CHV genome having a heterologous nucleic acid molecule in a region of said CHV genome spanning from the 3' end of the coding region of the CUL41 gene through the 3' end of the coding region of the CUL38 gene.

20. The CHV of claim 12, wherein said CHV comprises a recombinant CHV genome having a heterologous nucleic acid molecule in a naturally-occurring AscI restriction endonuclease site wit in said CHV genome.

21. The CHV of claim 12, wherein said CHV comprises a recombinant CHV genome having a heterologous nucleic acid molecule in the US region of said CHV genome at a position selected from the group consisting of a nonessential gene in said US region an a intergenic site in said US region.

22. The CHV of claim 12, wherein said CHV comprises a recombinant CHV genome having a heterologous nucleic acid molecule in a region of said CHV genome selected from the group consisting of nCAsc$_{9300}$, nCAsc$_{10000}$, nCHin$_{3000}$, nCHin$_{1900}$, and allelic variants of aid regions, wherein said heterologous nucleic acid molecule does not abrogate growth of said CHV in tissue culture.

23. The CHV of claim 12, wherein said CHV comprises a recombinant CHV genome having a heterologous nucleic acid molecule in a region of said CHV genome selected from the group consisting of US region comprising nCUS$_{5495}$, a CHV UL region spanning CgC and CUL45 comprising nCgC/CUL45$_{2100}$, a CgE gene comprising nCgE$_{750}$, a CgI gene comprising nCgI$_{161}$, a CUS9 gene comprising nCUS9$_{579}$, a CHV UL region spanning CdUTPase and CUL51 comprising ncdUTP/CUL51$_{743}$, a CTK gene comprising nCTK$_{280}$, a CUL49 gene included in nCHin$_{3000}$, and allelic variants of said regions, wherein said heterologous nucleic acid molecule does not abrogate growth of said CHV in tissue culture.

24. The CHV of claim 12, wherein said CHV comprises a recombinant CHV genome having a heterologous nucleic acid molecule in a region of said CHV genome selected from the group consisting of $nCUS_{5495}$, $nCgC/CUL45_{2100}$, $nCgE_{750}$, $nCgI_{161}$, $nCUS9_{579}$,-$nCdUTP/CUL51_{743}$, $nCTK_{280}$, and allelic variants of said regions, wherein said heterologous nucleic acid molecule does not abrogate growth of said CHV in tissue culture.

25. The CHV of claim 12, wherein said CHV comprises a recombinant CHV genome having a heterologous nucleic acid molecule in a region of said CHV genome represented by a nucleic acid sequence comprising a nucleic acid sequence selected from the group consisting of SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:29, SEQ ID NO:31, SEQ ID NO:32, SEQ ID NO:35, SEQ ID NO:37, SEQ ID NO:38, and allelic variants of said regions, wherein said heterologous nucleic acid molecule does not abrogate growth of said CHV in tissue culture.

26. The CHV of claim 12, wherein said heterologous nucleic acid molecule encodes a compound selected from the group consisting of orateins and RNA species.

27. The CHV of claim 26, wherein said compound is derived from a infectious agent selected from the group consisting of protozoan parasites, helminth parasites, ectoparasites, fungi bacteria, and viruses.

28. The CHV of claim 12, wherein said heterologous nucleic acid molecule comprises a gene encoding an immunomodulator.

29. The CHV of claim 12, wherein said CHV infects dogs.

30. A recombinant CHV genome comprising a heterologous nucleic acid molecule operatively linked to a transcription control region said heterologous nucleic acid molecule being in a region of said CHV genome selected from the group consisting of a nonessential gene of said CHV genome and an intergenic region of said CHV genome, said CHV genome is reproduction competent.

31. The CHV genome of claim 30, wherein said CHV genome comprises an inactive gene.

32. The CHV genome of claim 31, wherein said inactive gene comprises an alteration selected from the group consisting of a deletion of one or more nucleotides, an insertion of one or more nucleotides, an inversion of one or more nucleotides, and a substitution of one or more nucleotides.

33. The CHV genome of claim 31, wherein said inactive gene comprises said heterologous nucleic acid molecule.

34. The CHV genome of claim 30, wherein said CHV genome is selected from the group consisting of a CdUTPase negative CHV genome, a CgG negative CHV genome, a CgE negative CHV genome, a CgG negative CHV genome, a CgI negative CHV genome, a CPK negative CHV genome, a CTK negative CHV genome, a CIR6 negative CHV genome a CUS2 negative CHV genome, a CUS9 negative CHV genome, a CUL49 negative CHV genome, and a CUL45 negative CHV genome.

35. The CHV genome of claim 30, wherein said heterologous nucleic acid molecule is in a CHV gene selected from the group consisting of a CdUTPase gene, a CgC gene, a CgE gene, a CgG gene, a CgI gene, a CPK gene, a CTK gene, a CIR6 gene, a CUS2 gene, a CUS9 gene, a CUL49 gene, and a CUL45 gene.

36. The CHV genome of claim 30, wherein said heterologous nucleic acid molecule is in a region of said CHV genome spanning from the 3' end of the coding region of the CUL41 gene through the 3' end of the coding region of the CUL38 gene.

37. The CHV genome of claim 30, wherein said CHV genome comprises a heterologus nucleic acid molecule in a naturally-occurring AscI restriction endonuclease site in raid CHV genome.

38. The CHV genome of claim 30, wherein said CHV genome comprises a heterologous nucleic acid molecule in the US region of said CHV genome at a position selected from the group consisting of a non-essential gene in said US region and an intergenic site in said US region.

39. The CHV genome of claim 30, wherein said CEV genome comprises a heterologous nucleic acid molecule in a region of said CHV genome selected from the group consisting of $nCAsc_{9300}$, $nCAsc_{10000}$, $nCHin3000$, $nCHin_{1900}$, and allelic variants of said regions, wherein said heterologous nucleic acid molecule does not abrogate growth of said CHV in tissue culture.

40. The CHV genome of claim 30, wherein said CHV genome comprises a heterologous nucleic acid molecule in a region of said CHV genome selected from the group consisting of a CHV US region comprising $nCUS_{5495}$, a CHV UL region spanning CgC and CUL45 comprising /$CUL45_{2100}$, a CgE gene comprising $nCgE_{750}$, a CgI gene comprising $nCgI_{161}$, a CUS9 gene comprising $nCUS9_{579}$, a CHV UL region spanning CdUTPase and CUL51 comprising $nCdUTP/CUL51_{743}$, a CTK gene comprising $nCTK_{280}$, a CUL49 gene included in $nCHin_{3000}$ and allelic variants of said regions, wherein said heterologous nucleic acid molecule does not abrogate growth of said CHV in tissue culture.

41. The CHV genome of claim 30, wherein said CHV genome comprises a heterologous nucleic acid molecule in a region of said CHV genome Selected from the group consisting of $nCUS_{5495}$, $nCgC/CUL45_{2100}$, $nCgE_{750}$, $nCgI_{161}$, $nCUS9_{579}$, $nCdUTP/CUL51_{743}$, $nCTK_{280}$, and allelic variants of said regions, wherein said heterologous nucleic acid molecule does not abrogate growth of said CHV in tissue culture.

42. The CHV genome of claim 30, wherein said CHV genome comprises a heterologous nucleic acid molecule in a region of said CHV genome represented by a nucleic acid sequence comprising a nucleic acid sequence selected from the group consisting of SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:29, SEQ ID NO:31, SEQ ID NO:32, SEQ ID NO:35, SEQ ID NO:37, SEQ ID NO:38, and allelic variants said regions, wherein said heterologous nucleic acid molecule does not abrogate growth of said CHV in tissue culture.

43. The CHV genome of claim 30, wherein said heterologous nucleic acid molecule encodes a compound selected from the group consisting of proteins and RNA species.

44. The CHV genome of claim 43, wherein said compound is derived from an infectious agent selected from the group consisting of protozoan parasites, helminth parasites, ectoparasites, fungi, bacteria, and viruses.

45. The CHV genome of claim 30, wherein said heterologous nucleic acid molecule comprises a gene encoding an immunomodulator.

46. A transfected cell comprising a CHV genome as set forth in claim 30.

47. The CHV genome of claim 30, wherein said CHV genome comprises a recombinant dog herpesvirus genome.

48. A composition for delivery to a canid, said composition comprising a recombinant CHV comprising a recombinant CHV genome, said CHV genome comprising a heterologous nucleic acid molecule operatively linked to a transcription control region, said heterologous nucleic acid molecule being in a region of said CHV genome selected from the group consisting of a nonessential gene of said CHV genome and an intergenic region of said CHV genome, said CHV being reproduction competent.

49. The composition of claim 48, wherein said composition further comprises a component selected from the group consisting of an excipient, an adjuvant, and a carrier.

50. A composition for delivery to a canid, said composition comprising a recombinant CHV genome, said CHV genome comprising a recombinant CHV genome, said CHV genome comprising a heterologous nucleic acid molecule operatively linked to a transcription control region, said heterologous nucleic acid molecule being in a region of said CHV genome selected from the group consisting of a nonessential gene of said CHV genome and an intergenic region of said CHV genome, wherein a recombinant CHV comprising said CHV genome is reproduction competent.

51. The composition of claim 50, wherein said composition further comprises a component selected from the group consisting of an excipient, an adjuvant, and a carrier.

52. A method to deliver a compound to a canid, said method comprising administering to said canid a composition comprising a recombinant CHV comprising a recombinant CHV genome, said CHV genome comprising a heterologous nucleic acid molecule encoding said compound, operatively linked to a transcription control region, said heterologous nucleic acid molecule being in a region of said CHV genome selected from the group consisting of a nonessential gene of said CHV genome and an intergenic region of said CHV genome, said CHV being reproduction competent.

53. The method of claim 52, wherein said composition further comprises a component selected from the group consisting of an excipient, an adjuvant, and a carrier.

54. A method to deliver a compound to a canid, said method comprising administering to said canid a composition comprising a recombinant CHV genome, said CHV genome comprising a heterologous nucleic acid molecule encoding said compound, operatively linked to a transcription control region, said heterologous nucleic acid molecule being in a region of said CHV genome selected from the group consisting of a nonessential gene of said CHV genome and an intergenic region of said CHV genome, wherein a recombinant CHV comprising said CHV genome is reproduction competent.

55. The method of claim 54, wherein said composition further comprises a component selected from the group consisting of an excipient, an adjuvant, and a carrier.

56. A composition for delivery to a canid, said composition comprising an isolated CHV nucleic acid molecule as set forth in claim 1.

57. The composition of claim 56, wherein said composition further comprises a component selected from the group consisting of excipient, an adjuvant, and a carrier.

* * * * *

UNITED STATES PATENT AND TRADEMARK OFFICE
CERTIFICATE OF CORRECTION

PATENT NO : 5,753,235
DATED : May 19, 1998
INVENTOR(S): Haanes et al.

It is certified that error appears in the above-identified patent and that said Letters Patent are hereby corrected as shown below:

Claim 1, line 64, delete "CdUPTase" and insert –CdUTPase– therefor
Claim 4, line 18, delete "nCgE750" and insert –nCgE$_{750}$– therefor
Claim 16, line 21, delete "CKV" and insert –CHV– therefor
Claim 16, line 22, delete "CEV" and insert –CHV– therefor
Claim 16, line 22, delete "CPk" and insert –CPK– therefor
Claim 16, line 24, delete "CkIv" and insert –CHV– therefor
Claim 20, line 42, delete "AscI" and insert –*Asc*I– therefor
Claim 20, line 43, delete "wit in" and insert –within– therefor
Claim 21, line 48, delete "an a" and insert –and an– therefor
Claim 22, line 54, delete "aid" and insert –said– therefor
Claim 23, line 60, add "a CHV" between "of" and "US"
Claim 23, line 65, delete "ncdUTP/CUL51$_{743}$" and insert –nCdUTP/CUL51$_{743}$– therefor
Claim 26, line 26, delete "orateins" and insert –proteins– therefor
Claim 27, line 30, insert – , – after "fungi"
Claim 30, line 37, insert – , – after "region"
Claim 34, line 57, insert – , – before "a CUS2"
Claim 37, line 6, delete "AscI" and insert –*Asc*I– therefor
Claim 37, line 6, delete "raid" and insert –said– therefor
Claim 39, line 13, delete "CEV" and insert –CHV– therefor

UNITED STATES PATENT AND TRADEMARK OFFICE
CERTIFICATE OF CORRECTION

PATENT NO. : 5,753,235
DATED : May 19, 1998
INVENTOR(S) : Haanes et al.

It is certified that error appears in the above-identified patent and that said Letters Patent is hereby corrected as shown below:

Claim 39, line 16, delete "nCHin3000" and insert --nCHin$_{3000}$-- therefor
Claim 40, line 24, delete "/CUL45$_{2100}$" and insert --nCgC/CUL45$_{2100}$-- therefor
Claim 40, line 28, insert --,-- after "nCHin$_{3000}$"
Claim 41, line 34, delete "Selected" and insert --selected-- therefor Signed and Sealed this Thirtieth Day of May, 2000

Attest:

Q. TODD DICKINSON

*Attesting Officer*  *Director of Patents and Trademarks*